US010391124B2

(12) United States Patent
Weissman et al.

(10) Patent No.: US 10,391,124 B2
(45) Date of Patent: Aug. 27, 2019

(54) SILVER OXIDE FORMULATIONS

(71) Applicant: AIDANCE SKINCARE & TOPICAL SOLUTIONS LLC, Woonsocket, RI (US)

(72) Inventors: Aharon Weissman, Moreshet (IL); Perry Antelman, Sharon, MA (US); Shalom Lampert, Maalot (IL); David Goldsmith, Harmony, RI (US)

(73) Assignee: Aidance Skincare & Topical Solutions LLC, Woonsocket, RI (US)

( * ) Notice: Subject to any disclaimer, the term of this patent is extended or adjusted under 35 U.S.C. 154(b) by 0 days.

(21) Appl. No.: 15/495,560

(22) Filed: Apr. 24, 2017

(65) Prior Publication Data

US 2018/0028565 A1 Feb. 1, 2018

Related U.S. Application Data

(63) Continuation-in-part of application No. 13/508,373, filed as application No. PCT/US2010/055757 on Nov. 7, 2010, now Pat. No. 9,687,509, application No. 15/495,560, which is a continuation-in-part of application No. 14/176,096, filed on Feb. 9, 2014, now Pat. No. 9,629,913, which is a continuation-in-part of application No. 13/021,755, filed on Feb. 6, 2011, now abandoned, and a continuation-in-part of application No. 12/841,031, filed on Jul. 21, 2010, now Pat. No. 8,467,647, said application No. 14/176,096 is a continuation of application No. 13/981,393, filed as application No. PCT/US2012/022220 on Jan. 23, 2012, now abandoned.

(60) Provisional application No. 61/258,598, filed on Nov. 6, 2009, provisional application No. 61/314,457, filed on Mar. 16, 2010, provisional application No. 61/227,297, filed on Jul. 21, 2009.

(30) Foreign Application Priority Data

Mar. 9, 2010 (GB) .................................. 1003870.1
Jan. 24, 2011 (GB) .................................. 1101193.9
Feb. 4, 2011 (GB) .................................. 1101936.1

(51) Int. Cl.
*A61K 9/00* (2006.01)
*A61K 9/14* (2006.01)
*A61K 33/38* (2006.01)

(52) U.S. Cl.
CPC ............ *A61K 33/38* (2013.01); *A61K 9/0014* (2013.01); *A61K 9/14* (2013.01)

(58) Field of Classification Search
CPC ......... A61K 33/38; A61K 9/0014; A61K 9/14
See application file for complete search history.

(56) References Cited

U.S. PATENT DOCUMENTS 6,789,756 B2 * 9/2004 Beliavsky ............. B02C 19/061 241/39
2006/0210500 A1 * 9/2006 Bicard-Benhamou ....................... A61K 8/19 424/63

FOREIGN PATENT DOCUMENTS

JP 2003308730 A * 10/2003

OTHER PUBLICATIONS

Aldrich (Chemfiles, 2001, vol. 1, No. 3) (Year: 2001).*
Sigma Aldrich web page (Silver oxide [predominantly silver(II) oxide]; https://www.sigmaaldrich.com/catalog/product/aldrich/223638?lang=en®ion=US, 2018) (Year: 2018).*
Tissot et al (Thermochimica Acta, 1985, vol. 85, pp. 103-106) (Year: 1985).*

* cited by examiner

*Primary Examiner* — Mark V Stevens
(74) *Attorney, Agent, or Firm* — Daniel Feigelson Fourth Dimension IP

(57) ABSTRACT

Topical formulations for application to exposed body tissue.

19 Claims, 38 Drawing Sheets

90
85
80
75
70
65
←Darker L* Lighter→
0
5
10
15
20
%ZnO
0.25% AgO
0.5% AgO
1.0% AgO 90
88
86
84
82
80
78
76
74
72
70
←Darker L* Lighter→
0
5
10
15
20
%ZnO
0.25% AgO
0.5% AgO
1.0% AgO 90
85
80
75
70
65
←Darker L* Lighter→
0
5
10
15
20
ZnO to AgO Weight Ratio
0.25% AgO
0.5% AgO
1.0% AgO 87
85
83
81
79
77
75
73
71
←Darker L* Lighter→
0
5
10
15
20
ZnO to AgO Weight Ratio
0.25% AgO
0.5% AgO
1.0% AgO

| 2-Theta | d(Å) | BG | Height | H% | Area | A% | FWHM | XS(Å) |
|---|---|---|---|---|---|---|---|---|
| 15.854 | 5.5856 | 11.3 | 21.7 | 2.3 | 4.1 | 1.9 | 0.162 | 793 |
| 30.182 | 2.9587 | 7.3 | 21.7 | 2.3 | 4.1 | 1.9 | 0.161 | 690 |
| 32.039 | 2.7913 | 12.0 | 446.0 | 47.3 | 129.0 | 59.5 | 0.246 | 392 |
| 32.261 | 2.7726 | 12.1 | 941.9 | 100.0 | 216.8 | 100.0 | 0.196 | 523 |
| 34.177 | 2.6214 | 12.6 | 305.4 | 32.4 | 61.4 | 28.3 | 0.171 | 625 |
| 37.144 | 2.4185 | 10.2 | 739.8 | 78.5 | 165.6 | 76.4 | 0.190 | 538 |
| 39.383 | 2.2860 | 6.0 | 287.0 | 30.5 | 72.0 | 33.2 | 0.213 | 465 |
| 52.477 | 1.7423 | 7.2 | 74.8 | 7.9 | 19.6 | 9.0 | 0.223 | 454 |
| 53.858 | 1.7008 | 10.5 | 175.5 | 18.6 | 44.8 | 20.7 | 0.217 | 470 |
| 54.682 | 1.6772 | 11.3 | 104.7 | 11.1 | 24.9 | 11.5 | 0.202 | 513 |
| 56.700 | 1.6222 | 7.6 | 167.4 | 17.8 | 38.1 | 17.6 | 0.193 | 548 |
| 62.781 | 1.4789 | 12.4 | 96.6 | 10.3 | 23.7 | 10.9 | 0.209 | 516 |
| 63.656 | 1.4606 | 15.4 | 76.6 | 8.1 | 24.4 | 11.2 | 0.270 | 383 |
| 64.124 | 1.4511 | 13.2 | 88.8 | 9.4 | 25.9 | 12.0 | 0.248 | 424 |
| 65.561 | 1.4227 | 8.4 | 36.6 | 3.9 | 13.4 | 6.2 | 0.312 | 329 |
| 66.240 | 1.4098 | 8.7 | 61.3 | 6.5 | 23.1 | 10.7 | 0.321 | 321 |
| 66.960 | 1.3964 | 13.1 | 83.9 | 8.9 | 28.1 | 13.0 | 0.285 | 369 |
| 67.560 | 1.3854 | 6.1 | 62.9 | 6.7 | 26.4 | 12.2 | 0.358 | 287 |
| 69.379 | 1.3535 | 5.7 | 31.3 | 3.3 | 8.8 | 4.0 | 0.238 | 462 |
| 71.980 | 1.3108 | 4.7 | 32.3 | 3.4 | 10.3 | 4.7 | 0.270 | 406 |
| 79.252 | 1.2078 | 3.9 | 43.1 | 4.6 | 12.3 | 5.7 | 0.242 | 496 |

| 2-Theta | d(Å) | BG | Height | H% | Area | A% | FWHM | XS(Å) |
|---|---|---|---|---|---|---|---|---|
| 20.104 | 4.4133 | 5.7 | 4.3 | 0.9 | 1.3 | 0.6 | 0.257 | 383 |
| 32.202 | 2.7775 | 12.3 | 469.7 | 100.0 | 225.7 | 100.0 | 0.408 | 218 |
| 32.837 | 2.7253 | 19.9 | 41.1 | 8.8 | 12.4 | 5.5 | 0.257 | 372 |
| 34.141 | 2.6241 | 8.9 | 158.1 | 33.7 | 55.4 | 24.5 | 0.298 | 312 |
| 37.178 | 2.4164 | 13.9 | 334.1 | 71.1 | 122.6 | 54.3 | 0.312 | 287 |
| 39.460 | 2.2818 | 8.0 | 126.0 | 26.8 | 54.0 | 23.9 | 0.364 | 250 |
| 52.464 | 1.7427 | 10.3 | 31.7 | 6.8 | 10.3 | 4.5 | 0.275 | 355 |
| 53.840 | 1.7014 | 12.4 | 82.6 | 17.6 | 33.3 | 14.7 | 0.343 | 279 |
| 54.700 | 1.6766 | 9.9 | 42.1 | 9.0 | 20.4 | 9.1 | 0.412 | 229 |
| 56.700 | 1.6222 | 8.5 | 69.5 | 14.8 | 28.7 | 12.7 | 0.351 | 276 |
| 62.824 | 1.4780 | 6.3 | 52.7 | 11.2 | 22.2 | 9.8 | 0.358 | 279 |
| 63.682 | 1.4601 | 6.3 | 57.7 | 12.3 | 38.4 | 17.0 | 0.566 | 172 |
| 64.162 | 1.4503 | 13.4 | 36.6 | 7.8 | 18.1 | 8.0 | 0.422 | 235 |
| 66.279 | 1.4090 | 13.6 | 31.4 | 6.7 | 17.1 | 7.6 | 0.462 | 216 |
| 67.015 | 1.3953 | 22.7 | 38.3 | 8.2 | 16.7 | 7.4 | 0.370 | 275 |
| 67.559 | 1.3854 | 7.7 | 31.3 | 6.7 | 27.3 | 12.1 | 0.743 | 132 |
| 75.780 | 1.2542 | 4.1 | 4.9 | 1.0 | 0.4 | 0.2 | 0.071 | >1000 |

| 2-Theta | d(Å) | BG | Height | H% | Area | A% | FWHM | XS(Å) |
|---|---|---|---|---|---|---|---|---|
| 32.280 | 2.7710 | 11 | 392 | 100.0 | 211.0 | 100.0 | 0.458 | 193 |
| 32.818 | 2.7268 | 21 | 49 | 12.4 | 40.4 | 19.2 | 0.706 | 122 |
| 34.162 | 2.6226 | 12 | 133 | 33.9 | 49.4 | 23.4 | 0.316 | 291 |
| 37.220 | 2.4138 | 17 | 262 | 66.9 | 109.6 | 51.9 | 0.356 | 256 |
| 39.440 | 2.2829 | 11 | 112 | 28.7 | 47.7 | 22.6 | 0.361 | 253 |
| 42.280 | 2.1359 | 5 | 5 | 1.2 | 1.0 | 0.5 | 0.184 | 562 |
| 43.053 | 2.0993 | 5 | 3 | 0.7 | 0.4 | 0.2 | 0.122 | 999 |
| 53.899 | 1.6997 | 13 | 74 | 18.9 | 29.8 | 14.1 | 0.342 | 280 |
| 54.778 | 1.6744 | 15 | 33 | 8.4 | 12.6 | 6.0 | 0.325 | 298 |
| 56.781 | 1.6200 | 9 | 54 | 13.7 | 22.8 | 10.8 | 0.361 | 268 |
| 62.784 | 1.4788 | 7 | 44 | 11.2 | 22.7 | 10.8 | 0.441 | 222 |
| 63.721 | 1.4593 | 7 | 42 | 10.7 | 31.6 | 15.0 | 0.643 | 150 |
| 64.241 | 1.4487 | 12 | 29 | 7.4 | 25.9 | 12.3 | 0.764 | 126 |
| 66.220 | 1.4102 | 12 | 21 | 5.3 | 12.1 | 5.8 | 0.495 | 201 |
| 67.042 | 1.3948 | 16 | 35 | 9.0 | 23.2 | 11.0 | 0.561 | 176 |
| 67.696 | 1.3830 | 8 | 24 | 6.1 | 20.9 | 9.9 | 0.746 | 132 |
| 67.762 | 1.3818 | 8 | 23 | 5.8 | 8.5 | 4.0 | 0.316 | 330 |
| 72.219 | 1.3071 | 5 | 22 | 5.6 | 6.4 | 3.0 | 0.247 | 452 |

SILVER OXIDE FORMULATIONS

CROSS-REFERENCE TO RELATED APPLICATIONS

This application is a continuation-in part of U.S. patent application Ser. No. 13/508,373 filed Jun. 25, 2012, which is a National Phase Application of International Patent Application No. PCT/US2010/055757, filed Nov. 7, 2010, which draws priority from U.S. Provisional Patent Application Ser. No. 61/258,598, filed Nov. 6, 2009, and from U.S. Provisional Patent Application Ser. No. 61/314,457, filed Mar. 16, 2010, all of which are incorporated by reference for all purposes as if fully set forth herein.

This application is also a continuation-in-part of U.S. patent application Ser. No. 14/176,096 filed Feb. 9, 2014 the contents of which are incorporated by reference for all purposes as if fully set forth herein. U.S. Ser. No. 14/176,096 is itself a continuation in part of the following three U.S. Patent Applications:

(1) U.S. patent application Ser. No. 13/021,755 filed Feb. 6, 2011, which draws priority from U.K. Patent Application No. GB1101936.1, filed Feb. 4, 2011 both of which are incorporated by reference for all purposes as if fully set forth herein;

(2) U.S. patent application Ser. No. 12/841,031, now U.S. Pat. No. 8,647,647, filed Jul. 21, 2012, which draws priority from U.K. Patent Application No. GB1003870.1, filed Mar. 9, 2010, and claims the benefit of U.S. Provisional Patent Application Ser. No. 61/227,297, filed Jul. 21, 2009, all of which are incorporated by reference for all purposes as if fully set forth herein;

(3) U.S. patent application Ser. No. 13/981,393, filed Jul. 24, 2013, which is a National Phase Application of International Patent Application No. PCT/US2012/022220, filed Jan. 23, 2012, which draws priority from U.K. Patent Application No. GB1101193.9, filed Jan. 24, 2011, all of which applications are incorporated by reference for all purposes as if fully set forth herein.

FIELD AND BACKGROUND OF THE INVENTION

The present invention relates to anti-microbial silver oxide formulations.

Silver and various silver derivatives are known to have anti-microbial properties. Silver(II) oxide is known to be more effective than silver(I) oxide. Commercial applications of such products include impregnated bandages, mold-free and odor-free textiles, and various kinds of skin creams. In addition, there exist several oral medicines that utilize silver as an active ingredient, including anti-smoking lozenges containing silver acetate ($AgC_2H_3O_2$), breath mints coated with silver, and silver nitrate solutions for treating gum disease.

One particularly effective group of silver derivatives is the group of silver oxides. Of the silver oxides, AgO is known to be more effective than $Ag_2O$.

It was reported by U.S. Pat. No. 6,258,385 to Antelman, which is incorporated by reference for all purposes as if fully set forth herein, that > the effects of the electron transfer involved with respect to the tetroxide, phenomenally, rendered it a more powerful germicide than other silver entities . . . . The oligodynamic properties of these entities may be summarized as follows, which is referred to as the Horsfal series:

$$Ag_4O_4>Ag(III)>Ag(II)>>>>Ag(I).$$

Skin creams containing silver(II) oxide have been reported to be efficacious in treating various medical conditions, including genital herpes, oral herpes, vaginitis, vaginal yeast infections, foot and nail fungus, burns, warts, and skin infections. These skin formulations are characterized by their creaminess and ease of application, which, inter alia, enables the polyvalent silver oxide to intimately contact the skin surface.

Disadvantageously, however, the various forms of silver oxide, and silver(II) oxide in particular, are dark gray or charcoal gray powders, and are thus extremely hard to hide within white creams used in various cosmetic or pharmaceutical topical applications. Moreover, the dark silver oxide particles may stain skin and clothing.

Chronic wound care is a critical and growing issue in healthcare systems. A chronic wound may be defined as a wound that shows no sign of appreciable healing within 2-3 months. Chronic wounds such as skin ulcers are the most common complication of diabetes, which has been termed a "Silent Epidemic". Above and beyond their economic burden on healthcare systems, chronic wounds represent a debilitating problem having significant clinical and social ramifications. Chronic wounds may be non-responsive or poorly responsive to various known treatments. Consequently, such chronic wounds may become severely infected, leading to gangrene and amputations.

While some advances have been made in the treatment of wounds, both chronic and acute, we believe there is a need for further improvements in formulating stable, efficacious topical silver oxide formulations, and the subject matter of the present disclosure and claims is aimed at fulfilling this need.

SUMMARY OF THE INVENTION

According to teachings of the present invention there is provided a topical formulation for application to exposed body tissue, the formulation including a silver oxide and zinc oxide, intimately dispersed within a carrier medium.

According to another aspect of the present invention there is provided a topical formulation for application to exposed body tissue, the formulation including a silver oxide and zinc oxide, the silver oxide and the zinc oxide intimately dispersed within a carrier medium, wherein the silver oxide includes, largely includes, predominantly includes, or consists essentially of a silver(II) oxide.

According to further features in the described preferred embodiments, the formulation contains at least 0.05%, by weight, of the silver oxide, and at least 0.05%, by weight, of the zinc oxide.

According to still further features in the described preferred embodiments, the formulation contains less than 25%, less than 20%, less than 15%, less than 12%, less than 10%, or less than 8%, by weight, of the zinc oxide.

According to still further features in the described preferred embodiments, a ratio of the zinc oxide to the silver oxide is at least 0.5:1, 1:1, 2:1, 3:1, or 6:1, by weight.

According to still further features in the described preferred embodiments, a ratio of the zinc oxide to the silver oxide is less than 100:1, 50:1, 20:1, 12:1, 10:1, or 8:1, by weight.

According to still further features in the described preferred embodiments, the formulation contains less than 3%, by weight, of the silver oxide.

According to still further features in the described preferred embodiments, the formulation contains at least 0.05%, at least 0.10%, at least 0.2%, or at least 0.25%, by weight, of the silver oxide.

According to still further features in the described preferred embodiments, the carrier medium includes an oleaginous material.

According to still further features in the described preferred embodiments, the oleaginous material includes a wax.

According to still further features in the described preferred embodiments, the oleaginous material includes beeswax.

According to still further features in the described preferred embodiments, the topical formulation further includes a liquid wax ester such as jojoba oil or hydrogenated jojoba oil.

According to still further features in the described preferred embodiments, the silver oxide and zinc oxide are selected, and the silver oxide and the zinc oxide are dispersed within the carrier medium, whereby a whiteness of the formulation satisfies an equation: $L^* \geq (L_0^*)+2$, wherein $L_0^*$ is a baseline whiteness value of the formulation, without the zinc oxide, and $L^*$ is a whiteness value of the formulation, including the zinc oxide.

According to still further features in the described preferred embodiments, the silver oxide, the zinc oxide, and the carrier medium are selected, and the silver oxide and the zinc oxide are dispersed within the carrier medium, whereby the whiteness value $L^*$ is at least 75, at least 78, at least 80, at least 82, or at least 84.

According to still further features in the described preferred embodiments, the content of the silver oxide is at least 0.5%, and the silver oxide, the zinc oxide, and the carrier medium are selected, and the silver oxide and the zinc oxide are dispersed within the carrier medium, whereby the whiteness value $L^*$ of the formulation is at least 80, at least 82, or at least 84.

According to still further features in the described preferred embodiments, the content of the silver oxide is at least 1.0%, and the silver oxide, the zinc oxide, and the carrier medium are selected, and the silver oxide and the zinc oxide are dispersed within the carrier medium, whereby the whiteness value $L^*$ of the formulation is at least 72, at least 75, at least 78, at least 80, at least 82, or at least 84.

According to still further features in the described preferred embodiments, the silver oxide, the zinc oxide, and the carrier medium are selected, and the silver oxide and the zinc oxide are dispersed within the carrier medium, whereby the whiteness value $L^*$ of the formulation is at least 82 or at least 84.

According to still further features in the described preferred embodiments, the carrier medium includes an aqueous phase.

According to still further features in the described preferred embodiments, the carrier medium is selected whereby the formulation is a water-based cream or lotion.

According to still further features in the described preferred embodiments, the formulation contains zinc oxide within a range of about 0.02% to about 25%, by weight, and the silver oxide largely includes a silver (II) oxide, the formulation including at least about 0.02% of the silver (II) oxide, by weight.

According to still further features in the described preferred embodiments, the formulation contains at least about 0.05% of the silver (II) oxide, and less than about 12%, less than about 10%, less than about 8%, or less than about 6% of the zinc oxide, by weight.

According to still further features in the described preferred embodiments, the formulation contains at least 0.05%, by weight, of silver(II) oxide, and the ratio of the zinc oxide to the silver(II) oxide is less than 12:1, less than 10:1, less than 8:1, or less than 6:1, by weight.

According to still further features in the described preferred embodiments, the formulation further includes any of the materials described herein, either individually or in combination with any other material, in any structure or form.

According to yet another aspect of the present invention there is provided a wound dressing including any of the topical formulations described herein.

According to still further features in the described preferred embodiments, the wound dressing includes an adhesive-containing bandage, a cotton roll bandage, or a gelable polymer.

According to yet another aspect of the present invention there is provided a method of producing a topical formulation for application to exposed body tissue, the formulation including a silver oxide and zinc oxide, intimately dispersed within a carrier medium substantially as described herein, the method including any feature described, either individually or in combination with any feature, in any configuration.

According to yet another aspect of the present invention there is provided a method of effecting a treatment of skin tissue, substantially as described herein, the method including any feature described, either individually or in combination with any feature, in any configuration.

According to further features in the described preferred embodiments, the method includes the steps of: (a) providing a formulation including: (i) a silver oxide such as a silver(II) oxide; (ii) zinc oxide, and (iii) a carrier medium, wherein the formulation contains at least 0.05%, by weight, of the silver oxide, and less than 25%, less than 20%, less than 15%, less than 12%, less than 10%, or less than 8% of the zinc oxide by weight, of the zinc oxide, and wherein the silver oxide and the zinc oxide are intimately dispersed within the carrier medium, and (b) applying the formulation to the skin tissue to effect the treatment of the skin tissue.

According to another aspect of the present invention there is provided a topical formulation for application to exposed body tissue, the formulation including: (a) a silver oxide, and (b) at least one inorganic whitener; selected from the group of inorganic whiteners consisting of an inorganic magnesium compound and an inorganic calcium compound, the silver oxide and the inorganic whitener compound intimately dispersed within a carrier medium, and wherein a ratio of the inorganic whitener compound, to the silver oxide, is at least 0.2:1, by weight, within the formulation.

According to another aspect of the present invention there is provided a topical formulation for application to exposed body tissue, the formulation including: (a) a silver oxide; and (b) at least one inorganic whitener; wherein a ratio of the inorganic whitener compound, to the silver oxide, is at least 0.2:1, by weight, within the formulation.

According to further features in the described preferred embodiments, the initial whiteness value of the formulation is at least 4 reflective units.

According to still further features in the described preferred embodiments, the whiteness value of the formulation is, initially, at least 4 reflective units, at least 4.5 reflective units, at least 5 reflective units, at least 5.5 reflective units, or at least 6 reflective units, and wherein, after constant exposure to the ultraviolet light for 3 days, the value remains at least 3.5 reflective units, at least 3.75 reflective units, at least 4 reflective units, at least 4.5 reflective units, at least 5 reflective units, or at least 5.5 reflective units.

According to still further features in the described preferred embodiments, the initial whiteness value of the formulation is at least 4 reflective units, at least 4.5 reflective units, at least 5 reflective units, at least 5.5 reflective units, or at least 6 reflective units, and wherein, after constant exposure to the ultraviolet light for 3 days, a whiteness value of the formulation remains within 1.5 reflective units, within 1.25 reflective units, or within 1.0 reflective units of the initial whiteness value.

According to still further features in the described preferred embodiments, the formulation contains at least 0.05%, at least 0.10%, at least 0.2%, at least 0.25%, at least 0.30%, at least 0.50%, at least 0.75%, or at least 1%, by weight, of the silver(I) oxide and/or silver(II) oxide.

According to still further features in the described preferred embodiments, the formulation contains less than 3%, by weight, of the silver oxide.

According to still further features in the described preferred embodiments, the whitener is further selected to act as a stabilization agent that partially inhibits a darkening of the formulation when the formulation is exposed to ultraviolet light.

According to still further features in the described preferred embodiments, the formulation has a gray or light gray hue.

According to still further features in the described preferred embodiments, the carrier medium includes an oleaginous material.

According to still further features in the described preferred embodiments, the oleaginous material includes a wax.

According to still further features in the described preferred embodiments, the oleaginous material includes beeswax.

According to still further features in the described preferred embodiments, the carrier medium includes a liquid wax ester.

According to still further features in the described preferred embodiments, the liquid wax ester includes, predominantly includes, or consists essentially of jojoba oil.

According to still further features in the described preferred embodiments, the carrier medium includes a hydrogenated liquid wax ester.

According to still further features in the described preferred embodiments, the liquid wax ester includes, predominantly includes, or consists essentially of hydrogenated jojoba oil.

According to still further features in the described preferred embodiments, the whitener is an inorganic powder.

According to still further features in the described preferred embodiments, the topical formulation further includes zinc oxide.

According to still further features in the described preferred embodiments, the whitener is further selected to act as a stabilization agent that partially inhibits a darkening of the formulation when the formulation is exposed to ultraviolet light.

According to still further features in the described preferred embodiments, the formulation contains at least 0.02%, at least 0.1%, at least 0.5%, at least 1%, at least 1.5%, at least 2%, at least 3%, at least 5%, or at least 7%, by weight, of the zinc oxide.

According to still further features in the described preferred embodiments, the formulation further includes a stabilization agent selected to partially inhibit a darkening of the formulation when exposed to ultraviolet light.

According to still further features in the described preferred embodiments, the whitener and the stabilization agent have a total concentration of at least about 0.01%, by weight, and the silver oxide has a concentration of at least about 0.01%, by weight.

According to still further features in the described preferred embodiments, the silver oxide includes, largely includes, mainly includes, predominantly includes, or consists essentially of a silver(II) oxide.

According to still further features in the described preferred embodiments, the silver oxide includes, largely includes, mainly includes, predominantly includes, or consists essentially of a silver(I) oxide.

According to still further features in the described preferred embodiments, the ratio of the stabilization agent to the zinc oxide, within the formulation, is at least 0.5:1, at least 1:1, at least 1.5:1, at least 2:1, at least 3:1, at least 5:1, or at least 7:1, by weight, the stabilization agent selected to partially inhibit a darkening of the formulation when the formulation is exposed to ultraviolet light.

According to still further features in the described preferred embodiments, the stabilization agent is selected from the group consisting of bentonite, magnesium hydroxide, calcium hydroxide, calcium carbonate, magnesium oxide, magnesium carbonate, and magnesium sulfate.

According to still further features in the described preferred embodiments, the formulation contains between 0.02% and 10% of the zinc oxide, and between 0.01% and 30% of the stabilization agent.

According to still further features in the described preferred embodiments, the inorganic whitener includes at least one inorganic whitener selected from the group consisting of magnesium oxide, magnesium hydroxide, and magnesium carbonate.

According to still further features in the described preferred embodiments, the stabilization agent includes magnesium oxide.

According to still further features in the described preferred embodiments, the formulation contains less than 0.5%, less than 0.3%, or less than 0.1% titanium dioxide, or is substantially free of the titanium dioxide.

According to still further features in the described preferred embodiments, the topical formulation further includes zinc oxide, but contains less than 0.5%, less than 0.3%, or less than 0.1% thereof, and the ratio of the stabilization agent, the whitener, and the zinc oxide, to the silver oxide, is at least 0.5:1, at least 0.75:1, at least 1:1, at least 1.5:1, at least 2:1, at least 3:1, or at least 5:1, by weight, within the formulation.

According to still further features in the described preferred embodiments, the ratio of the stabilization agent, the whitener, and the zinc oxide, to the silver oxide, is at least 0.5:1, at least 0.75:1, at least 1:1, at least 1.5:1, at least 2:1, at least 3:1, or at least 5:1, by weight, within the formulation.

According to still further features in the described preferred embodiments, the total concentration of the whitener and the stabilization agent is at least 0.01%, at least 0.05%, at least 0.1%, at least 0.5%, at least 1%, at least 2%, at least 3%, at least 5%, at least 7%, or at least 10%.

According to still further features in the described preferred embodiments, the inorganic magnesium compound is selected from the group consisting of a magnesium oxide, a magnesium carbonate, and a magnesium sulfate.

According to still further features in the described preferred embodiments, the inorganic calcium compound is selected from the group consisting of a calcium oxide, a calcium carbonate, and a calcium sulfate.

According to still further features in the described preferred embodiments, the silver oxide has a dark hue.

According to still further features in the described preferred embodiments, the silver oxide has a hue within a range of shades between gray and black.

According to still further features in the described preferred embodiments, the formulation has a hue that is lighter than the hue of the silver oxide.

According to still further features in the described preferred embodiments, the formulation has a hue that is lighter than the hue of the silver oxide, after the formulation is subject to constant exposure to ultraviolet light for at least 3 days.

According to another aspect of the present invention there is provided a solid biocompatible formulation suitable for insertion within chronic and acute wounds of humans and animals, the formulation including a topical antibiotic, a biocompatible humectant, and a biocompatible viscosity-building agent, the humectant and the viscosity-building agent intimately mixed within the formulation, which is formulated and adapted whereby the formulation remains a solid over at least an entire temperature range of 20° C. to 35° C., the solid formulation having a storage modulus (G') and a loss modulus (G"), both measured at 25° C. and within a frequency range of 0.1 Hz to 1.0 Hz, and a complex modulus (G*), defined by:

$$G^*=(G'^2+G''^2)^{1/2}$$

the formulation having at least one of the following five rheological properties:

(1) in a torque sweep at a frequency of 1.0 Hz, the complex modulus achieves a plateau or a maximum of at least $4.0\times10^4$ Pa, at least $6.0\times10^4$ Pa, at least $8.0\times10^4$ Pa, or at least $10.0\times10^4$ Pa;

(2) in the torque sweep, the complex modulus drops sharply, or begins to exhibit non-linear behavior, at an oscillating stress of at least 800 Pa, at least 900 Pa, at least 1000 Pa, at least 1200 Pa, at least 1500 Pa, or at least 2000 Pa; within the frequency range, at at least one point:

(3) the storage modulus is at least $1.0\times10^4$ Pa, at least $2.0\times10^4$ Pa, at least $3.0\times10^4$ Pa, at least $4.0\times10^4$ Pa, at least $5.0\times10^4$ Pa, or at least $6.0\times10^4$ Pa;

(4) the loss modulus is at least $0.4\times10^4$ Pa, at least $0.5\times10^4$ Pa, at least $0.6\times10^4$ Pa, at least $0.8\times10^4$ Pa, at least $1.0\times10^4$ Pa, at least $1.5\times10^4$ Pa or at least $2.0\times10^4$ Pa;

(5) the complex modulus is at least $1.05\times10^4$ Pa, at least $1.05\times10^4$ Pa, at least $2\times10^4$ Pa, at least $3.0\times10^4$ Pa, at least $4.0\times10^4$ Pa, or at least $6.0\times10^4$ Pa.

According to further features in the described preferred embodiments, the complex modulus achieves a plateau or maximum of at least $4.0\times10^4$ Pa, at least $6.0\times10^4$ Pa, at least $8.0\times10^4$ Pa, or at least $10.0\times10^4$ Pa.

According to still further features in the described preferred embodiments, the complex modulus drops sharply, or begins to exhibit non-linear behavior, at an oscillating stress of at least 800 Pa, at least 900 Pa, at least 1000 Pa, at least 1200 Pa, at least 1500 Pa, or at least 2000 Pa.

According to still further features in the described preferred embodiments, at at least one point within the frequency range, the storage modulus is less than $1.2\times10^7$ Pa, less than $1.0\times10^7$ Pa, less than $8\times10^6$ Pa, or less than $7\times10^6$ Pa.

According to still further features in the described preferred embodiments, at at least one point within the frequency range, the loss modulus is less than $5\times10^6$ Pa, less than $3\times10^6$ Pa, less than $2\times10^6$ Pa, or less than $1\times10^6$ Pa.

According to still further features in the described preferred embodiments, at at least one point within the frequency range, the complex modulus is less than $1.2\times10^7$ Pa, less than $1.0\times10^7$ Pa, less than $8\times10^6$ Pa, or less than $7\times10^6$ Pa.

According to still further features in the described preferred embodiments, at at least one point within the frequency range, a ratio of the storage modulus to the loss modulus is at least 1.5:1, at least 2.0:1, at least 2.5:1, at least 3:1, at least 4:1, or at least 5:1, and/or the ratio is less than 12:1, less than 10:1, less than 9:1, or less than 8:1.

According to still further features in the described preferred embodiments, at at least one point within the frequency range, the storage modulus is at least $3.0\times10^4$ Pa, at least $4.0\times10^4$ Pa, at least $5.0\times10^4$ Pa, or at least $6.0\times10^4$ Pa, and the loss modulus is at least $0.6\times10^4$ Pa, at least $0.8\times10^4$ Pa, at least $1.0\times10^4$ Pa, at least $1.5\times10^4$ Pa, or at least $2.0\times10^4$ Pa.

According to still further features in the described preferred embodiments, at at least one point within the frequency range, the storage modulus is at least $5.0\times10^4$ Pa, or at least $6.0\times10^4$ Pa, and the loss modulus is at least $0.8\times10^4$ Pa, at least $1.0\times10^4$ Pa, at least $1.5\times10^4$ Pa, or at least $2.0\times10^4$ Pa.

According to still further features in the described preferred embodiments, a ratio of the storage modulus to the loss modulus is at least 1.5:1, at least 2.0:1, at least 2.5:1, at least 3:1, at least 4:1, or at least 5:1, and/or the ratio is less than 12:1, less than 10:1, less than 9:1, or less than 8:1, substantially throughout the frequency range.

According to still further features in the described preferred embodiments, the storage modulus is at least $3.0\times10^4$ Pa, at least $4.0\times10^4$ Pa, at least $5.0\times10^4$ Pa, or at least $6.0\times10^4$ Pa, substantially throughout the frequency range.

According to still further features in the described preferred embodiments, the loss modulus is at least $0.6\times10^4$ Pa, at least $0.8\times10^4$ Pa, at least $1.0\times10^4$ Pa, at least $1.5\times10^4$ Pa, or at least $2.0\times10^4$ Pa, substantially throughout the frequency range.

According to still further features in the described preferred embodiments, the storage modulus is at least $5.0\times10^4$ Pa, or at least $6.0\times10^4$ Pa, substantially throughout the frequency range.

According to still further features in the described preferred embodiments, the loss modulus is at least $1.0\times10^4$ Pa, at least $1.5\times10^4$ Pa, or at least $2.0\times10^4$ Pa, substantially throughout the frequency range.

According to still further features in the described preferred embodiments, the water concentration within the formulation is at least 5%, at least 7%, at least 10%, at least 20%, at least 30%, at least 40%, at least 50%, or at least 60%.

According to still further features in the described preferred embodiments, the concentration of the antibiotic within the formulation is at least 0.1%, at least 0.2%, at least 0.4%, at least 0.7%, or at least 1%.

According to still further features in the described preferred embodiments, the antibiotic is present within the formulation in a therapeutically effective concentration for treatment of topical skin infections.

According to still further features in the described preferred embodiments, the antibiotic is selected from the group of topical antibiotics consisting of silver(II) oxide, silver(I) oxide, silver sulfadiazine, Bacitracin, Neomycin, Erythromycin and Chloramphenicol.

According to still further features in the described preferred embodiments, the humectant and the viscosity-building agent are selected, and the formulation is adapted, whereby a melting temperature of the formulation is at least 40° C., at least 45° C., at least 50° C., or at least 75° C.

According to still further features in the described preferred embodiments, the formulation is a putty at 20° C. or at 22° C., at 35° C. or at 37° C., or throughout the temperature range.

According to still further features in the described preferred embodiments, the formulation contains at least 1%, at least 1.5%, at least 2.5%, at least 3%, at least 4%, at least 7%, at least 12%, at least 20%, or at least 30% of the humectant.

According to still further features in the described preferred embodiments, the formulation contains less than about 55%, less than 50%, less than 48%, less than 45%, or less than 40%, of the humectant.

According to still further features in the described preferred embodiments, the humectant includes, largely includes, predominantly includes, or consists essentially of a liquid wax ester.

According to still further features in the described preferred embodiments, the formulation further includes an absorbefacient.

According to still further features in the described preferred embodiments, the formulation further includes an absorbefacient, wherein a combined weight content of the viscosity-building agent and the absorbefacient within the formulation is at least about 4%, at least 6%, at least 8%, at least 10%, or at least 15%.

According to still further features in the described preferred embodiments, the combined weight content is in a range of about 8% to 70%, about 8% to 65%, or about 10% to 50%.

According to still further features in the described preferred embodiments, the viscosity-building agent includes, largely includes, or consists essentially of at least one of a hydrophilic clay, a flour, and a starch.

According to still further features in the described preferred embodiments, the absorbefacient includes, largely includes, or consists essentially of at least one of a hydrophilic clay, a flour, and a starch.

According to still further features in the described preferred embodiments, the hydrophilic clay is selected from at least one of the group of hydrophilic clays consisting of a smectite, sepiolite, and palygorskite.

According to still further features in the described preferred embodiments, the smectite is selected from at least one of the group consisting of bentonite, montmorillonite and hectorite.

According to still further features in the described preferred embodiments, a weight ratio of the at least one viscosity-building agent and absorbefacient to humectant is at least 0.25:1, at least 0.4:1, at least 0.6:1, at least 1:1, and more typically, about 1.5:1 to 5:1, about 2:1 to 5:1, or about 2:1 to 4:1.

According to still further features in the described preferred embodiments, the humectant includes jojoba oil, hydrogenated jojoba oil.

According to still further features in the described preferred embodiments, the humectant includes, largely includes, or consists essentially of jojoba oil.

According to still further features in the described preferred embodiments, the formulation further includes at least 0.3%, at least 1%, at least 2.5%, or at least 4% of a skin-protecting agent.

According to still further features in the described preferred embodiments, the skin-protecting agent includes zinc oxide.

According to still further features in the described preferred embodiments, the formulation contains, by weight, less than 15%, less than 12%, or less than 10% of the skin-protecting agent.

According to still further features in the described preferred embodiments, the formulation is an elastic, moldable formulation.

According to still further features in the described preferred embodiments, the formulation is adapted whereby a plug or piece of the formulation may be fit to a contour of a wound cavity According to still further features in the described preferred embodiments, the formulation is adapted whereby a plug or piece of the formulation may be inserted into a wound cavity in an integral fashion.

According to still further features in the described preferred embodiments, the formulation is adapted wherein a plug or piece of the formulation securely holds position within a wound cavity.

According to still further features in the described preferred embodiments, the formulation and/or a plug or piece of the formulation is adapted to be removed from a wound cavity in an integral fashion.

According to still further features in the described preferred embodiments, the formulation and/or a plug or piece of the formulation is adapted to provide a gentle pressure against a surface within a wound cavity.

According to still further features in the described preferred embodiments, the formulation and/or a plug or piece of the formulation is adapted to be removed from the wound cavity in an integral fashion, after contacting the surface for at least 4 hours, at least 12 hours, or at least 24 hours.

According to yet another aspect of the present invention there is provided a formulation suitable for application to skin tissue, substantially as described herein, the formulation including any feature described, either individually or in combination with any feature, in any configuration.

According to another aspect of the present invention there is provided a method of producing a composition, formulation, or medical device, the method including any feature described, either individually or in combination with any feature, in any configuration.

According to another aspect of the present invention there is provided a method of topically applying the inventive formulation or medical device on the skin, on a wound, or within a wound cavity, the method including any feature described, either individually or in combination with any feature, in any configuration.

According to the teachings of the present invention there is provided a formulation including at least one silver oxide including a silver(II) oxide, the silver(II) oxide having an irregular macrocrystal structure, the silver oxide having an average particle size ($D_{50}$) below 8 micrometers, the irregular macrocrystal structure characterized by a diffraction peak in a {111} diffraction plane having at least one of the following structural properties: (i) a measured full width half maximum (FWHM) of the peak of at least 0.24 degrees of 2θ; and (ii) a net full width half maximum (net FWHM) of the peak of at least 0.14 degrees of 2θ.

According to another aspect of the present invention there is provided a formulation including a solid phase containing at least one silver oxide including a silver(II) oxide, the silver(II) oxide having an irregular macrocrystal structure, the silver oxide having an average particle size ($D_{50}$) below 8 micrometers, wherein the irregular macrocrystal structure is structurally characterized by a lability pattern of a thermogravimetric analysis (TGA) performed on the solid phase in a chamber, under a pure nitrogen environment and a temperature ramp rate of 10° C./minute, the lability pattern being characteristic of structural properties within the irregular macrocrystal structure, the lability pattern having at least one of the following properties: (i) a derivative of weight loss of the solid phase with respect to a temperature change in the chamber peaks at a temperature below 202° C.; and (ii) a first shoulder of the derivative appears below 165° C.

According to yet another aspect of the present invention there is provided a formulation including at least one silver oxide including a silver(II) oxide, the silver oxide having an average particle size within a range of 0.8 micrometers and 4.5 micrometers.

According to further features in the described preferred embodiments, the formulation is a topical formulation for application to skin tissue, wherein, within the topical formulation, the silver oxide is dispersed or intimately dispersed in a base material.

According to still further features in the described preferred embodiments, the silver oxide includes silver(I) oxide, and wherein a ratio of the silver(I) oxide to the silver(II) oxide is at least 0.05:1, at least 0.06:1, at least 0.07:1, at least 0.08:1, at least 0.10:1, at least 0.15:1, or at least 0.20:1, by weight.

According to still further features in the described preferred embodiments, the silver oxide has an average particle size within a range of 0.8 micrometers and 4.5 micrometers.

According to still further features in the described preferred embodiments, the silver oxide has an average particle size above 0.8 micrometers, above 0.9 micrometers, above 1.0 micrometer, above 1.2 micrometers, or above 1.5 micrometers.

According to still further features in the described preferred embodiments, the formulation contains at least 0.05%, at least 0.10%, at least 0.15%, at least 0.25%, or at least 0.50%, by weight, of the silver(II) oxide.

According to still further features in the described preferred embodiments, the silver oxide has an average particle size ($D_{50}$) below 4.5 micrometers, below 4 micrometers, below 3 micrometers, below 2.5 micrometers, or below 2.0 micrometers.

According to still further features in the described preferred embodiments, the silver oxide largely includes or predominantly includes the silver(II) oxide.

According to still further features in the described preferred embodiments, the silver(II) oxide includes, largely includes, or consists substantially of tetrasilver tetroxide.

According to still further features in the described preferred embodiments, the diffraction peak is characterized by the 2θ being within at least one of a range of 37-37.5 degrees, and a range of 37.1-37.4 degrees.

According to still further features in the described preferred embodiments, the base material includes a liquid wax ester.

According to still further features in the described preferred embodiments, the base material includes at least one wax.

According to still further features in the described preferred embodiments, the at least one wax includes a solid wax that is solid at a temperature of 20° C.

According to still further features in the described preferred embodiments, the formulation further includes a solid wax ester.

According to still further features in the described preferred embodiments, the liquid wax ester has an average carbon number of up to 46, up to 44, or up to 42.

According to still further features in the described preferred embodiments, the liquid wax ester has an average carbon number of at least 34, at least 36, or at least 38.

According to still further features in the described preferred embodiments, the liquid wax ester includes jojoba oil.

According to still further features in the described preferred embodiments, the solid wax ester includes hydrogenated jojoba oil.

According to still further features in the described preferred embodiments, the silver oxide includes a silver(I) oxide, and wherein the ratio of the silver(I) oxide to the silver(II) oxide is less than 5:1, less than 2:1, less than 1:1, less than 0.8:1, or less than 0.5:1, by weight.

According to still further features in the described preferred embodiments, the measured full width half maximum (FWHM) is at least 0.24 degrees, at least 0.25 degrees, at least 0.28 degrees, at least 0.30 degrees, at least 0.32 degrees, or at least 0.35 degrees of 2θ.

According to still further features in the described preferred embodiments, the net full width half maximum (FWHM) is at least 0.14 degrees, at least 0.15 degrees, at least 0.16 degrees, at least 0.18 degrees, at least 0.20 degrees, at least 0.22 degrees, or at least 0.25 degrees, of 2θ.

According to still further features in the described preferred embodiments, the irregular macrocrystal structure is structurally characterized by a lability pattern of a thermogravimetric analysis (TGA) performed on the solid phase in a chamber, under a pure nitrogen environment and a temperature ramp rate of 10° C./minute, and wherein a derivative of weight loss of the solid phase with respect to a temperature change in the chamber peaks at a temperature below 202° C., below 200° C., below 198° C., below 197° C., or below 195° C.

According to still further features in the described preferred embodiments, the irregular macrocrystal structure is structurally characterized by a lability pattern of a thermogravimetric analysis (TGA) performed on the solid phase in a chamber, under a pure nitrogen environment and a temperature ramp rate of 10° C./minute, and wherein a first shoulder of a derivative of weight loss of the solid phase with respect to a temperature change in the chamber appears below 165° C., below 160° C., below 155° C., or below 150° C.

According to still further features in the described preferred embodiments, the derivative peaks at a temperature below 200° C., below 198° C., below 197° C., or below 195° C.

According to still further features in the described preferred embodiments, a first shoulder of the derivative appears below 160° C., below 155° C., or below 150° C.

According to still further features in the described preferred embodiments, the carrier base includes a solid wax such as a beeswax.

According to still further features in the described preferred embodiments, the carrier base includes water.

According to further teachings of the present invention there is provided a wound dressing including any of the formulations described herein.

According to still further features in the described preferred embodiments, the wound dressing includes an adhesive-containing bandage, a cotton roll bandage, or a gelable polymer.

According to further teachings of the present invention there is provided a medical device including an ointment or oil-based cream according to any of the formulations described herein.

According to further teachings of the present invention there is provided a medical device including an emulsion according to any of the formulations described herein.

According to further teachings of the present invention there is provided a medical device including a water-based cream according to any of the formulations described herein.

According to yet another aspect of the present invention there is provided a method including the steps of: (a) providing a formulation, medical device, or wound dressing, including any of those recited by of any one of the above claims, and (b) applying the composition, formulation, medical device, or wound dressing to skin tissue.

According to yet another aspect of the present invention there is provided a method including (a) providing a formulation including at least one silver oxide including a silver(II) oxide, the at least one silver oxide having an average particle size ($D_{50}$) within a range of from above 0.8 micrometers to below 8 micrometers, the silver(II) oxide having an irregular macrocrystal structure, the irregular macrocrystal structure characterized by a diffraction peak in a {111} diffraction plane, the diffraction peak having at least one of the following structural properties: (i) a measured full width half maximum (FWHM) of at least 0.30 degrees of 2θ and not more than 0.466 degrees of 2θ; and (ii) a net full width half maximum (net FWHM) of at least 0.20 degrees of 2θ and not more than 0.366 degrees of 2θ; the formulation being a topical formulation suitable for application to skin tissue, wherein the silver oxide predominantly includes the silver(II) oxide; and (b) applying the formulation to skin tissue.

According to yet another aspect of the present invention there is provided a method including (a) providing a silver oxide raw material, the silver oxide raw material predominantly including a silver(II) oxide; (b) milling the silver oxide raw material in a vortex mill, to produce a silver oxide powder in which an average particle size is smaller by at least one micrometer an average particle size of silver oxide raw material; wherein the silver oxide powder contains a silver(I) oxide and the silver(II) oxide, and wherein a concentration of the silver(I) oxide in the silver oxide powder exceeds a concentration of the silver(I) oxide in the silver oxide raw material.

According to still further features in the described preferred embodiments, the formulation, medical device, or wound dressing is applied to the skin tissue to effect a treatment of the skin tissue.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like elements.

In the drawings:

FIGS. 5A, 5B, 5C, 5D and 5E provide top view photographs of Petri dishes containing oil-based formulations and identically grown cultures according to a modified pour plate method, wherein:

FIG. 5A shows a cultured Petri dish after being exposed to a formulation containing 1.0% AgO and 7.0% ZnO;

FIG. 5B shows a cultured Petri dish after being exposed to a formulation containing 1.0% AgO and no ZnO;

FIG. 5C shows a cultured Petri dish after being exposed to a formulation containing 7.0% ZnO and no AgO;

FIG. 5D shows a cultured Petri dish after being exposed to a formulation containing 1.0% AgO and 14.0% ZnO;

FIG. 5E shows a cultured Petri dish after being exposed to a formulation containing 0.84% AgO and 28.0% ZnO;

DESCRIPTION OF THE PREFERRED EMBODIMENTS

Figure 1:
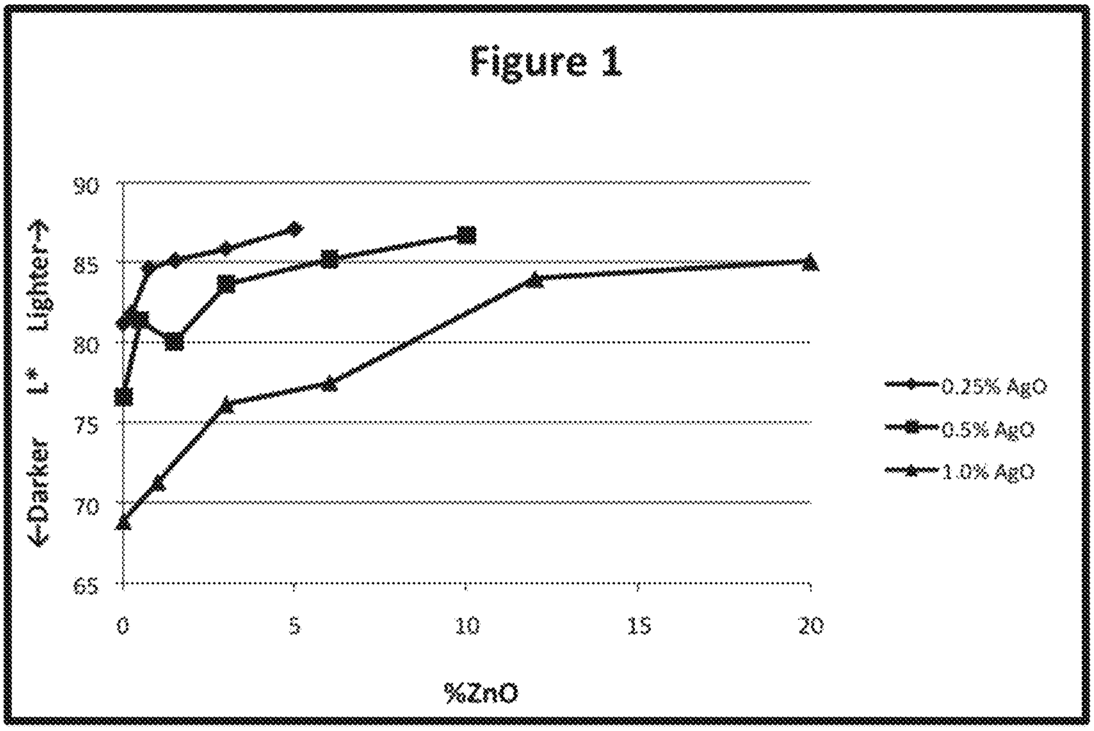
FIG. 1 is a graph plotting whiteness of cloth swatches stained with formulations containing varying concentrations zinc oxide and silver(II) oxide, as a function of the weight content of zinc oxide within the formulations.

Before explaining at least one embodiment of the invention in detail, it is to be understood that the invention is not limited in its application to the details of construction and the arrangement of the components set forth in the following description. The invention may be capable of other embodiments or of being practiced or carried out in various ways. Also, it is to be understood that the phraseology and terminology employed herein is for the purpose of description and should not be regarded as limiting.

The medical device of the present invention contains both a silver oxide compound and zinc oxide, preferably in a carrier medium that may be a water-based cream or lotion, or an ointment that may include a wax and/or an oil. The formulation may include an emulsion, or be substantially emulsion-based.

The inventive silver oxide based medical device may have a generally white appearance. At lower ratios of whitening agent to silver oxide, the appearance of the medical device may be off-white or grayish.

We have found that silver(II) oxide, despite being an extremely reactive material, does not deleteriously interact with zinc oxide within the formulation. We have also found that the zinc oxide does not appear to reduce or appreciably reduce the anti-microbial efficacy of the silver(II) oxide. This appears to be particularly surprising, because zinc oxide is used in various coating applications, and might be expected to cover or block the silver(II) oxide particles, thereby reducing the contact between the silver(II) oxide particles and the microorganisms.

Moreover, we have surprisingly discovered that within a specified range of weight ratios and/or compositions, the silver oxide based formulation is highly spreadable, despite the presence of the chalky zinc oxide. We have found that silver oxide-zinc oxide formulations containing more than 25% zinc oxide, by weight, may display poor spreadability, and may also be less efficacious from an anti-microbial standpoint. In some formulations, a zinc oxide content of more than 20%, by weight, may exhibit such deleterious properties.

We have found that for formulations within a particular range of zinc oxide to silver oxide weight ratios, or having a particular range of zinc oxide and silver oxide contents, the zinc oxide acts to appreciably whiten the inventive formulations. However, above this particular range of zinc oxide to silver oxide weight ratios, or above a particular amount of zinc oxide, the whitening effect of the zinc oxide may become substantially insignificant.

Whiter formulations tend to be more aesthetically pleasing, and it would appear that such whiter formulations would tend to promote less staining of fabric such as clothes. However, we have surprisingly found that when formulations containing zinc oxide mixed with a silver oxide (such as a silver(II) oxide) are disposed on a fabric, conventional laundering of the fabric yields stains having a lightness that may not monotonically correlate with the lightness of the initial stain, prior to the laundering.

With reference now to FIG. 1, FIG. 1 is a graph plotting formulation whiteness or luminance (expressed as L*) as a function of zinc oxide concentration (in weight percent) within the formulation. The whiteness parameter L* has been specified by the International Commission on Illumination (Commission Internationale d'Eclairage, or CIE) to achieve perceptual uniformity, and the L* component thereof has been determined to closely match human perception of lightness. Regarding the scale of L*, the luminance is expressed as a percentage, wherein L*=0 represents black, and L*=100 represents diffuse white.

In FIG. 1, formulations containing three concentrations of silver(II) oxide were tested: 0.25%, 0.5%, and 1%, by weight, respectively. As may be seen from the data in Table 1 and from FIG. 1, the formulation whiteness (L*) increases substantially monotonically with increasing concentration of zinc oxide. However, appreciable differential increases in the formulation whiteness (L*) are typically obtained when the zinc oxide concentration is less than about 12%, less than about 10%, less than about 8%, or less than about 6% zinc oxide, by weight.

TABLE 1

| 0.25% silver(II) oxide | | 0.5% silver(II) oxide | | 1% silver(II) oxide | |
|---|---|---|---|---|---|
| % zinc oxide | L* | % zinc oxide | L* | % zinc oxide | L* |
| 0 | 81.16 | 0 | 76.62 | 0 | 68.89 |
| 0.25 | 81.81 | 0.5 | 81.39 | 1 | 71.34 |
| 0.75 | 84.58 | 1.5 | 80.04 | 3 | 76.20 |
| 1.5 | 85.11 | 3 | 83.65 | 6 | 77.51 |
| 3 | 85.84 | 6 | 85.17 | 12 | 83.98 |
| 5 | 87.12 | 10 | 86.73 | 20 | 85.09 |

Figure 2:
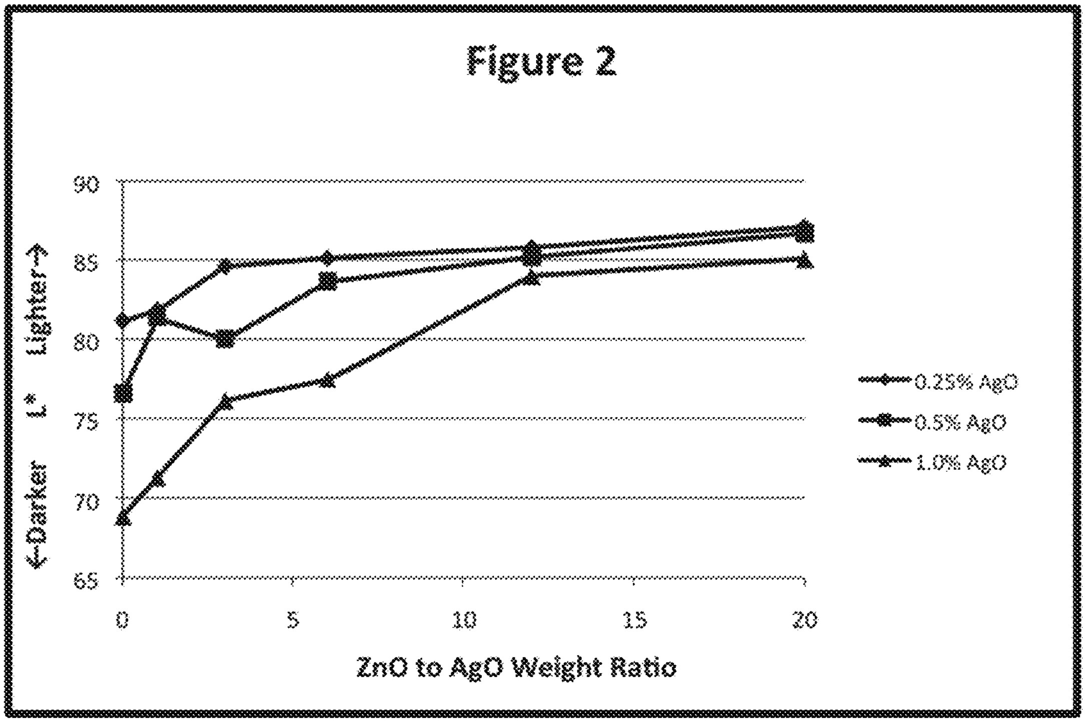
FIG. 2 is a graph plotting whiteness of the cloth swatches as a function of the weight ratio of zinc oxide to silver(II) oxide within each of the above formulations.

FIG. 2 is a graph plotting formulation whiteness (expressed as L*) as a function of the weight ratio of zinc oxide to silver(II) oxide within each formulation.

As may be seen from the data in Table 2 and from FIG. 2, the formulation whiteness (L*) increases substantially monotonically with increasing ratio of zinc oxide to silver (II) oxide. However, appreciable differential increases in the formulation whiteness (L*) are typically obtained when the ratio of zinc oxide to silver(II) oxide within the formulation is less than about 15:1, less than about 12:1, less than about 10:1, less than about 8:1, or less than about 6:1. Below a ratio of about 20:1, the differential increase in the formulation whiteness is less substantial.

We have surprisingly found that when formulations containing zinc oxide mixed with a silver oxide (such as a silver(II) oxide) are disposed on a fabric, conventional laundering of the fabric yields stains that may not monotonically correlate with the lightness of the initial stain, prior to the laundering. Table 3 provides whiteness (L*) as a function of concentration of zinc oxide, for a white fabric impregnated with the formulations provided in Table 1, after the fabric has undergone a staining and laundering procedure.

TABLE 2

| 0.25% silver(II) oxide | | 0.5% silver(II) oxide | | 1% silver(II) oxide | |
|---|---|---|---|---|---|
| ratio of ZnO to silver(II) oxide | L* | ratio of ZnO to silver(II) oxide | L* | ratio of ZnO to silver(II) oxide | L* |
| 0 | 81.16 | 0 | 76.62 | 0 | 68.89 |
| 0.25 | 81.81 | 0.5 | 81.39 | 1 | 71.34 |
| 0.75 | 84.58 | 1.5 | 80.04 | 3 | 76.20 |
| 1.5 | 85.11 | 3 | 83.65 | 6 | 77.51 |
| 3 | 85.84 | 6 | 85.17 | 12 | 83.98 |
| 5 | 87.12 | 10 | 86.73 | 20 | 85.09 |

The following procedure was used:

Cut a 7×7 cm piece of fabric from a white cotton T-shirt to produce a cloth swatch;

1. Weigh the cloth swatch;
2. Place cloth swatch on a clean paper towel to absorb any extraneous oil from the staining procedure;
3. Apply 400 mg of staining sample to the back of spatula;
4. Spread sample evenly over 90% of cloth surface using spatula, taking care
   a. not to stain edges, and
   b. to use the entire staining sample;
5. Re-weigh cloth swatch to insure complete transfer of the sample (typically weighs an additional ~400 mg);
6. Allow the cloth to absorb the sample for 24 hours in an open air environment at room temperature (65-75° F.);
7. Place cloth in 650-700 ml of warm detergent/water solution (regular tap water and Lestoil® brand detergent/stain remover or similar);
   a. Solution is prepared using 10 ml of detergent for every liter of water;
   b. Solution is drawn anew from a stock solution for each sample;
   c. Stock solution is warmed to ~130° F.;
8. Mix cloth-containing solution for 10 minutes using mixer operating at 300 rpm;
9. Rinse cloth by placing in beaker of clean water. Remove cloth, and repeat rinsing procedure for a total of three rinses, each time using new clean water;
10. Pin swatches to uniform flat wall;
   a. Pin only the unstained edges;
   b. Place in open air environment;
   c. Maintain swatches at room temperature (65-75° F.); and
11. Store swatches in a lightproof pouch until ready to measure with colorimetric instrument.

The whiteness of the various samples was measured using a Color Cue® 2.1 colorimetric instrument (Pantone, Inc.). A clear plastic wrap was placed over each sample. The colorimeter was then lightly pressed onto the wrap and the color was recorded. The L* reading was used to indicate the relative lightness of the stain with respect to other samples. Readings were recorded from 3 separate areas on the cloth sample, and the obtained values were averaged.

The formulations used in the staining and laundering procedure contained three concentrations of silver(II) oxide: 0.25%, 0.5%, and 1%, by weight, as described with respect to Table 1 hereinabove. With reference now to the values provided in Table 3, and plotted in FIG. 3, it is observed that at low zinc oxide content, the whiteness (L*) of the laundered cloth swatches increases with increasing concentration of zinc oxide. However, at each of the three concentrations of silver oxide, a maximum whiteness is observed at zinc oxide contents of about 0.75%, 1.5%, and 6%, respectively. Above these values, the whiteness (L*) of the laundered cloth swatches levels off, or may even decrease somewhat with increasing concentration of zinc oxide.

The presently preferred zinc oxide content in the formulations of the present invention may be heavily dependent on the silver oxide content within the formulation, which may be at least 0.05%, at least 0.1%, at least 0.25%, at least 0.5%, at least 0.75%, at least 1%, or at least 3%, by weight. However, the preferred zinc oxide content may depend upon the particular composition of the formulation, upon the composition of the base material(s), and upon other formulation characteristics. Generally, however, the presently preferred zinc oxide content in the formulations of the present invention may be at least 0.5%, at least 0.75%, at least 1%, or at least 3%, by weight. The presently preferred zinc oxide content in the formulations of the present invention may be less than 20%, by weight, and more typically, less than about 12%, less than about 10%, less than about 8% zinc oxide, or less than about 6% zinc oxide.

TABLE 3

| 0.25% silver(II) oxide | | 0.5% silver(II) oxide | | 1% silver(II) oxide | |
|---|---|---|---|---|---|
| % zinc oxide | L* | % zinc oxide | L* | % zinc oxide | L* |
| 0 | 84.38 | 0 | 80.52 | 0 | 71.39 |
| 0.25 | 86.96 | 0.5 | 83.31 | 1 | 73.81 |
| 0.75 | 87.66 | 1.5 | 83.96 | 3 | 74.85 |
| 1.5 | 87.18 | 3 | 83.19 | 6 | 77.38 |
| 3 | 86.67 | 6 | 83.73 | 12 | 77.17 |
| 5 | 86.95 | 10 | 83.22 | 20 | 75.64 |

Figure 4:
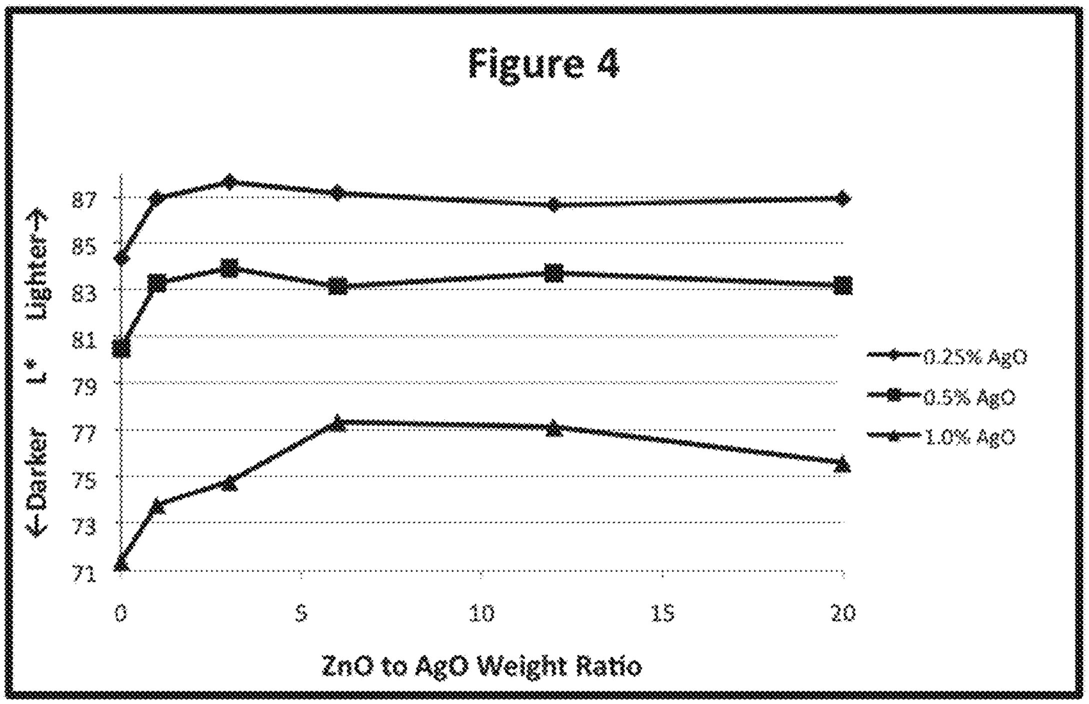
FIG. 4 is a graph plotting whiteness of the laundered cloth swatches as a function of the weight ratio of zinc oxide to silver(II) oxide within the staining formulations initially applied to the swatches.
Figure 5A:
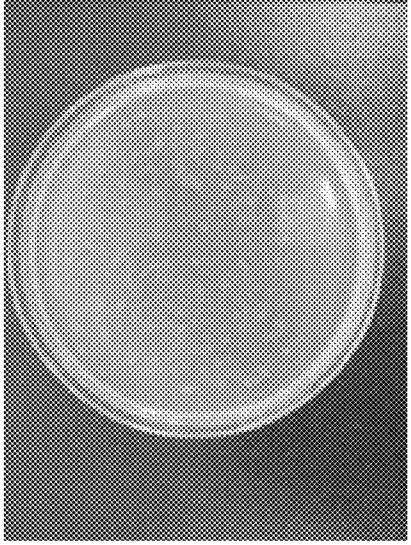
Figure 5B:
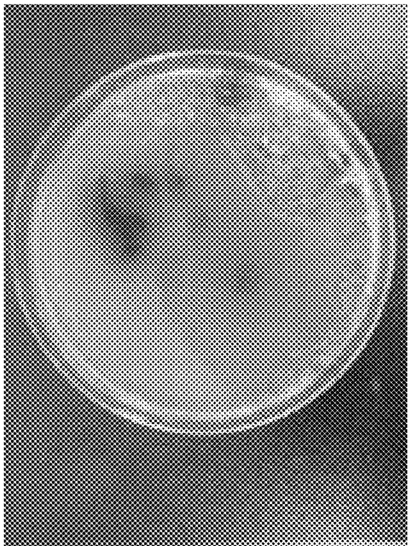
Figure 5C:
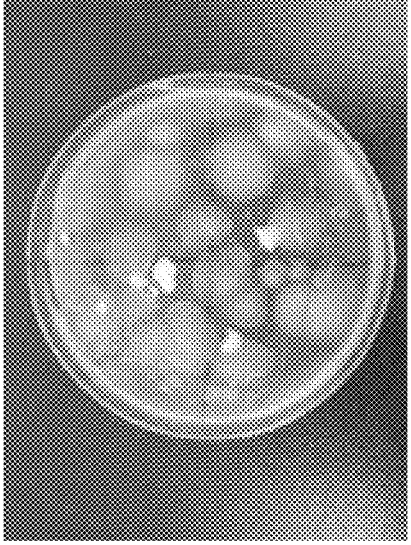
Figure 5D:
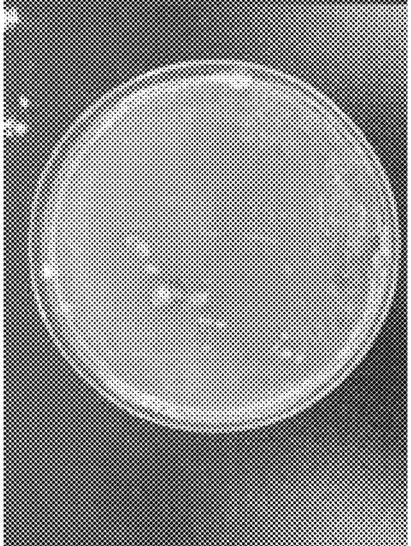
Figure 5E:

FIG. 4 is a graph plotting formula whiteness (expressed as L*) as a function of the weight ratio of zinc oxide to silver(II) oxide within each formulation used in the staining and laundering procedure described hereinabove. As may be seen from FIG. 4 and the corresponding data in Table 4, the formulation whiteness (L*) generally increases appreciably with increasing ratio of zinc oxide to silver(II) oxide, at low weight ratios of zinc oxide to silver(II) oxide. Surprisingly, however, above a weight ratio of zinc oxide to silver(II) oxide of 1:1, 3:1, 5:1, or 6:1, the formulation whiteness generally increases only marginally, or fails to increase, with increasing ratio of zinc oxide to silver(II) oxide. Indeed, above a weight ratio of zinc oxide to silver(II) oxide of 8:1, 10:1, or perhaps most clearly, 12:1, the formulation whiteness may be substantially constant, or may even decrease with increasing ratio of zinc oxide to silver(II) oxide.

TABLE 4

| 0.25% silver(II) oxide | | 0.5% silver(II) oxide | | 1% silver(II) oxide | |
|---|---|---|---|---|---|
| ratio of ZnO to silver(II) oxide | L* | ratio of ZnO to silver(II) oxide | L* | ratio of ZnO to silver(II) oxide | L* |
| 0 | 84.38 | 0 | 80.52 | 0 | 71.39 |
| 1 | 86.96 | 1 | 83.31 | 1 | 73.81 |
| 3 | 87.66 | 3 | 83.96 | 3 | 74.85 |
| 6 | 87.18 | 6 | 83.19 | 6 | 77.38 |
| 12 | 86.67 | 12 | 83.73 | 12 | 77.17 |
| 20 | 86.95 | 20 | 83.22 | 20 | 75.64 |

Thus, the general appearance of the curve of the stained and laundered samples does not parallel or closely follow the general appearance of the curve of the stained samples. Moreover, at high zinc oxide contents or zinc oxide to silver(II) oxide ratios, the formulation whiteness appears to decrease with increasing zinc oxide content or ratio, instead of continuing to increase, as in the stained samples. Without wishing to be limited by theory, I attribute this to the tendency of the zinc oxide particles to adhere to the fabric, compounded by the tendency of the silver(II) oxide particles to adhere to, or otherwise associate with, the zinc oxide particles. Even so, the zinc oxide does not appear to reduce or appreciably reduce the anti-microbial efficacy of the silver(II) oxide.

An exemplary general procedure for producing the inventive silver oxide based cream is as follows: a liquid wax ester such as jojoba oil or hydrogenated jojoba oil is heated, preferably to around 80° C. A wax such as beeswax is preferably melted into the liquid wax ester. The material is mixed thoroughly as it is cooled below about 60° C. An essential oil such as palmarosa oil may be added. Mixing is continued as zinc oxide is introduced along with a silver oxide such as a silver (II) oxide or a silver (I) oxide, and the mixing may be continued during cooling of the mixture to below about 40° C. The mixing may advantageously produce an intimately dispersed formulation in which the silver oxide and/or the zinc oxide may be distributed in a homogeneous or substantially homogeneous fashion within the carrier medium.

Typically, the formulations contain 0.05% to 3% silver oxide, by weight, and more typically, 0.1% to 3% silver oxide. The formulations also contain 1% to 22% zinc oxide, by weight, and more typically, 1% to 20% zinc oxide.

EXAMPLES

Reference is now made to the following examples, which together with the above description, illustrate the invention in a non-limiting fashion.

Example 1

The exemplary silver oxide-zinc oxide formulations provided hereinbelow were prepared according to the following general procedure: jojoba oil is heated to 80° C. A wax such as beeswax may then be introduced. The material is mixed thoroughly as it is cooled to about 55° C. Palmarosa oil is added, followed by silver (II) oxide and zinc oxide. Mixing may be maintained throughout, and during cooling of the mixture to 35° C.-40° C.

In these exemplary formulations, the weight ratio of the liquid wax ester to beeswax is about 3.5 to 1. The palmarosa oil content is about 0.07% of the jojoba oil content.

Examples 2-13

Using the general procedure provided in Example 1, various silver oxide-zinc oxide formulations were prepared. Some of the specific formulations are provided below, by way of example, in Table 5. Formulations that have not been provided below produced qualitatively similar results. The percentages of silver oxide and zinc oxide are by weight, based on the total weight of the final product.

Visual whiteness evaluations were performed on each of the samples, using the scale provided in Table 6.

Example 14

The exemplary silver oxide-zinc oxide formulations provided hereinbelow were prepared according to the following general procedure: to a container containing water is added a viscosity-building agent, typically a smectite (e.g., a bentonite or montmorillonite powder such as Gelwhite H, produced by Southern Clay Products, Inc., Gonzales, Tex.). Other viscosity-building clays, particularly clays in which the silicate layers are disposed in a sandwiched structure, may also be used. Other viscosity-building agents and thickeners may be used, e.g., glycerin and carbomers. Preferably, such selected materials may exhibit good resistance to oxidation or chemical attack by the highly reactive silver(II) oxide.

The mixture is mixed or homogenized, typically for 0.5 to 2 hours. Silver(II) oxide may be introduced at this stage of the processing. Zinc oxide may be introduced to the mixture, typically along with the silver(II) oxide, or sometime therebefore or thereafter. The oil and/or liquid wax ester (e.g., jojoba oil) may be introduced to the mixture during the mixing (e.g., blending or homogenizing).

TABLE 5

| | Silver Oxide | Zinc Oxide | Wt. Ratio | Whiteness | Spreadability |
|---|---|---|---|---|---|
| Example 2 | 1.00% | 3.00% | 1 to 3 | 4 | Excellent |
| Example 3 | 0.50% | 3.00% | 1 to 6 | 6 | Excellent |
| Example 4 | 0.25% | 3.00% | 1 to 12 | 8 | Excellent |
| Example 5 | 1.00% | 7.00% | 1 to 7 | 6 | Excellent |
| Example 6 | 0.50% | 7.00% | 1 to 14 | 7 | Excellent |
| Example 7 | 0.25% | 7.00% | 1 to 28 | 8 | Excellent |
| Example 8 | 1.00% | 12.00% | 1 to 12 | 8 | Good |
| Example 9 | 0.50% | 12.00% | 1 to 24 | 9 | Good |
| Example 10 | 0.25% | 12.00% | 1 to 48 | 10 | Good |
| Example 11 | 1.00% | 20.00% | 1 to 20 | 8 | Less Good |
| Example 12 | 0.50% | 20.00% | 1 to 40 | 10 | Less Good |
| Example 13 | 0.25% | 20.00% | 1 to 80 | 10 | Less Good |

TABLE 6

| 1 | 2 | 3 | 4 | 5 | 6 | 7 | 8 | 9 | 10 |
|---|---|---|---|---|---|---|---|---|---|
| Charcoal/ black gray | Very dark gray | Dark gray | Slightly dark gray | Gray | Light gray | Slightly gray | Off white | White | Very white |

Mixing may be continued as the silver(II) oxide is introduced, and further mixing may ensue, typically for 5-30 minutes. The mixing may advantageously produce an intimately dispersed formulation in which the silver oxide and/or the zinc oxide may be distributed in a homogeneous or substantially homogeneous fashion within the carrier medium. The formulation may then be poured into storage containers.

Example 15

Using the general procedure provided in Example 14, a water-based silver(II) oxide-zinc oxide formulation was prepared. The formulation included:

| | | |
|---|---|---|
| water: | 600 grams | (87.1%) |
| bentonite: | 25 grams | (3.6%) |
| jojoba oil: | 15 grams | (2.2%) |
| zinc oxide: | 40 grams | (5.8%) |
| silver(II) oxide: | 9 grams | (1.3%) |

Example 16

Using the general procedure provided in Example 14, an emulsion-based silver(II) oxide-zinc oxide formulation was prepared. The formulation included:

| | | |
|---|---|---|
| water: | 600 grams | (63.1%) |
| bentonite: | 60 grams | (6.3%) |
| jojoba oil: | 240 grams | (25.2%) |
| zinc oxide: | 50 grams | (5.3%) |
| silver(II) oxide | 0.9 grams | (0.1%) |

Example 17

A control group of thirty patients was treated at Irvine3 Circulation/Vascular Labs (Chieti-Pescara University, Pescara, Italy) using conventional cleaning and compression management methods.

The ulcerations of the patients were diagnosed as resulting from reduced arterial pressure (above-necrosis limits with average skin perfusion pressure>50 mmHg) and diabetic microangiopathy, and were characterized by localized infection.

Color duplex scanning was used to exclude venous thrombosis, severe arterial obstruction, and Doppler techniques were used to evaluate the presence of tibial pulses, to exclude patients with severe ischemia and necrosis.

The study of the microcirculation was used to quantify microangiopathy and to follow up subjects after local treatment. Laser Doppler Flowmetry (LDF) was used to assess skin perfusion in association with transcutaneous oxygen (PO2) measurements.

Example 18

The efficacy of an ointment containing silver tetroxide (AgO) applied onto the skin surrounding the ulceration was tested at the Irvine3 Circulation/Vascular Labs on a treatment group of 29 patients, having comparable ulcerations to those of the control group of Example 17.

The ointment, containing approximately 1% AgO was applied around and at the edge of the ulcerated areas (maximum diameter ranging between 2 cm and 1.1 cm) and on the ulceration, after cleaning, three times daily. The cream was applied after careful washing for 2 minutes in water at 40° C. with a sodium hypochlorite based disinfectant (Amuchina®, Angelini Group, Italy) of the ulceration and surrounding area. A neutral adsorbing paper bandage—in contact with the skin—was applied under a skin protecting/saving foam layer. An adhesive bandage or an elastic stocking was used to cover the ulcerated area during the observation period.

Over the course of the 4-week treatment period, treatment with the AgO ointment was found to be more effective than the wound care used in the controls. The skin PO2 was increased (28%), and LDF (abnormally increased around the ulcerated areas) was decreased (median 29%). Flux increase is generally associated with severe microangiopathy. The venoarteriolar response of the area was significantly reduced (<30%) at inclusion and improved at the end of the four weeks in the treatment group (+16%).

The ulcer areas were significantly smaller at 4 weeks (the maximum diameter range was between 0.23 cm and 0; $p<0.05$) in the AgO-treated group with complete closure in 39% of subjects, vs. 16% in the controls ($p<0.05$).

Example 19

The efficacy of a silver tetroxide-zinc oxide (AgO—ZnO) ointment on skin ulcers was tested at the Irvine3 Circulation/Vascular Labs on a treatment group of 18 patients, versus a control group having 23 comparable patients. All patients underwent basic wound care treatment including conventional cleaning and compression management methods.

The ointment, containing 0.99% AgO and 5.0% ZnO in a beeswax and jojoba oil base, was applied around and at the edge of the ulcerated areas (maximum diameter ranging between 2-3 cm and 0.4 cm) and on the ulceration, after cleaning, twice daily. A neutral adsorbing paper bandage—in contact with the skin—was applied under a skin protecting/saving foam layer. An adhesive bandage or an elastic stocking was used to cover the ulcerated area during the observation period.

Over the course of the 3-week treatment period, treatment with the AgO—ZnO ointment was found to be more effective than the wound care used in the controls. Moreover, the AgO—ZnO ointment was found to be more effective than a similar ointment containing a comparable concentration of AgO, but no ZnO. The AgO—ZnO ointment was found to improve the microcirculation and healing rate in both venous ulcerations and diabetic ulcerations.

Example 20

The efficacy of a silver tetroxide-zinc oxide (AgO—ZnO) ointment on venous skin ulcers was tested at the Irvine3 Circulation/Vascular Labs on a treatment group of 44 patients, versus a control group having 38 comparable patients. All patients underwent basic wound care treatment including conventional cleaning and compression management methods.

The ointment, containing 0.87% AgO and 6.8% ZnO in a beeswax and jojoba oil base, was applied, twice daily, around and at the edge of the ulcerated areas, after cleaning.

After 4 weeks, the silver tetroxide-zinc oxide treatment proved more effective than the control group treatment: skin PO2 was increased 2.1 times more than the control group (17.4% to 8.2%) and skin flux (RF) was improved 1.6 times with respect to the control group (−38.7% to −24.2%). The total surface area of the ulcer was reduced in the silver treatment group by 88.7%, as opposed to 46.9% in the control group. In addition, in the treatment group, complete closure of the ulceration was observed in 42% of subjects compared to 22% in the control group.

Example 21

The efficacy of the AgO—ZnO ointment of Example 20 on diabetic ulcerations was tested at the Irvine3 Circulation/Vascular Labs on a treatment group of 34 patients, versus a control group having 32 comparable patients. All patients underwent basic wound care treatment including conventional cleaning and compression management methods.

The ointment was applied, twice daily, around and at the edge of the ulcerated areas, after cleaning.

After 4 weeks, the silver tetroxide-zinc oxide treatment proved more effective than the control group treatment: skin PO2 was increased 2.6 times more than the control group (23.3% to 9.1%) and skin flux (RF) was improved 4.3 times with respect to the control group (−26.7% to −6.2%). The total surface area of the diabetic ulcerations was reduced in the silver treatment group by 89.0%, as opposed to 23.9% in the control group. In addition, in the treatment group, complete closure of the ulceration was observed in 39% of subjects compared to 16% in the control group.

Example 22

The anti-microbial efficacy of various formulations was tested and compared using the following colony counting method:

A freshly opened Muller-Hinton nutrient broth (liquid medium) was inoculated using a loop full of bacteria (around 100,000-150,000 count). The sample is allowed to rest for 24 hours in the incubator at 37° C. Once the broth is turbid, another full loop is added to several tubes of nutrient broth, and the broth is allowed to sit for 10 minutes.

A known quantity of each tested formulation is applied onto respective sterile blank antibiotic discs. After adding one disc to each one of the tubes, the tubes are swirled and allowed to incubate for 24 hours in an incubator at 37° C.

Once the turbidity (bacterial growth) has been achieved after 24 hours, a loop full of each culture is streaked onto a Muller-Hinton agar plate using the streak plate ("zigzag") method. The use of a standard loop ensures that the same amount of culture is delivered to each plate. The plates are allowed to mature in an incubator for 24 hours at 37° C.

After 24 hours, the colonies are counted by means of two techniques:

- a manual technique in which a number of 100 is assigned to the control sample, and based on the density of the colonies in the other samples, a relative number is assigned based upon visual evaluation.
- an automatic colony counter (WU-14025-00 Flash & Grow Colony Counter, Cole-Palmer®, Vernon Hills, Ill.), which counts the colonies and is accurate up to 99%.

Examples 23-27

The anti-microbial efficacy of various formulations was tested and compared using the procedure detailed in Example 22, using Enterococcus faecalis (ATCC 29212) and water-based formulations containing water, bentonite and jojoba oil. The results are provided below, in Table 7:

TABLE 7

| SAMPLE/ EXAMPLE NO. | SAMPLE TYPE | COMPOSITION % AgO | % ZnO | NUMBER OF COLONIES COLONY COUNTER | VISUAL METHOD |
|---|---|---|---|---|---|
| Nutrient Broth | blank | — | — | 0 | 0 |
| *E. Faecalis* | control | — | — | 10254 | 100 |
| 23 | silver oxide-zinc oxide | 1.3 | 5.8 | 0 | 0 |
| 24 | silver oxide | 1.4 | — | 0 | 0 |
| 25 | zinc oxide | — | 5.9 | 122 | 2 |
| 26 | silver oxide-zinc oxide | 1.2 | 11.0 | 0 | 0 |
| 27 | silver oxide-zinc oxide | 1.1 | 19.8 | 0 | 0 |

Examples 28-32

The anti-microbial efficacy of various formulations was tested and compared using the procedure detailed in Example 22, using Enterococcus faecalis (ATCC 29212) and oil-based formulations containing beeswax and jojoba oil. The results are provided below, in Table 8:

TABLE 8

| SAMPLE/ EXAMPLE NO. | SAMPLE TYPE | COMPOSITION % AgO | % ZnO | NUMBER OF COLONIES COLONY COUNTER | VISUAL METHOD |
|---|---|---|---|---|---|
| Nutrient Broth | blank | — | — | 0 | 0 |
| *E. Faecalis* | control | — | — | 10254 | 100 |
| 28 | silver oxide-zinc oxide | 1.0 | 7.0 | 2755 | 20 |
| 29 | silver oxide | 1.0 | — | 7327 | 70 |
| 30 | zinc oxide | — | 7.0 | 14559 | 120 |
| 31 | silver oxide-zinc oxide | 1.0 | 14.0 | N/A* | 180 |
| 32 | silver oxide-zinc oxide | 0.84 | 28.0 | N/A* | 250 |

*too thick for quantitative measurement by colony counter a mixture of silver(II) oxide and silver(I) oxide may be appreciably more ilver(II) oxide (Sample 30) is not particularly effective in reducing the number of colonies, and in fact, a large increase in the number of colonies is observed. It is further evident that while silver(II) oxide alone displays some efficacy in reducing the number of colonies (Sample 29), that efficacy is greatly enhanced in Sample 28, a formulation containing zinc oxide and silver(II) oxide in a 7:1 weight ratio. In the formulations (Samples 31 and 32) containing higher ratios of zinc oxide to silver(II) oxide (about 14:1 to about 33:1), the number of colonies increased greatly, to the point that the number could not be measured by the colony counter.

Example 33

The anti-microbial efficacy of various formulations was tested and compared using a modified pour plate method. The bacterial population of a suspension of each test organism was prepared and determined as follows:

Inoculate the surface of a suitable volume of solid agar medium from a recently revived stock culture of each of the specified microorganisms.

Invert and incubate at 37° C. for 24-48 hours.

Harvest the bacterial cultures, use sterile saline TS or Phosphate Buffer Solution (PBS), wash the surface growth, effect collection in a suitable vessel (e.g., a test tube), and add sufficient sterile saline TS or PBS to obtain a microbial count of about $1\times10^8$ colony-forming units per mL (cfu/ml), which is approximately a McFarland Standard No. 1.0 or visible light transmittance of 47-50% at a wavelength of 580 nm.

Measure the suspension concentration by means of a spectrophotometer and adjust the concentration as needed.

Verify the bacterial population of the inoculum:

Add 9 ml of sterile PBS to each of 8 sterile test tubes using sterile pipettes and bulbs. The tubes are kept closed when not in use to prevent contamination.

Withdraw 1 ml (1000 microliters) from the original culture and add to a first ($10^4$) tube, mixing so that the bacteria are completely suspended therein. Withdraw 1 ml from the first tube and add to a second ($10^{-2}$) tube, mixing as above. Withdraw 1 ml from the second tube and add to a third ($10^{-3}$) tube, mixing as above. Withdraw 1 ml from the third tube and add to a fourth ($10^{-4}$) tube, mixing as above. Withdraw 1 ml from the fourth tube and add to a fifth ($10^{-5}$) tube, mixing as above. Withdraw 1 ml from the fifth tube and add to a sixth ($10^{-6}$) tube, mixing as above. Withdraw 1 ml from the sixth tube and add to a seventh ($10^{-7}$) tube, mixing as above. Withdraw 1 ml from the seventh tube and add to an eighth ($10^{-8}$) tube, mixing as above.

Prepare plates from the serial dilutions as follows:

Dispense 1 ml from the fourth tube onto the surface of the agar and spread the sample over the entire surface using a sterile cell spreader (L-shaped glass rod). To sterilize the cell spreader, dip in ethanol in plate and flame only to burn off the alcohol. Repeat this procedure for two additional plates, by dispensing 1 ml from each of the sixth tube and the eighth tube into respective plates. Allow plates to dry for 5 minutes before inverting for incubation for 24-48 hours at 37° C.

Record the colony counts and calculations as follows:

Identify two plates of the same dilution, having between 30 and 300 colonies. Count the number of bacterial colonies (regardless of size) on that plate, record the results, and calculate the average count. Calculate the approximate number of organisms in the original culture using the average counts in the selected dilution plates.

Pour 20 ml Tryptic Soy Agar (TSA) into each Petri dish (100×15 mm). In a suitable flask or bottle, weigh the desired amount of the dehydrated agar and achieve the concentration recommended by the manufacturer using deionized water. Place on top of a hot plate having a stirrer and bring the bottle to a boil. After boiling, transfer the bottle to a water bath previously set at 45° C. Monitor the temperature of the agar until the temperature stabilizes at 45° C.

Aseptically weigh out 10 g of the test product in a sterile sample cup. When formulations containing significantly different concentrations of AgO are being compared, the weight of the test product may be adjusted to keep the total amount of AgO constant for all samples. Add inoculum (typically about 0.1 ml) to the test product in the sample cup such that the final concentration of microorganisms in the test product is approximately $1\times10^6$ cfu per gram. Using a sterile glass rod, mix thoroughly to obtain a homogeneous sample.

Aseptically collect 0.1 g of the inoculated test product into the sterile Petri dish at 0, 10, and 30 minutes and at 1, 2, 3, 4, 18 and 24 hours. Add 2 ml of Mueller-Hinton Broth to neutralize the effect of the product, mix well.

Pour 20 ml of TSA (45° C.) into the inoculated Petri dish. Cover and mix thoroughly by gentle tilting and swirling the dish on a flat, level surface. Place at room temperature on a flat surface undisturbed for about 10 minutes to allow the agar to completely gel. Invert and incubate at 37° C. for 24-48 hours.

After 24 hours, the colonies are counted by means of a manual technique in which a number of 100 is assigned to the control sample, and based on the density of the colonies in the other samples, a relative number is assigned based upon visual evaluation.

Examples 34-38

The modified pour plate method of Example 33 was used to evaluate the efficacy of various formulations on test organisms such as Enterococcus faecalis and water-based formulations containing water, bentonite and jojoba oil. The results are provided below, in Table 9:

TABLE 9

| SAMPLE/ EXAMPLE NO. | SAMPLE TYPE | COMPOSITION % AgO | % ZnO | NO. OF COLONIES VISUAL METHOD |
|---|---|---|---|---|
| *E. Faecalis* | control | — | — | 100 |
| 34 | silver(II) oxide-zinc oxide | 1.3 | 5.8 | 10 |
| 35 | silver(II) oxide | 1.4 | — | 15 |
| 36 | zinc oxide | — | 5.9 | 80 |
| 37 | silver(II) oxide-zinc oxide | 1.2 | 11.0 | 10 |
| 38 | silver(II) oxide-zinc oxide | 1.1 | 19.8 | 10 |

It is evident from the manual counting of the colonies, that zinc oxide without silver(II) oxide (Sample 36) is not particularly effective in reducing the number of colonies. It is further evident that while silver(II) oxide alone displays efficacy in reducing the number of colonies (Sample 35), that efficacy is greatly enhanced in Sample 34, a formulation containing zinc oxide and silver(II) oxide in or up to a 4.5:1 weight ratio. The formulations containing higher ratios of zinc oxide to silver(II) oxide (about 9:1 to 18:1), also exhibit enhanced efficacy in reducing the number of colonies.

Examples 39-43

The modified pour plate method of Example 33 was used to evaluate the efficacy of various formulations on test organisms such as Enterococcus faecalis and oil-based formulations. The results are provided below, in Table 10:

TABLE 10

| SAMPLE/ EXAMPLE NO. | SAMPLE TYPE | COMPOSITION % AgO | % ZnO | NO. OF COLONIES VISUAL METHOD |
|---|---|---|---|---|
| *E. Faecalis* | control | — | — | 100 |
| 39 | silver(II) oxide-zinc oxide | 1.0 | 7.0 | 15 |
| 40 | silver(II) oxide | 1.0 | — | 80 |
| 41 | zinc oxide | — | 7.0 | 130 |
| 42 | silver(II) oxide-zinc oxide | 1.0 | 14.0 | 160 |
| 43 | silver(II) oxide-zinc oxide | 0.84 | 28.0 | 180 |

FIG. 5 provides top view photographs of Petri dishes containing oil-based formulations and identically grown cultures according to a modified pour plate method, wherein: FIG. 5A shows a cultured Petri dish after being exposed to a formulation containing 1.0% AgO and 7.0% ZnO (Sample 39); FIG. 5B shows a cultured Petri dish after being exposed to a formulation containing 1.0% AgO and no ZnO (Sample 40); FIG. 5C shows a cultured Petri dish after being exposed to a formulation containing 7.0% ZnO and no AgO (Sample 41); FIG. 5D shows a cultured Petri dish after being exposed to a formulation containing 1.0% AgO and 14.0% ZnO (Sample 42); and FIG. 5E shows a cultured Petri dish after being exposed to a formulation containing 0.84% AgO and 28.0% ZnO (Sample 43).

It is evident from the photographs, and from the manual counting of the colonies, that zinc oxide is not effective in reducing the number of colonies. It is further evident that while silver(II) oxide alone displays efficacy in reducing the number of colonies, that efficacy is greatly enhanced in Sample 39, a formulation containing zinc oxide and silver (II) oxide in or up to a 7:1 weight ratio. However, with formulations containing high ratios of zinc oxide to silver(II) oxide (14:1 or higher, as in Samples 42 and 43), the formulation shows poor efficacy in reducing the number of colonies.

These results have some similarities to the results obtained using water-based formulations, but also exhibit some differences, most notably relating to the performance of formulations having high ratios of zinc oxide to silver(II) oxide. Without wishing to be bound by theory, I believe that in water-based formulations, the available silver(II) oxide concentrations are appreciably higher, such that the high concentration of zinc oxide may not impede, or largely may not impede, the anti-microbial action of the silver(II) oxide. In oil-based formulations, by sharp contrast, the zinc oxide, at high concentrations, may cover or impede the contact of the silver(II) oxide with the microorganisms, and thus compromises the anti-microbial efficacy. At low concentrations of zinc oxide, however, the zinc oxide may act as a solid dispersant with respect to the silver(II) oxide, thereby greatly increasing the available specific surface area thereof, but without substantial covering of the silver(II) oxide particles.

Example 44

The anti-microbial efficacy of various formulations was tested and compared using a Kirby-Bauer type test, as follows:

Ready-made Muller-Hilton agar was streaked with the bacterial inoculum using a sterile applicator. The sample was allowed to sit for 5 minutes to ensure that the bacteria adhere to the surface of the agar. Subsequently, an antibiotic sterile blank disc was pressed against a known quantity of the formulation being tested. While the amount applied to each disc was not measured, care was taken to obtain a consistent amount of material on each disc. Multiple duplicate discs were used to verify the data. The disc was pressed against the surface of the agar, making sure not to damage the disc or the agar. Each agar plate was then inverted and allowed to sit in the incubator at 37° C. for 24 hours. The plates were subsequently removed from the incubator, and the zone of inhibition was measured using a ruler.

Examples 45-46

The anti-microbial efficacy of various oil-based and water-based formulations was tested and compared using the procedure detailed in Example 44, using various individual strains of bacteria such as Enterococcus faecalis and *Staphylococcus aureus* (ATCC No. 25923).

Two oil-based formulations were tested several times against Enterococcus faecalis: Sample 45, a two-month old sample containing 1.0% AgO and no zinc oxide, disposed in a beeswax and jojoba oil base, and Sample 46, a two-month old sample containing 0.87% AgO and 6.8% ZnO, also disposed in a beeswax and jojoba oil base.

In the case of Sample 45, the zone of inhibition averaged approximately 4 mm; in the case of Sample 46, the zone of inhibition averaged approximately 18 mm. The relatively wide zone of inhibition achieved by Sample 46 indicates improved anti-microbial efficacy with respect to Sample 45, despite a lower total content of AgO.

It would appear that the improved anti-microbial efficacy in these oil-based formulations is attributable to the presence of zinc oxide in Sample 41, and more particularly, to the presence of zinc oxide in a weight ratio of less than 14:1, less than 12:1, and less than 10:1. Without wishing to be bound by theory, I believe that, as stated hereinabove, the zinc oxide may act as a solid dispersant with respect to the silver(II) oxide, thereby greatly increasing the available specific surface area thereof, but—within or below these weight ratios—without substantial covering of the silver(II) oxide particles.

The medical device of the present invention may also contain both a silver oxide compound and a whitening agent, preferably in a carrier medium that may be a water-based cream or lotion, or an ointment that may include a wax and/or an oil. The formulation may include an emulsion, or be substantially emulsion-based.

Figure 6:
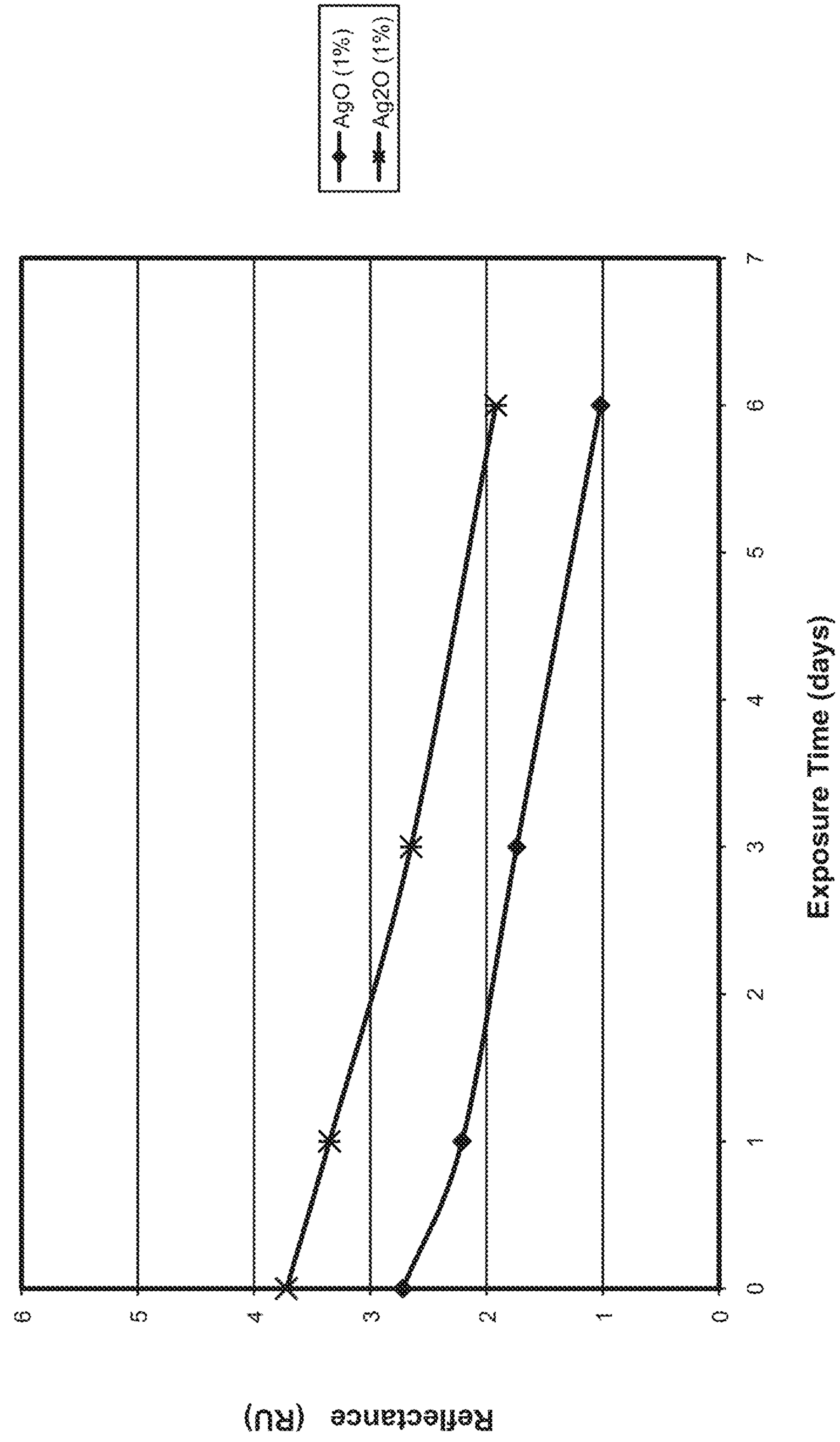
FIG. 6 is a graph plotting formulation whiteness, as a function of the exposure time to ultraviolet light, for formulations containing AgO (1%) and $Ag_2O$ (1%), respectively, in a carrier base.

FIG. 6 is a graph plotting formulation whiteness, as a function of the exposure time to ultraviolet light, for formulations containing AgO (1%) and $Ag_2O$ (1%), in a carrier base described in Example 1 hereinbelow. After preparing the formulations, the whiteness was measured by reflectance using a LabScan XE spectrophotometer instrument (HunterLab, Va.). Initially, the AgO formulation was a relatively dark gray, and the initial value of whiteness was 2.72 reflective units. The $Ag_2O$ formulation also had a dark gray color, albeit somewhat lighter than the AgO formulation, and exhibited an initial value of whiteness of 3.72 reflective units.

The formulations were then subjected to ultraviolet light for several days, and the whiteness of each of the formulations was monitored over time. We found that the measured reflectance or lightness of the AgO formulation decreased monotonically over time, as the formulation took on a progressively darker hue of gray. The reflectance decreased to 1.74 reflective units after 3 days, and further decreased to 1.02 reflective units after 6 days. Similarly, the measured reflectance or lightness of the $Ag_2O$ formulation decreased monotonically over time, as the gray formulation became progressively darker. The reflectance decreased to 3.35 reflective units after 1 day, 2.65 reflective units after 3 days, and further decreased to about 1.9 reflective units after 6 days.

Figure 6A:
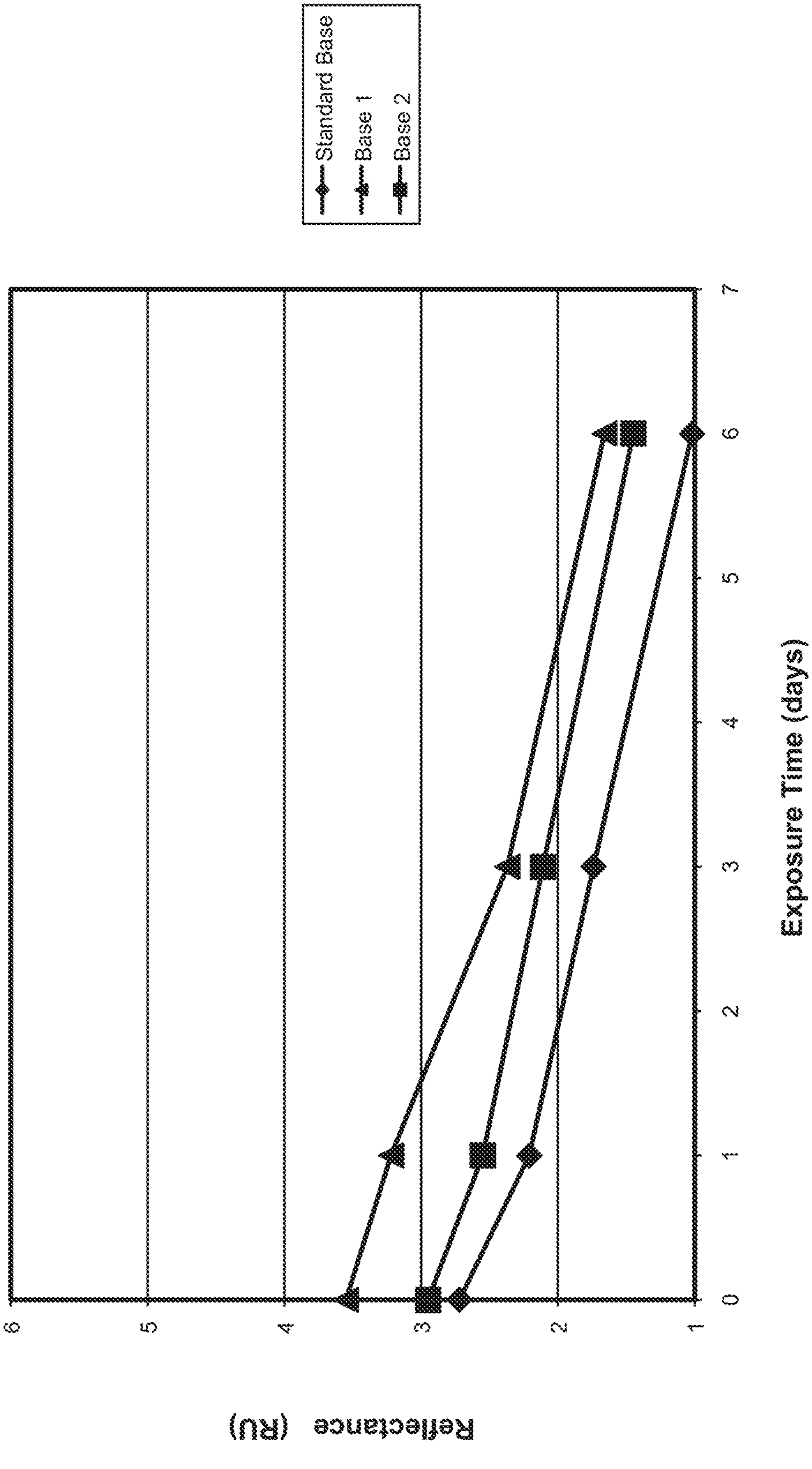
FIG. 6A is a graph plotting reflectance, as a function of the exposure time to ultraviolet light, for three formulations containing AgO (1%) in various carrier bases.

FIG. 6A is a graph plotting formulation whiteness, as a function of the exposure time to ultraviolet light, for three formulations containing AgO (1%): the first formulation is the formulation associated with FIG. 1, containing AgO in the "standard base" (described in detail in Example 1 hereinbelow); the second formulation contained an oxidized polyethylene homopolymer (Honeywell A-C® 629), jojoba oil, and xanthum gum ("Base 1"); and the third formulation contained beeswax, coconut oil and xanthum gum ("Base 2"). The three formulations exhibit a similar monotonous decrease in lightness over the six-day exposure period.

Without wishing to be limited by theory, we believe that silver oxide (including both silver(II) oxide and silver(I) oxide), being a reactive material, interacts with at least one other material within the formulation, causing discoloration over time. This effect may be accelerated or augmented by exposure to sunlight. In sunlight, the discoloration may be apparent even within minutes.

We have found that this effect may actually be an acceleration of a process that occurs, albeit much more slowly, when the silver oxide based formulation is packaged in a container. Thus, the discoloration phenomenon may be significant because:

- topical formulations, applied to the skin, are commonly exposed to sunlight; and
- the shelf life of silver oxide based formulations may be severely limited by the discoloration process occurring within the container.

By adding various whiteners during the preparation of the formulations, we found that the appearance of the formulations became significantly lighter. In the case of zinc oxide, the measured whiteness value of the silver(II) oxide formulation (1% AgO, 7% ZnO) increased by almost 3 reflectance units, to about 5.43, and the measured whiteness value of the silver(I) oxide formulation (1% $Ag_2O$, 7% ZnO) increased by slightly more than 3 reflectance units, to about 6.87. In the case of titanium dioxide, the measured whiteness value of the formulation (1% AgO, 7% $TiO_2$) nearly doubled to about 5.33. Such light-colored formulations (cream, ointment, etc.) are much more aesthetically pleasing to users, and may pose less of a problem regarding staining of skin and clothing.

Figure 7:
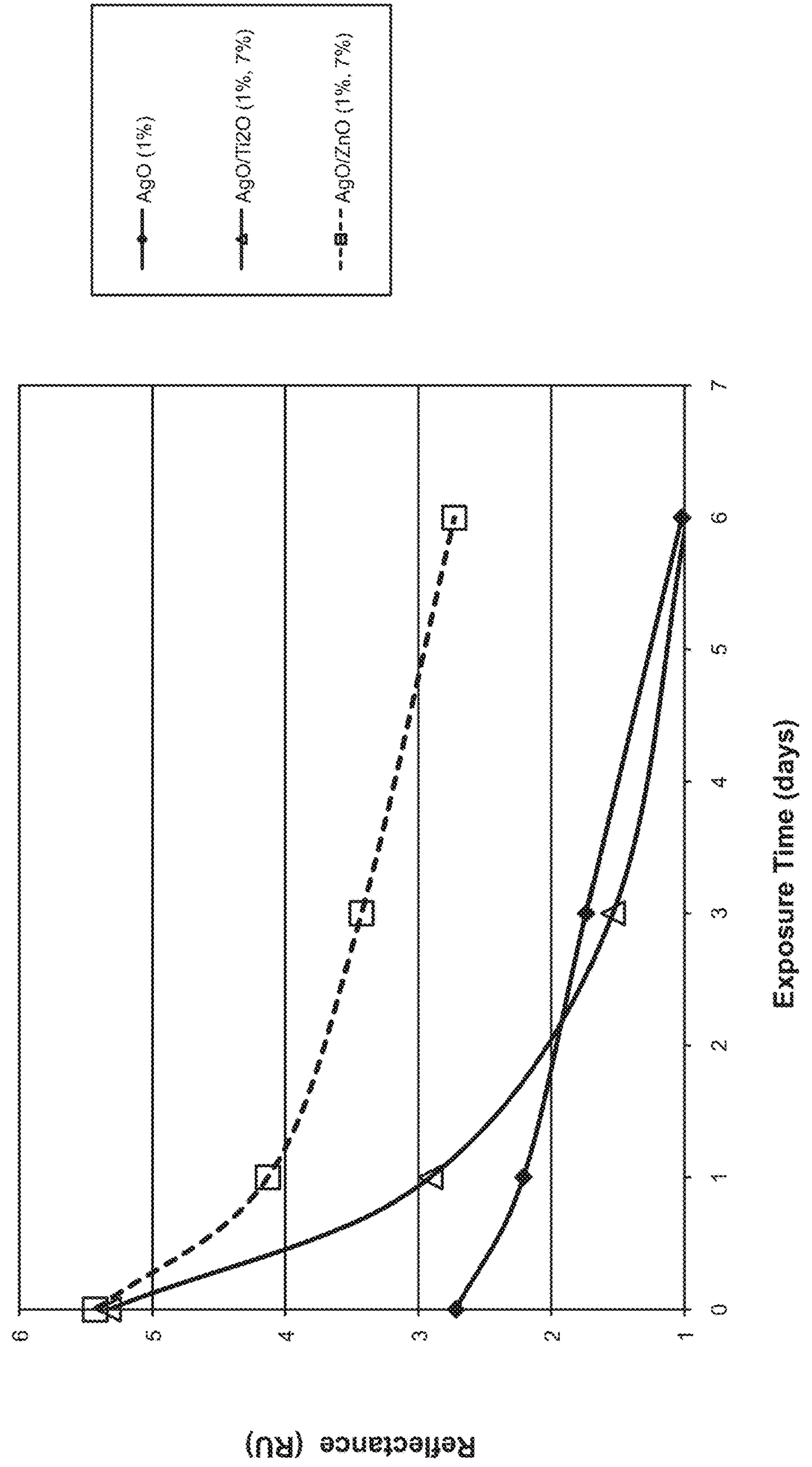
FIG. 7 is a graph plotting formulation whiteness, as a function of the exposure time to ultraviolet light, for the AgO formulation of FIG. 6, versus similar formulations containing AgO along with the inorganic whiteners $TiO_2$, and ZnO, respectively.

These formulations were then subjected to ultraviolet light for several days, in a procedure substantially identical to that used on the formulations described hereinabove, and the whiteness of each of the formulations was monitored over time. FIG. 7 is a graph plotting formulation lightness, as a function of the exposure time to ultraviolet light, for the AgO formulation of FIG. 6, versus similar formulations containing AgO along with the inorganic whiteners ZnO and $TiO_2$, respectively. It may have been expected that the whiteners would cover up a portion of the AgO, producing a lighter formulation in which the AgO is also less exposed to the ultraviolet light, such that during exposure to ultraviolet light, the decrease in whiteness might be much more moderate.

Surprisingly, we found that with both ZnO and $TiO_2$, the decrease in whiteness, as a function of UV exposure time, may actually be more pronounced than the corresponding decrease in whiteness of the identical formulation, without the additional whitener. In the case of the AgO/ZnO formulation, the whiteness value decreased by 2 reflective units within 3 days, and by 2.7 reflective units within 6 days.

Similar results were obtained with Ag2O: after 3 days, the whiteness value of an AgO/ZnO (1%, 7%) formulation decreased by about 1.9 reflective units; the whiteness value of an AgO/ZnO/$TiO_2$ (1%, 3.5%, 3.5%) formulation decreased by about 3.8 reflective units.

Thus, while the use of such whiteners greatly improved the initial formulation color, the use of these whiteners raised additional issues. Both silver(I) and silver(II) oxides may interact with the zinc oxide and titanium dioxide, or with the carrier base in the presence of zinc oxide and/or titanium dioxide, causing significant discoloration within a day or days. This effect may be accelerated or augmented by exposure to direct sunlight, in which the discoloration may be effected within minutes.

Many of the tests on AgO-based formulations have been repeated for $Ag_2O$-based formulations, which typically provide qualitatively similar results.

Figure 8:
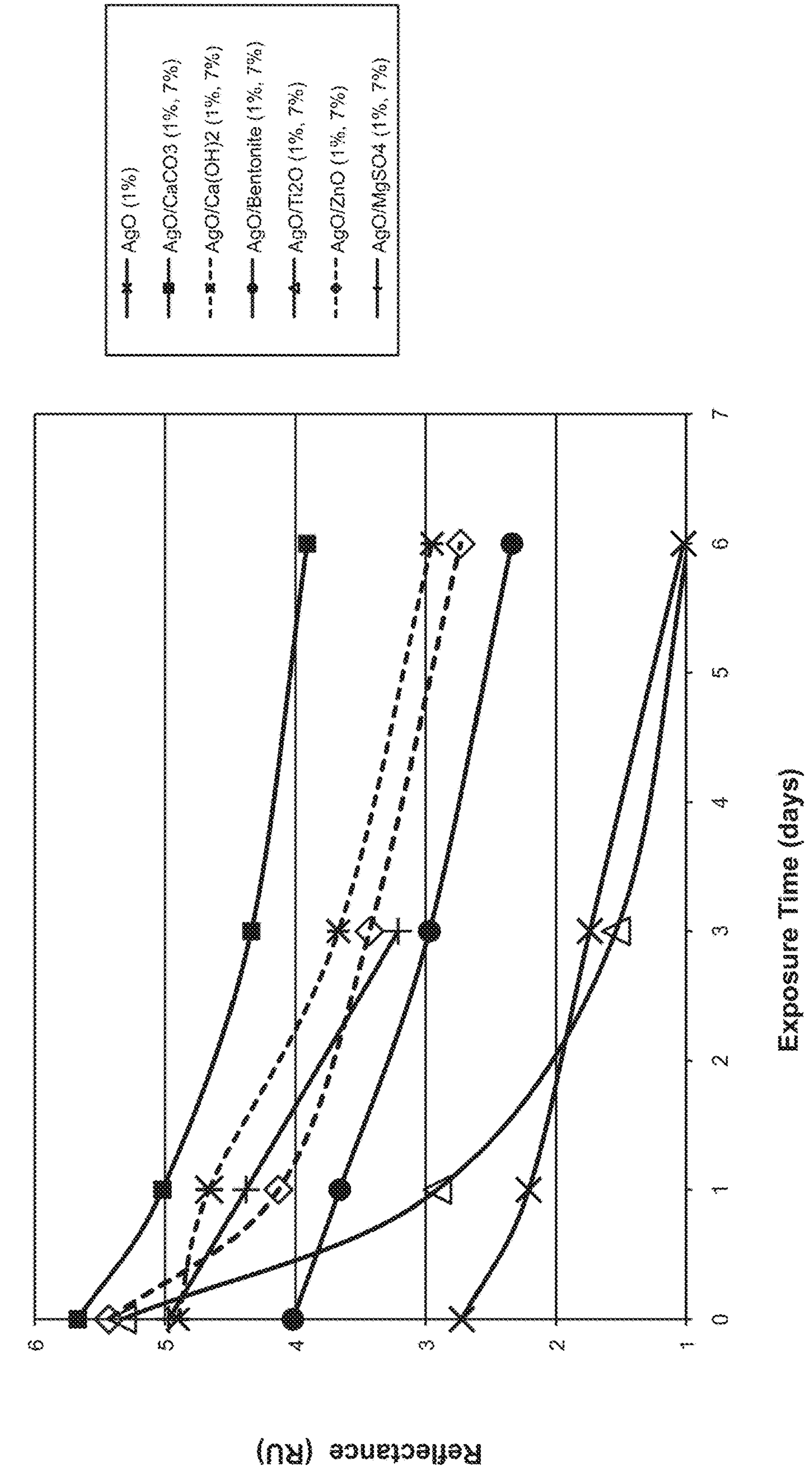
FIG. 8 provides a graph plotting formulation whiteness, as a function of the exposure time to ultraviolet light, for the formulations of FIG. 7, versus similar formulations containing AgO along with the inorganic substances bentonite, $CaCO_3$, $Ca(OH)_2$ and $MgSO_4$, respectively.

FIG. 8 is a graph plotting formulation whiteness, as a function of the exposure time to ultraviolet light, for the formulations of FIG. 7, versus similar formulations containing AgO along with the inorganic substances bentonite, $CaCO_3$, $Ca(OH)_2$ and $MgSO_4$, respectively. All of the mixed formulations contained 1% AgO and 7% of the additional inorganic material, to provide a firm basis of comparison.

Immediately after preparation, all of the mixed formulations whiteners were significantly lighter than the AgO standard formulation. The AgO/bentonite formulation exhibited a reflectance just over 4 reflective units, a 48% increase with respect to the AgO standard formulation. The AgO/$Ca(OH)_2$ and AgO/$MgSO_4$ formulations both exhibited a reflectance of almost 5 reflective units (4.9 and 4.97, respectively), corresponding to more than an 80% increase with respect to the AgO standard formulation. In the case of calcium carbonate, the measured whiteness value of the formulation (1% AgO, 7% $CaCO_3$) more than doubled to about 5.67.

The formulations were then subjected to ultraviolet light for several days, as described hereinabove, and the whiteness of each of the formulations was monitored over time. All of the formulations exhibited decreasing whiteness, as a function of UV exposure time. With the exception of the AgO/$TiO_2$ formulation, all of the formulations maintain a substantially higher reflectance after 1 day, after 3 days, and after 6 days. Moreover, we observe that the decreasing whiteness is less pronounced in some of the formulations.

Figure 8A:
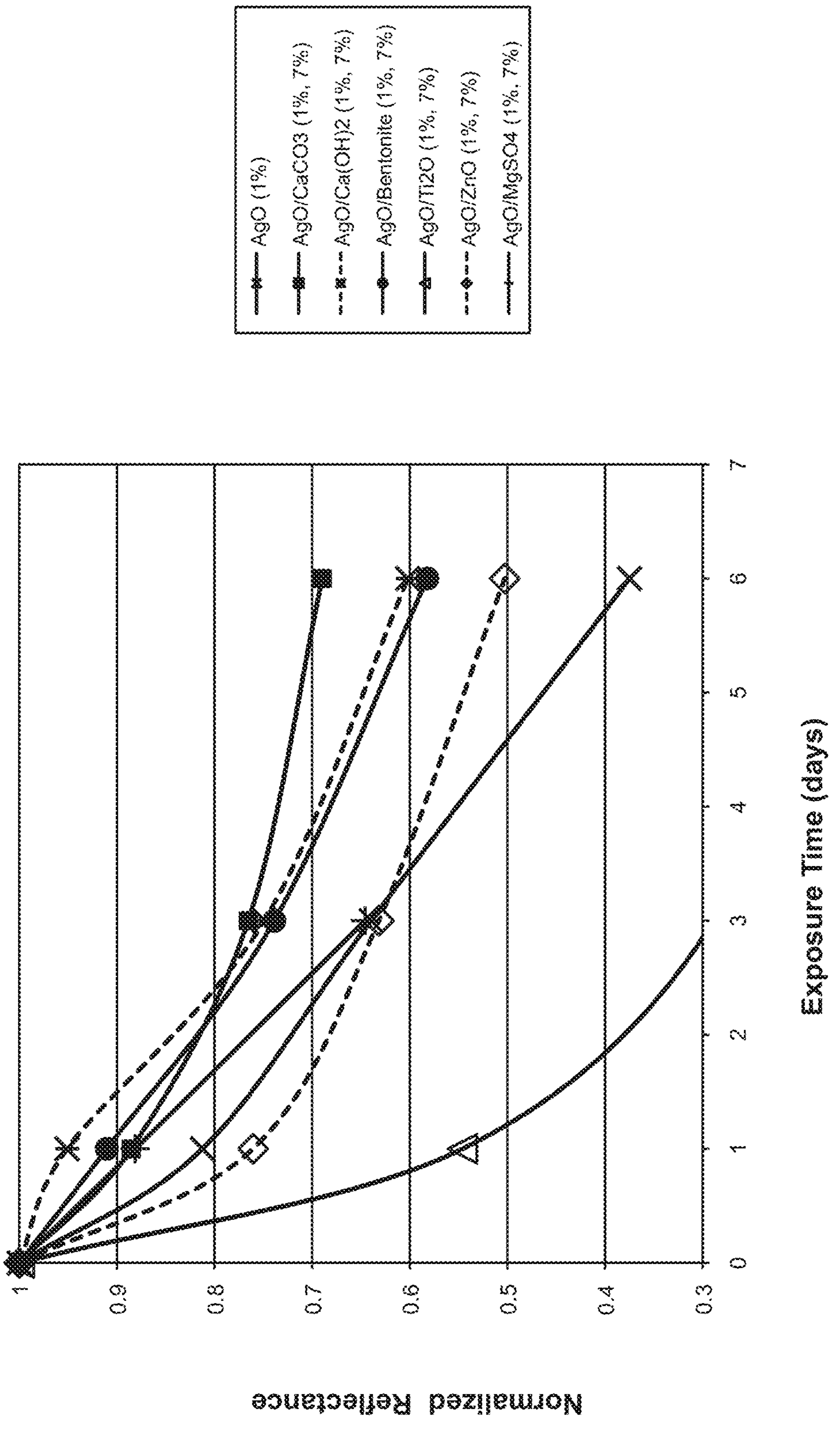
FIG. 8A presents a graph plotting normalized formulation whiteness (whiteness equals 1 at t=0), as a function of the exposure time to ultraviolet light, for the formulations of FIG. 8.

FIG. 8A presents a graph plotting normalized formulation whiteness (WN) as a function of the exposure time to ultraviolet light, for the formulations of FIG. 8. The normalization is based on the initial formulation whiteness (normalized reflectance or whiteness equals 1 at t=0). It is readily observed that the performance of the AgO/$TiO_2$ formulation is appreciably worse than that of the standard AgO formulation, with the normalized whiteness dropping below 0.3 after 3 days of UV exposure. The performance of the AgO/ZnO and AgO/$MgSO_4$ formulations is fairly similar to that of the standard AgO formulation, with the normalized whiteness dropping to about 0.63 and 0.65, respectively, after 3 days of UV exposure.

The other formulations, containing AgO along with bentonite, $CaCO_3$, and $Ca(OH)_2$, respectively, all exhibit a normalized formulation whiteness exceeding 0.7 after 3 days of UV exposure. The 1% AgO, 7% $CaCO_3$ formulation exhibited a normalized formulation whiteness approaching 0.7, even after 6 days of UV exposure.

Figure 3:
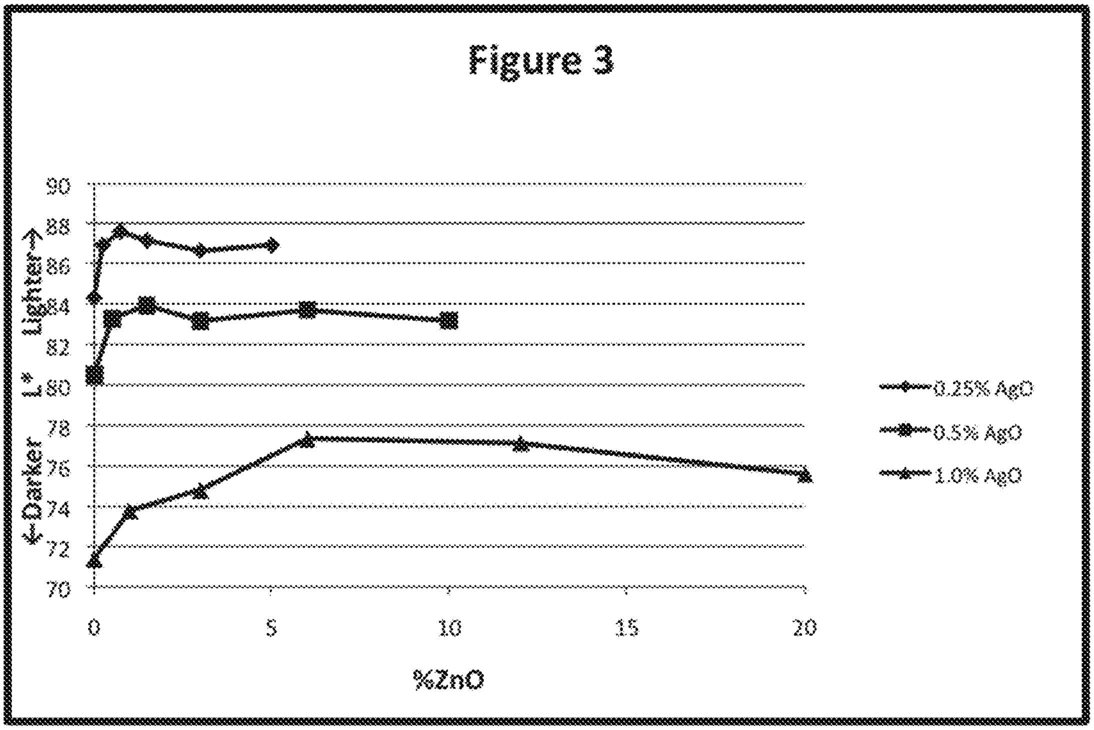
FIG. 3 is a graph plotting whiteness of laundered cloth swatches as a function of the weight content of zinc oxide in the staining formulations initially applied to the swatches.
Figure 8B:
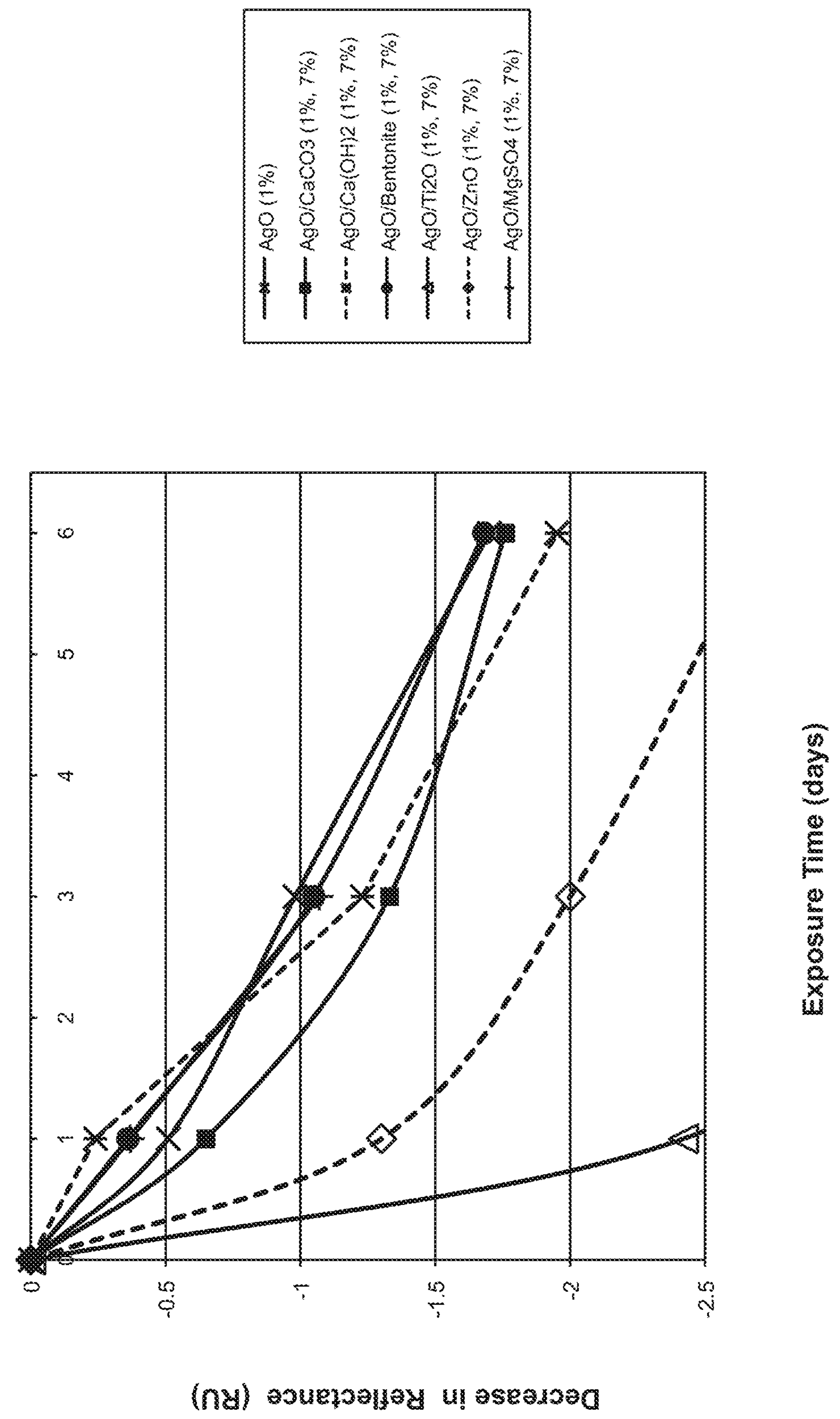
FIG. 8B is a graph plotting the absolute decrease in formulation reflectance (in RU) as a function of the exposure time to ultraviolet light, for the formulations of FIG. 8.

FIG. 8B presents a graph plotting the absolute decrease in formulation reflectance (in RU) as a function of the exposure time to ultraviolet light, for the formulations of FIG. 3. While all of the formulations exhibited decreasing whiteness, as a function of UV exposure time, the absolute decrease in reflectance for the AgO/ZnO and the AgO/$TiO_2$ formulations was over 2-4 times the absolute decrease in reflectance for the AgO formulation after 1 day of UV exposure, and about 2-4 times the absolute decrease in reflectance for the AgO formulation after 3 days of UV exposure. With the exception of the AgO/$TiO_2$ formulation, all of the formulations maintain a substantially higher reflectance after 1 day, after 3 days, and after 6 days.

By sharp contrast, the absolute decrease in reflectance for the formulations containing AgO along with bentonite, $CaCO_3$, $MgSO_4$, and $Ca(OH)_2$, was reduced with respect to the absolute decrease in reflectance for the AgO formulation after both 1 day and 3 days of UV exposure.

Figure 9:
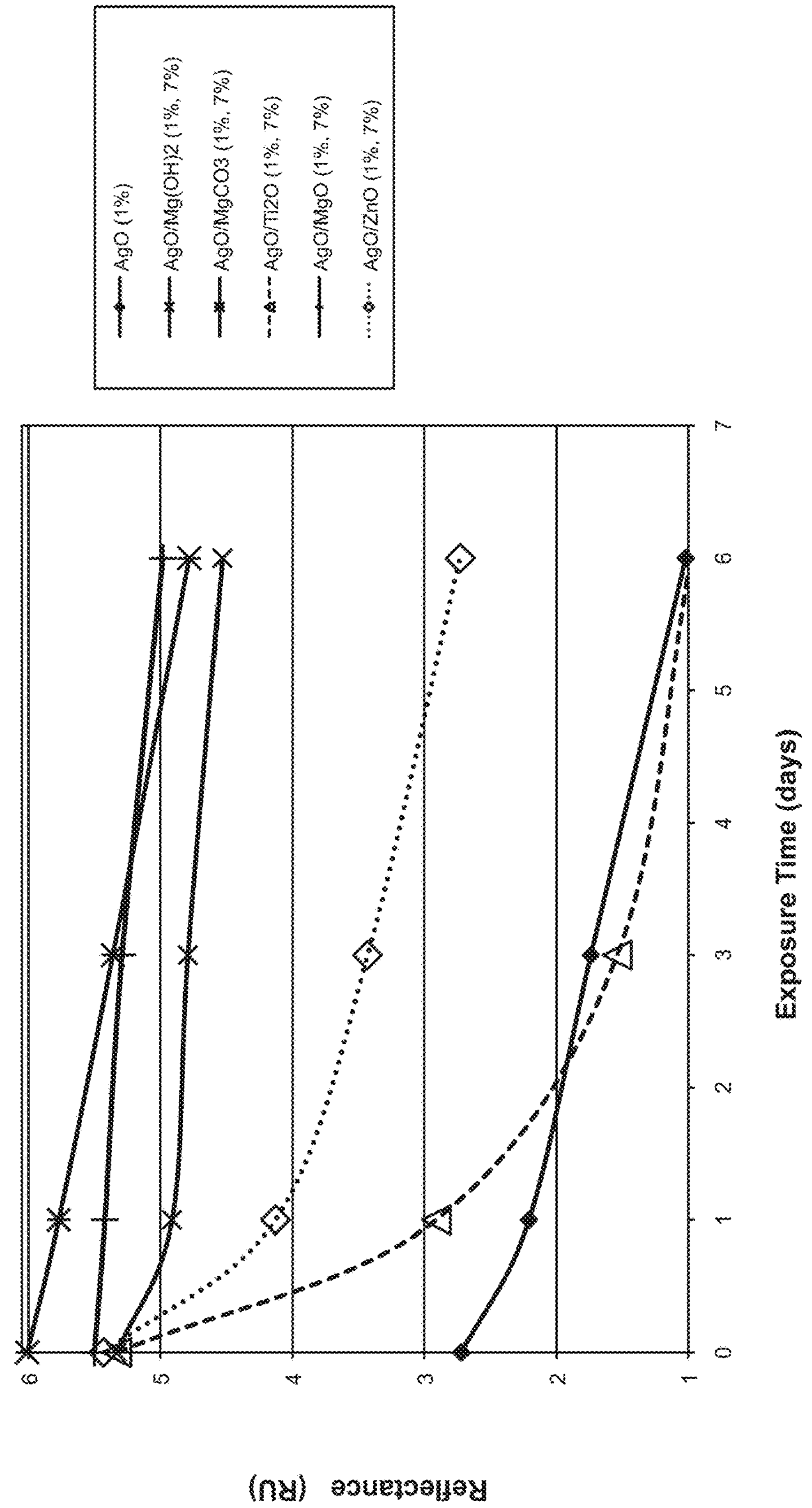
FIG. 9 is a graph plotting formulation whiteness, as a function of the exposure time to ultraviolet light, for the formulations of FIG. 7, versus similar formulations containing AgO along with the inorganic substances $Mg(OH)_2$, $MgCO_3$, and MgO, respectively.

FIG. 9 is a comparison graph plotting formulation whiteness, as a function of the exposure time to ultraviolet light, for the formulations of FIG. 7, versus similar formulations containing AgO along with the inorganic substances $Mg(OH)_2$, $MgCO_3$, and MgO, respectively. All of the mixed formulations contained 1% AgO and 7% of the additional inorganic material.

Immediately after preparation, all of the mixed formulations whiteners were significantly lighter than the AgO standard formulation. The AgO/$Mg(OH)_2$ formulation exhibited 5.33 reflective units, a 96% increase with respect to the AgO standard formulation. The AgO/MgO and AgO/$MgCO_3$ formulations exhibited almost 5.5 and 6.01 reflective units, respectively, corresponding to more than a 100% or 120% increase with respect to the AgO standard formulation.

The formulations were then subjected to ultraviolet light for several days, as described hereinabove, and the whiteness of each of the formulations was monitored over time. Although these formulations exhibited decreasing whiteness, as a function of UV exposure time, the decreasing whiteness was surprisingly moderate.

Figure 9A:
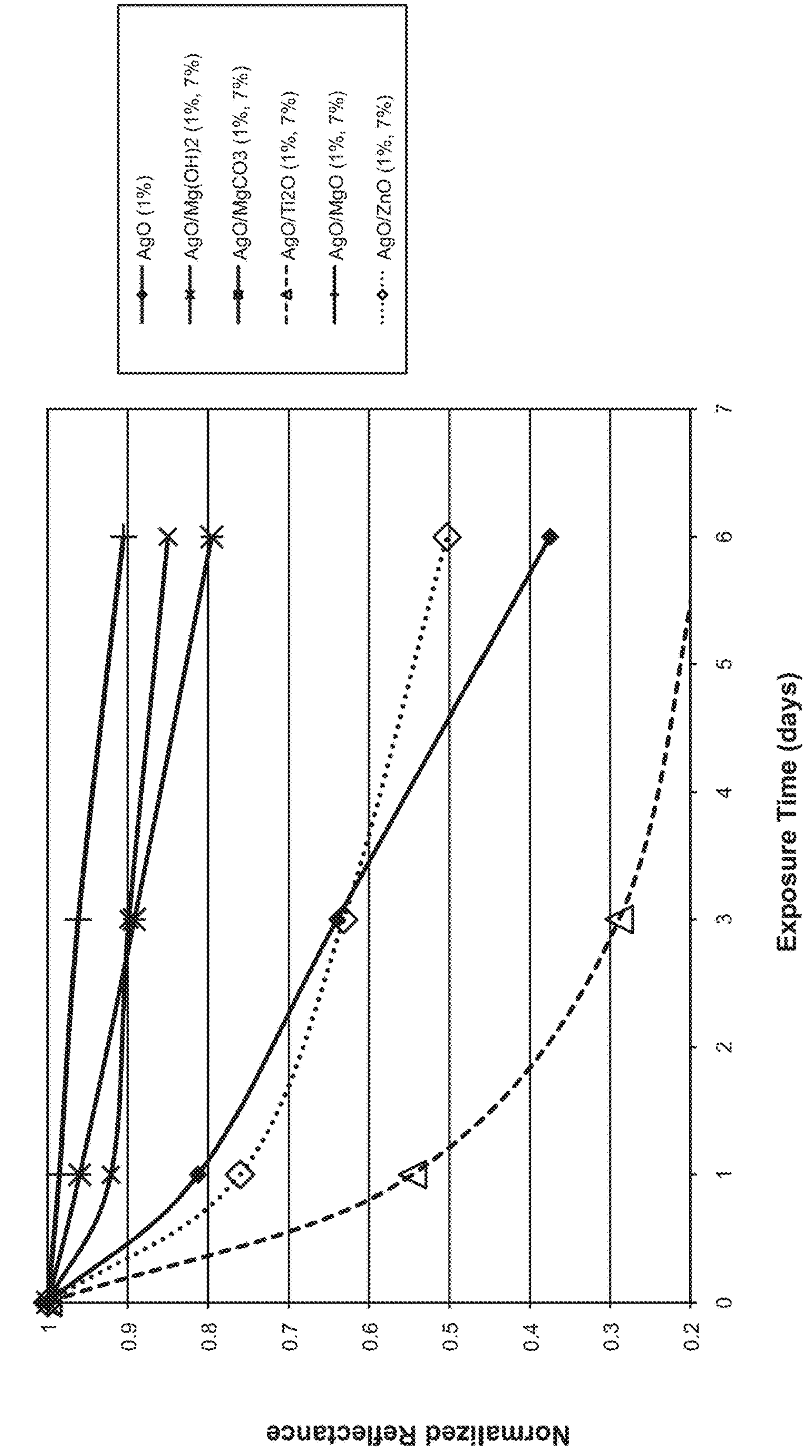
FIG. 9A provides a graph plotting normalized formulation reflectance or whiteness (WN) as a function of the exposure time to ultraviolet light, for the formulations of FIG. 9.

FIG. 9A presents a comparison graph plotting normalized formulation whiteness ($W_N$) as a function of the exposure time to ultraviolet light, for the formulations of FIG. 9. The AgO/$Mg(OH)_2$, AgO/MgO and AgO/$MgCO_3$ formulations, all exhibit a normalized formulation whiteness approaching or exceeding 0.9 after 3 days of UV exposure, and approaching or exceeding 0.8 after 6 days of UV exposure. The 1% AgO, 7% MgO formulation exhibited a normalized formulation whiteness exceeding 0.9, even after 6 days of UV exposure.

Figure 9B:
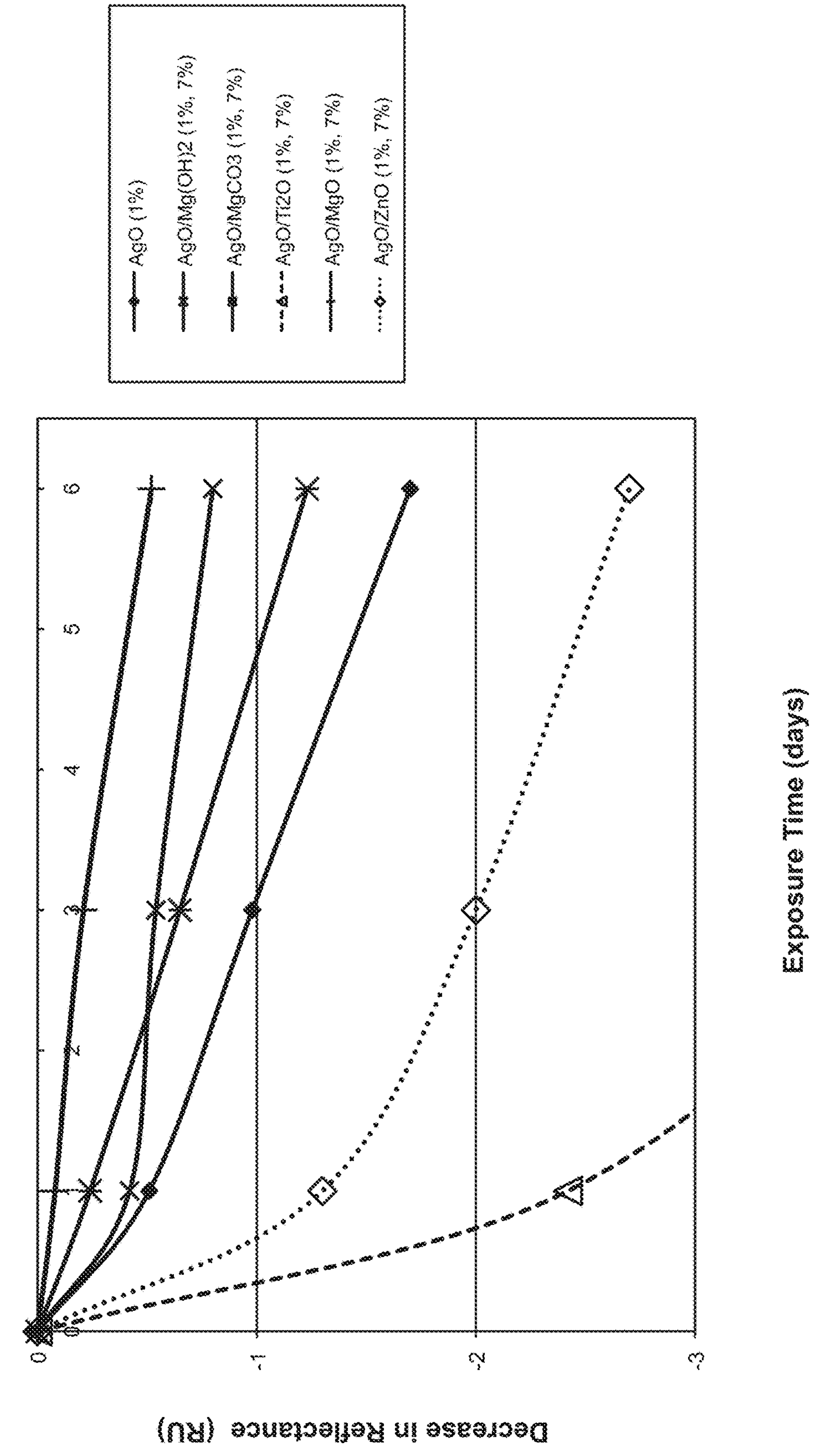
FIG. 9B presents a graph plotting the absolute decrease in formulation reflectance as a function of the exposure time to ultraviolet light, for the formulations of FIG. 9.

FIG. 9B presents a graph plotting the absolute decrease in formulation reflectance (in RU) as a function of the exposure time to ultraviolet light, for the formulations of FIG. 9. While all of the formulations exhibited decreasing whiteness, as a function of UV exposure time, the absolute decrease in reflectance for the AgO/$Mg(OH)_2$, AgO/MgO and AgO/$MgCO_3$ formulations was significantly less than that of the AgO formulation after 1 day of UV exposure, after 3 days of UV exposure, and after 6 days of UV exposure.

Over the course of clinical trials, we have found that treating wounds with an AgO/ZnO formulation may be considerably more efficacious than conventional treatments used in the controls. Moreover, the AgO/ZnO formulation exhibited a higher efficacy than a similar formulation containing a comparable concentration of AgO, but no ZnO. In addition, the AgO/ZnO formulation was found to improve the microcirculation and healing rate in both venous ulcerations and diabetic ulcerations.

The darkening of the AgO/ZnO formulation over time, and during exposure to UV light, may be a disadvantage in many applications. As best seen in FIG. 7, the darkening of AgO/ZnO formulations may be rapid and appreciable. After only one day of UV exposure, the "white" AgO/ZnO formulation has become nearly as dark as the identical formulation, without ZnO; after three days of UV exposure, the AgO/ZnO formulation looks extremely similar to that formulation, and may actually be even darker. Thus, while the ZnO contributes to the formulation efficacy, the contribution to the whiteness may be surprisingly modest. In addition, the dark appearance of the formulation, developed over time, may reduce patient compliance.

We have found that the appearance of formulations containing AgO and ZnO may be greatly enhanced by the addition of at least one stabilization agent adapted to at least partially inhibit a darkening of the formulation when exposed to ultraviolet light. The stabilization agent may advantageously act as a whitener as well.

Figure 10:
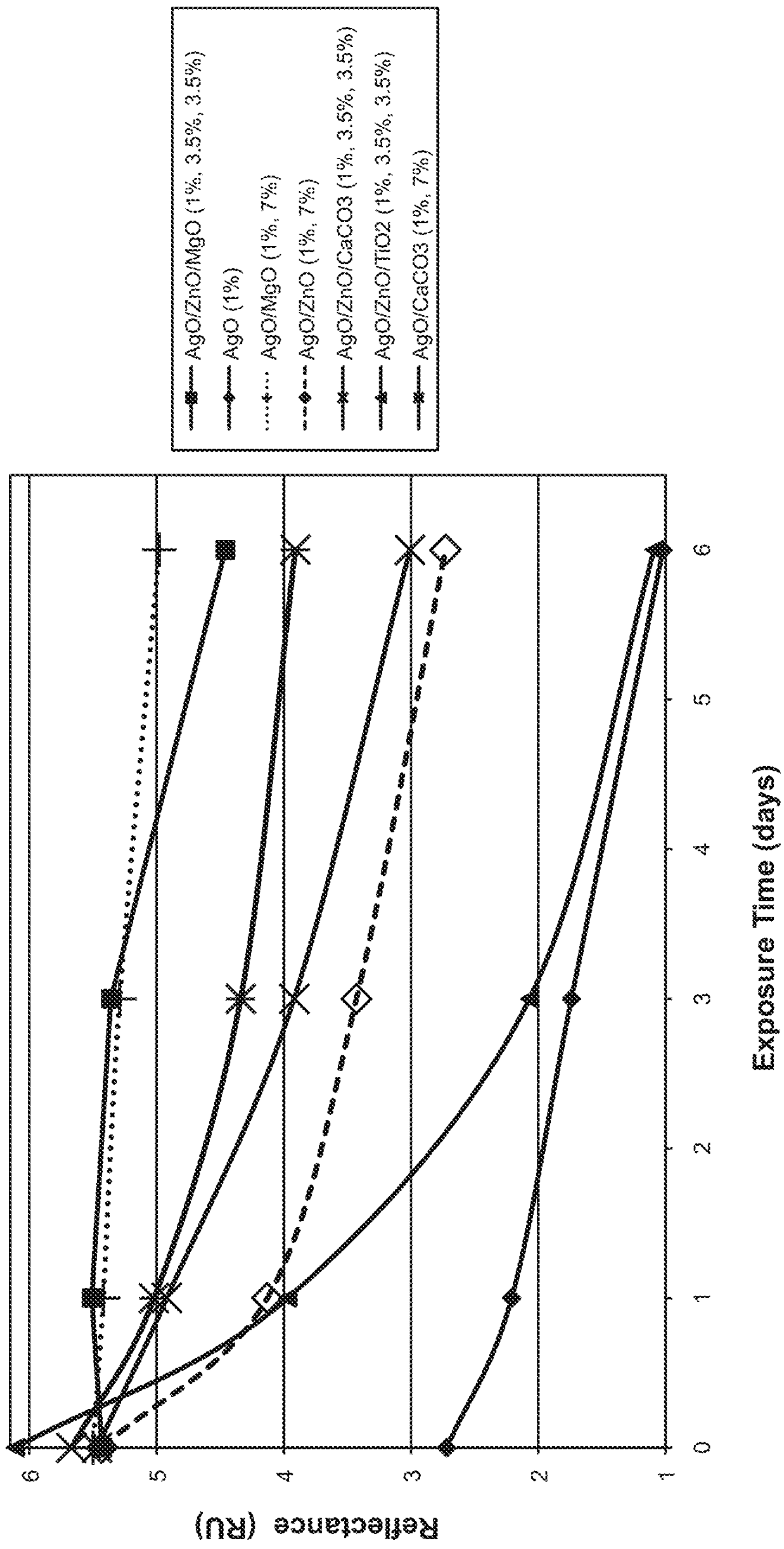
FIG. 10 is a graph plotting formulation whiteness, as a function of the exposure time to ultraviolet light, showing the whiteness stabilization performance of various inorganic substances in formulations containing AgO and ZnO.
Figure 10A:
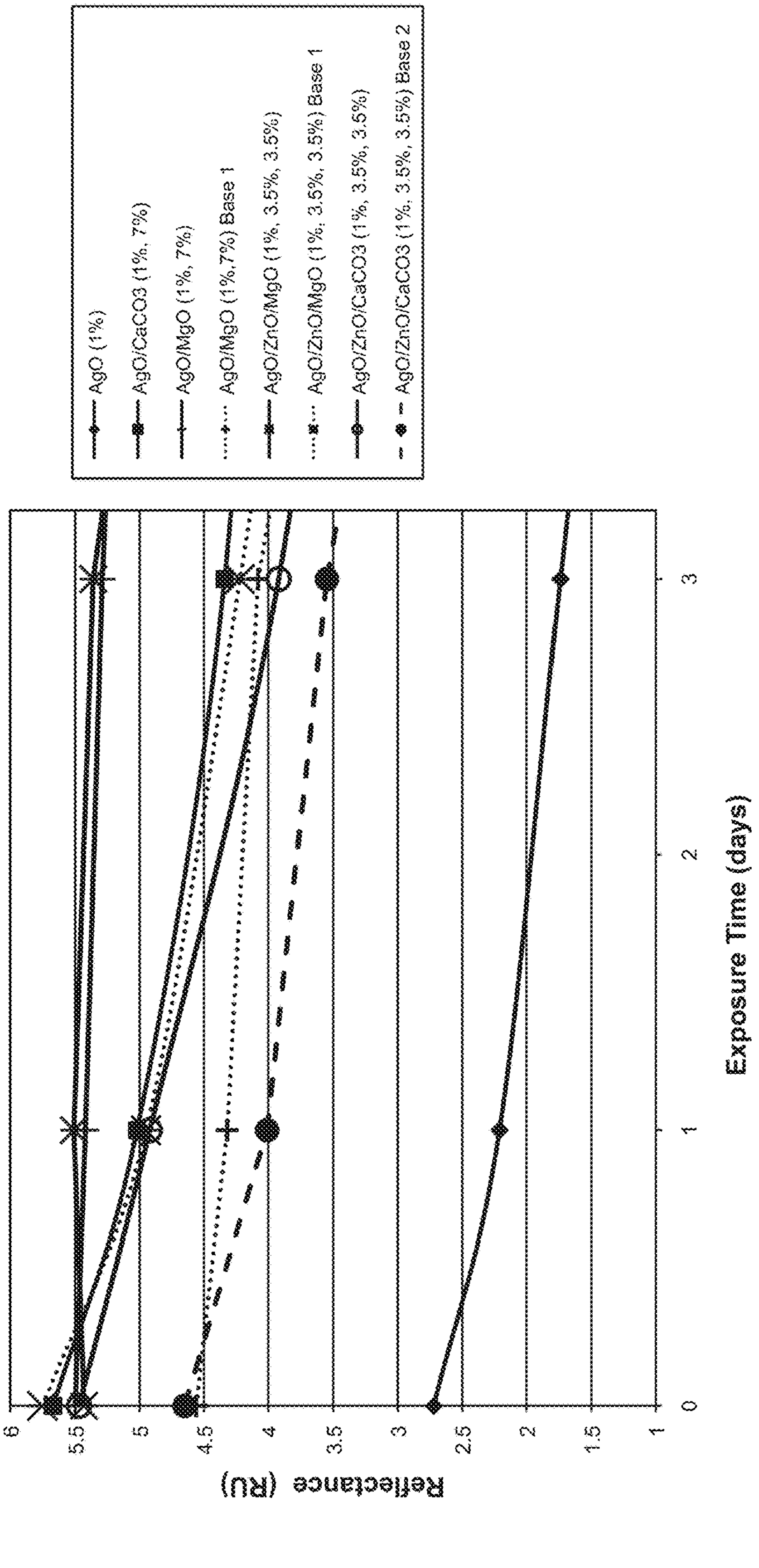
FIG. 10A is a graph comparing formulation whiteness of various formulations of FIG. 10, with the formulation whiteness of substantially identical formulations having different carrier base compositions, as a function of the exposure time to ultraviolet light.

FIG. 10 is a graph plotting formulation whiteness, as a function of the exposure time to ultraviolet light, showing the whiteness stabilization performance of various inorganic substances in formulations containing AgO and ZnO. As described hereinabove, the decrease in whiteness of the AgO/ZnO control or base formulation (1% AgO/7% ZnO), as a function of UV exposure time, is more pronounced than the corresponding decrease in whiteness of the identical AgO formulation, without the zinc oxide. When half of the zinc oxide is replaced with titanium dioxide, the initial whiteness is improved, but after three days of UV exposure, the whiteness exhibited by the AgO/ZnO/$TiO_2$ formulation (1% AgO/3.5% ZnO/3.5% $TiO_2$) is significantly lower than that of the base formulation.

By sharp contrast, when half of the zinc oxide is replaced with magnesium oxide, the initial whiteness is substantially maintained, but over the course of several days of UV exposure, the whiteness exhibited by the AgO/ZnO/MgO formulation (1% AgO/3.5% ZnO/3.5% MgO) is significantly higher than that of the base formulation. Surprisingly, the whiteness stays fairly constant over the first three days of UV exposure, and—perhaps even more surprisingly, the whiteness exhibited appears to be very similar to the whiteness (plotted in FIG. 5, as a reference line) of an AgO/MgO formulation containing 1% AgO, 7% MgO, and having no ZnO.

Similarly, when half of the zinc oxide is replaced with calcium carbonate ($CaCO_3$), the initial whiteness is substantially maintained. Over the course of several days of UV exposure, the whiteness exhibited by the AgO/ZnO/$CaCO_3$ formulation (1% AgO/3.5% ZnO/3.5% $CaCO_3$) is somewhat higher than that of the base formulation. Surprisingly, through the third day of UV exposure, the whiteness exhibited appears to be similar to the whiteness (plotted in the Figure, as a reference line) of an AgO/$CaCO_3$ formulation containing 1% AgO, 7% $CaCO_3$, and having no ZnO.

Figure 11:
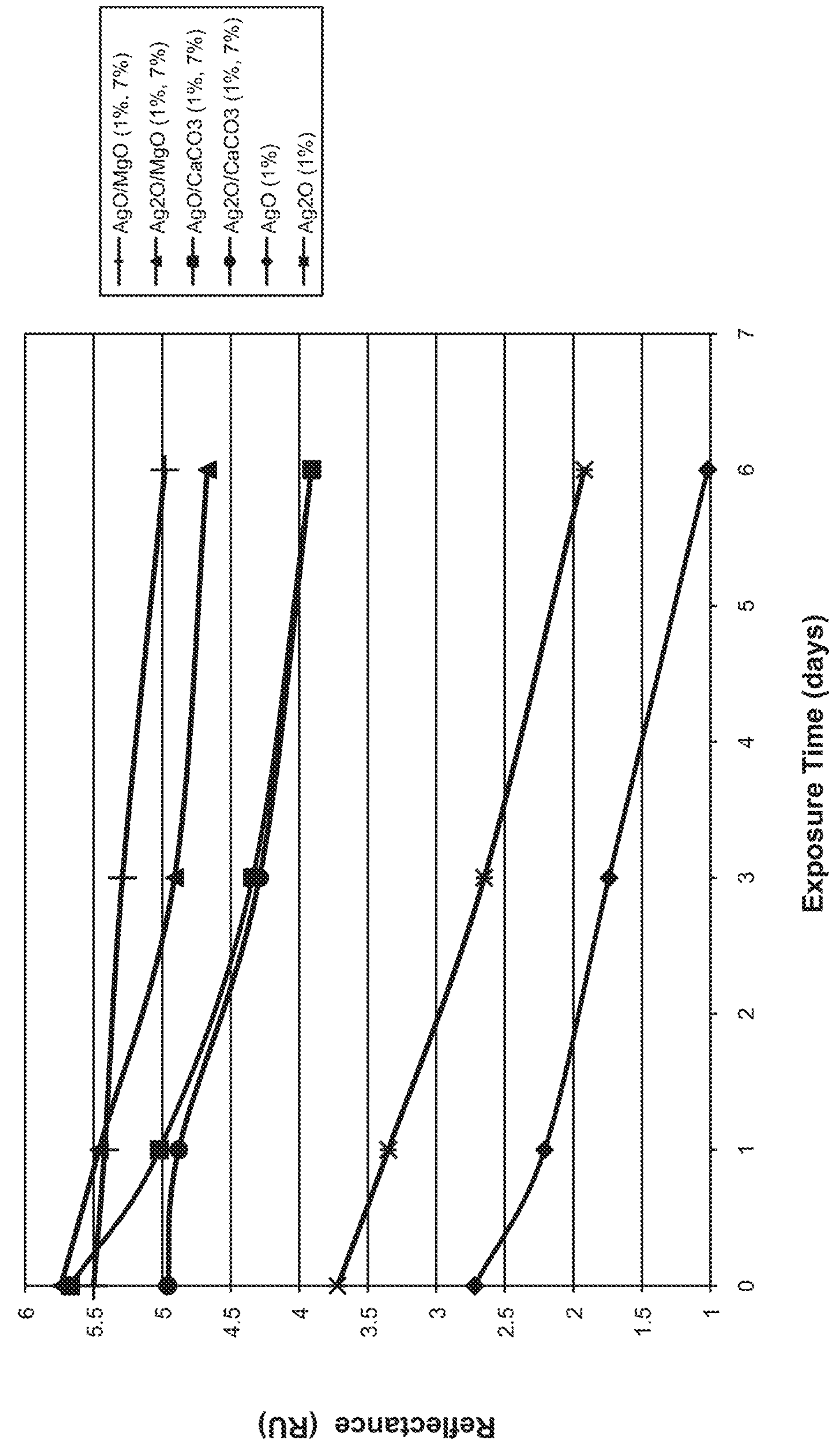
FIG. 11 is a graph plotting the whiteness behavior of various AgO based formulations and the whiteness behavior of various $Ag_2O$ based formulations, as a function of the exposure time to ultraviolet light.

FIG. 11 is a graph plotting the whiteness behavior of various AgO based formulations and the whiteness behavior of various $Ag_2O$ based formulations, as a function of the exposure time to ultraviolet light. All of the mixed formulations contained 1% AgO or $Ag_2O$, and 7% of the additional inorganic material—MgO or $CaCO_3$, respectively.

The formulations were subjected to ultraviolet light for several days, as described hereinabove, and the whiteness of each of the formulations was monitored over time. Although the mixed formulations exhibited decreasing whiteness as a function of UV exposure time, the decreasing whiteness was surprisingly moderate for both AgO-based and $Ag_2O$-based mixed formulations.

Moreover, we have found with these exemplary mixed formulations, as well as with other mixed formulations, that the behavior of the $Ag_2O$-based formulations and the $Ag_2O$-based formulations, with respect to UV light exposure, is strikingly similar. By way of example, the measured whiteness for AgO/$CaCO_3$, and $Ag_2O$/$CaCO_3$, is virtually identical for exposure times of 1 day, 3 days and 6 days.

Similarly, the measured whiteness values for the AgO/MgO and $Ag_2O$/MgO formulations, respectively, are within 5% of each other initially, and remain within about 7% of each other for exposure times of 1 day, 3 days and 6 days.

Figure 11A:
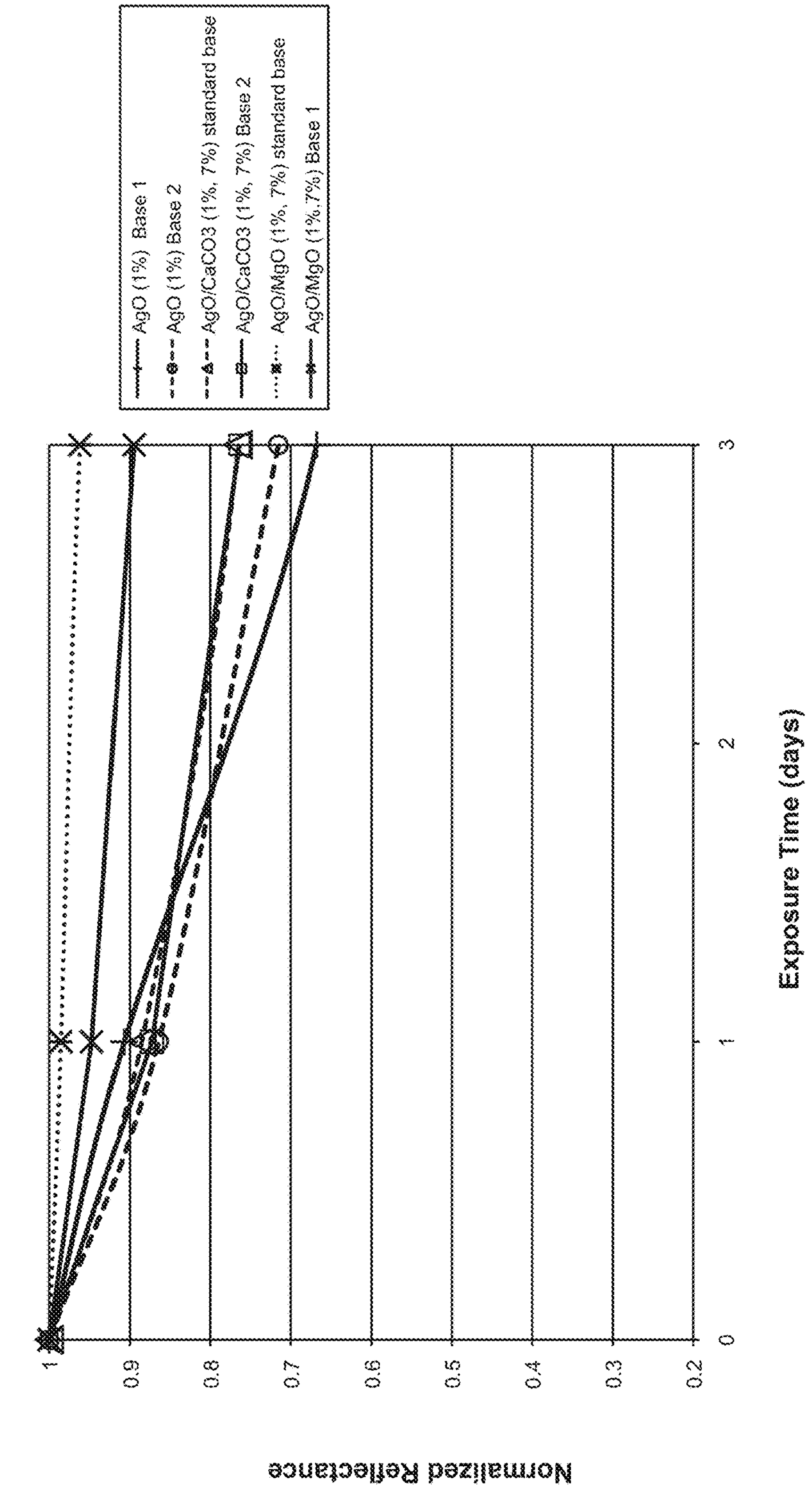
FIG. 11A presents a graph plotting normalized formulation reflectance (WN) as a function of the exposure time to ultraviolet light, for silver oxide formulations (1% by weight) having different carrier bases.

FIG. 11A presents a graph plotting normalized formulation reflectance or whiteness ($W_N$) as a function of the exposure time to ultraviolet light, for six silver oxide formulations (1% by weight) having different carrier bases. Two of the formulations contained solely (i.e., sans whiteners or stabilization agents) 1% AgO in Base 1 or in Base 2, respectively; two of the formulations contained 1% AgO and 7% $CaCO_3$, in the standard base or in Base 2, respectively; and two of the formulations contained 1% AgO and 7% MgO in the standard base or in Base 1, respectively.

Despite the significant differences in the chemical and physical properties of the carrier bases, we observe that the behavior of each type of formulation appears to be largely insensitive to the composition of the carrier base.

Figure 12:
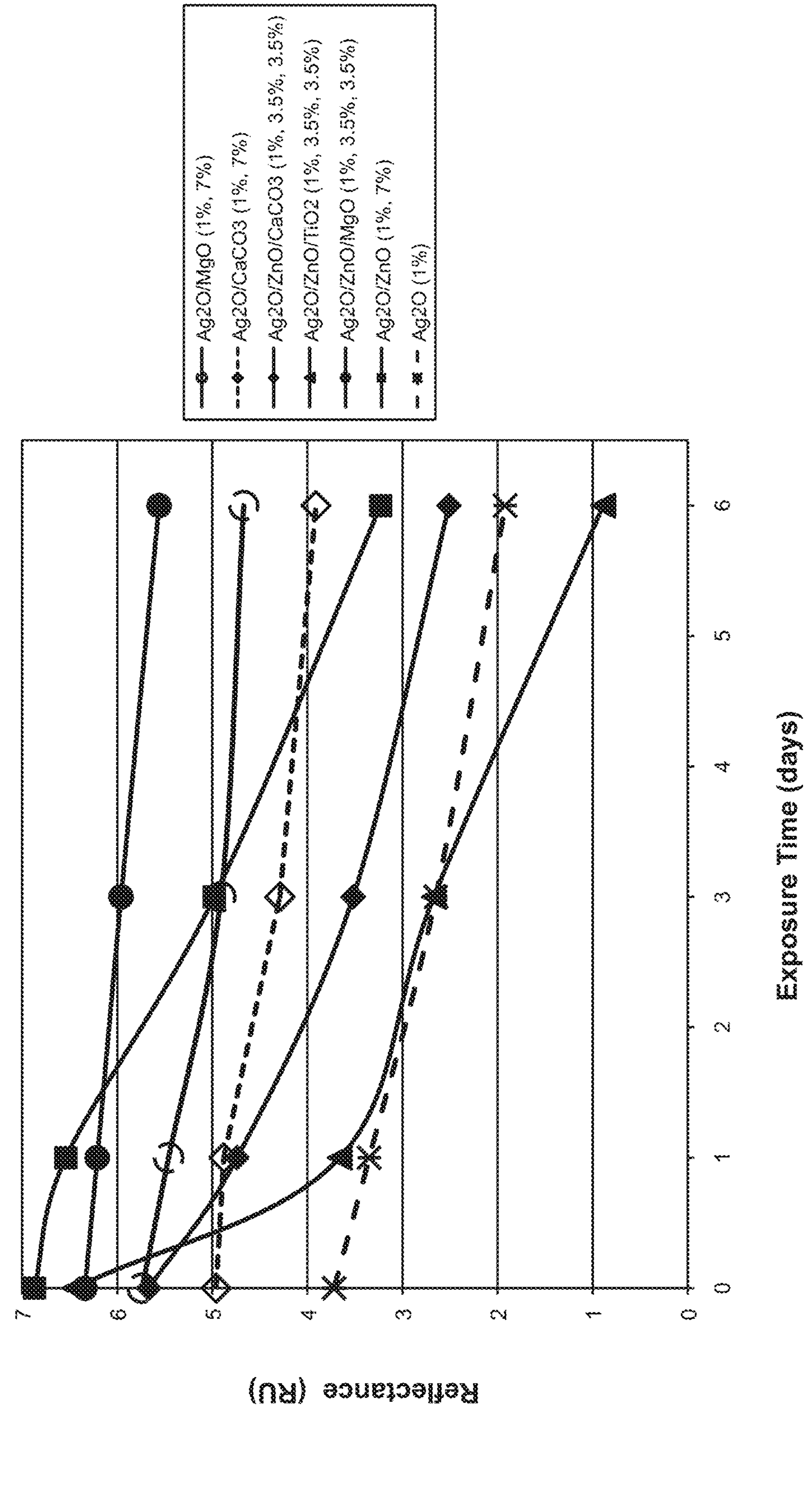
FIG. 12 is a graph plotting formulation whiteness, as a function of the exposure time to ultraviolet light, showing the whiteness stabilization performance of various inorganic substances in formulations containing $Ag_2O$ and ZnO.

FIG. 12 provides a graph plotting formulation whiteness, as a function of the exposure time to ultraviolet light; the graph demonstrates the whiteness stabilization performance of various inorganic substances in formulations containing $Ag_2O$ and ZnO. The decrease in whiteness of the $Ag_2O$/ZnO control or base formulation (1% $Ag_2O$/7% ZnO), as a function of UV exposure time, may be more pronounced than the corresponding decrease in whiteness of the identical $Ag_2O$ formulation, without the zinc oxide (not shown). When half of the zinc oxide is replaced with titanium dioxide, the results are still very poor: after only one day of UV exposure, the whiteness value exhibited by the $Ag_2O$/ZnO/$TiO_2$ formulation (1% $Ag_2O$/3.5% ZnO/3.5% $TiO_2$) is more than 40% lower than the initial whiteness.

By sharp contrast, when half of the zinc oxide is replaced with magnesium oxide, the initial whiteness value is somewhat lower, but after three days of UV exposure, the whiteness value exhibited by the $Ag_2O$/ZnO/MgO formulation (1% $Ag_2O$/3.5% ZnO/3.5% MgO) is significantly higher than that of the $Ag_2O$—ZnO formulation (1% $Ag_2O$/7% ZnO). Surprisingly, the whiteness value stays fairly constant over the first three days of UV exposure. The whiteness value exhibited appears to be higher than the whiteness value (plotted in FIG. 12 as a reference line) of an $Ag_2O$/MgO formulation containing 1% $Ag_2O$, 7% MgO, and having no ZnO.

The $Ag_2O/ZnO/CaCO_3$ formulation (1% AgO/3.5% ZnO/3.5% $CaCO_3$) exhibits poor whiteness values when compared with both 1% $Ag_2O$/7% ZnO and with 1% $Ag_2O$/7% $CaCO_3$.

Typically, the inventive formulations contain up to 5% silver oxide or up to 3% silver oxide, by weight. More typically, the formulations contain 0.01% to 3% silver oxide. The ratio of the whitener (without zinc oxide) and the stabilization agent to the silver oxide, within the formulation, is typically at least 0.2:1, at least 0.3:1, at least 0.5:1, at least 1:1, at least 2:1, at least 3:1, at least 4:1, at least 5:1, at least 7:1, or at least 10:1, by weight.

In preparing the various formulations of the present invention, we have discovered that within a specified range of weight ratios and/or compositions, the silver oxide based formulation is highly spreadable, despite the presence of the chalky whiteners and/or stabilization agents. We have found that formulations containing more than 20-25%, by weight, of the whiteners and/or stabilization agents, may display poor spreadability, and may generally be less efficacious from an anti-microbial standpoint.

Thus, the inventive formulations may contain up to 20% by weight, of at least one whitener and/or stabilization agent, more typically, up to 17% by weight, and more typically, up to 15% by weight. The formulations may typically contain at least 0.2%, at least 0.5%, at least 1%, at least 2%, at least 3%, or at least 5%, by weight, of the whitener and/or stabilization agent. Most formulations contain between 2% and 15%, between 2.5% and 12%, or between 3% and 10%, by weight, of the whitener and/or stabilization agent.

When both a whitener (e.g., zinc oxide) and a stabilization agent (e.g., $Mg(OH)_2$ or MgO) are used, the formulations may typically contain at least 0.2%, at least 0.5%, at least 0.8%, at least 1%, at least 2%, at least 3%, or at least 5%, by weight, of the whitener, and more typically, between 0.8% to 10%, between 0.8% to 8%, or between 0.8% to 6%, by weight. The formulations may typically contain at least 0.2%, at least 0.5%, at least 0.8%, at least 1%, at least 2%, at least 3%, or at least 5%, by weight, of the stabilization agent, and more typically, between 0.8% to 8%, between 0.8% to 6%, or between 0.8% to 4%.

The ratio of stabilization agent to whitener may vary greatly, but is typically at least 0.1:1, at least 0.25:1, at least 0.5:1, at least 1:1, at least 2:1, at least 3:1, or at least 5:1, by weight. Typically, the ratio of stabilization agent to whitener may be up to 15:1, up to 12:1, up to 10:1, or up to 8:1, by weight.

Example 47

The exemplary "standard base" silver oxide formulations provided hereinabove were prepared according to the following general procedure: jojoba oil was heated to 80° C. Beeswax was introduced, and the material was mixed thoroughly during cooling to about 55° C. Palmarosa oil was added, followed by at least one of a silver (II) oxide (AgO) and silver (I) oxide (Ag2O). Where appropriate, a solid (acting as a whitener and/or stabilization agent) such as an inorganic powder was introduced along with the silver oxide, although practical considerations may suggest that the addition be made prior to the introduction of the silver oxide, or sometime thereafter.

Mixing may be maintained throughout, and during cooling of the mixture to 35° C.-40° C.

Alternatively or additionally, various base components that are known to those skilled in the art may be used, including petrolatum, polyethylene polymers (such as: oxidized polyethylene homopolymer (Honeywell A-C® 629)), mineral oil, coconut oil, xanthum gum.

In the exemplary formulations described hereinabove, the weight ratio of the jojoba oil to beeswax was about 5.5 to 1. The palmarosa oil content was about 0.04% of the jojoba oil content. The total content of the beeswax, jojoba oil, silver oxide, and one or more whiteners and stabilization agents, within the formulations, typically exceeded 99%.

Example 48

An exemplary general procedure for producing the inventive silver oxide based cream is as follows: a base material such as liquid wax ester (e.g., jojoba oil) is heated, preferably to around 80° C. Alternatively or additionally, various base components may be used, base components that will be known to those skilled in the art of topical formulation production, such as, but not limited to, petrolatum, polyethylene polymers (such as an oxidized polyethylene homopolymer (Honeywell A-C® 629)), mineral oils, coconut oil, and xanthum gum.

A thick base material (e.g., a wax such as beeswax, polyethylene polymers, or hydrogenated jojoba oil or the like) may be melted into the liquid wax ester or base material. The mixture may be mixed thoroughly as it is cooled, typically below about 60° C. An essential oil such as palmarosa oil may be added. Mixing may be continued as at least one of a whitener and a stabilization agent (both in the form of solid powders) is introduced. At least one silver oxide such as a silver (II) oxide or a silver (I) oxide is also introduced, before, after, or concurrently with the whitener and stabilization agent, and the mixing may be continued during cooling of the mixture to below about 40° C. The mixing may advantageously produce an intimately dispersed formulation in which the silver oxide and the whitener and/or stabilization agent may be distributed in a homogeneous or substantially homogeneous fashion within the carrier medium.

Example 48A

Water-based and emulsion-based formulations according to the present invention may be prepared according to the following exemplary procedure: to a container containing water or an aqueous solution may be added a viscosity-building agent (e.g., a smectite such as a bentonite or montmorillonite powder such as Gelwhite H, produced by Southern Clay Products, Inc., Gonzales, Tex.). Other viscosity-building clays, particularly clays in which the silicate layers are disposed in a sandwiched structure, may also be used. Other viscosity-building agents and thickeners may be used, e.g., carbomers. Preferably, such selected materials may exhibit good resistance to oxidation or chemical attack by the silver oxide or oxides.

The mixture is mixed or homogenized, typically for 0.5 to 2 hours. Silver(II) oxide and/or silver(I) oxide may be introduced at this stage of the processing. The whitener(s) and/or stabilization agent(s) may be introduced to the mixture, typically along with the silver oxide, or sometime therefore or thereafter. The oil and/or liquid wax ester (e.g., jojoba oil) may be introduced to the mixture during the mixing (e.g., blending or homogenizing).

Examples 49-54

Six formulations were prepared according to the general procedure provided above. The control formulation contained 1% AgO, 7% ZnO, and no additional whitener or stabilizing agent. The other five formulations contained various quantities of MgO, such that the total amount of zinc oxide and magnesium oxide equaled 7%. The composition of each formulation, along with the weight ratios of magnesium oxide to zinc oxide and magnesium oxide to silver oxide, are provided below in TABLE 11:

TABLE 11

| Formulation | COMPOSITION (Wt. %) AgO | ZnO | MgO | WEIGHT RATIOS MgO:ZnO | MgO:AgO |
|---|---|---|---|---|---|
| A (Example 49) | 1 | 7 | 0 | 0.00 | 0.00 |
| B (Example 50) | 1 | 6.3 | 0.7 | 0.11 | 0.70 |
| C (Example 51) | 1 | 4.9 | 2.1 | 0.43 | 2.10 |
| D (Example 52) | 1 | 3.5 | 3.5 | 1.00 | 3.50 |
| E (Example 53) | 1 | 2.1 | 4.9 | 2.33 | 4.90 |
| F (Example 54) | 1 | 0.7 | 6.3 | 9.00 | 6.30 |

About 1 gram of each of Formulations B-F was smeared on a piece of 100% white cotton cloth, which was then exposed to white UV light for about one month. Periodically, the cloth was examined for change in color, and photographed.

Figure 13A:
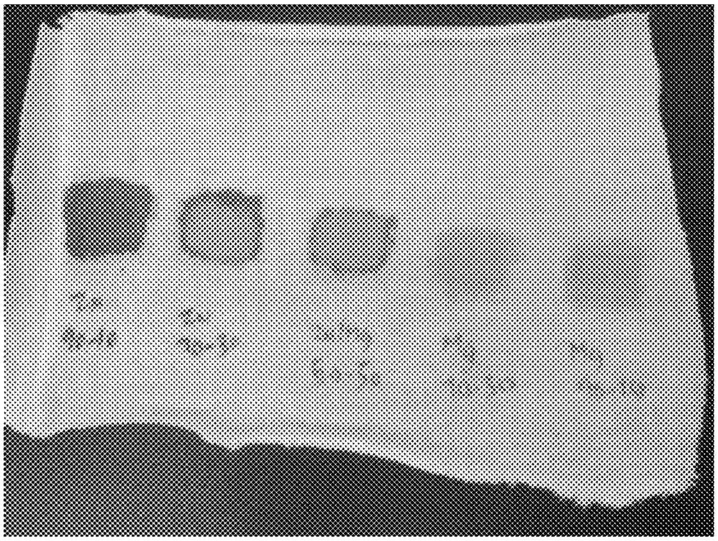
FIGS. 13A, 13B and 13C are photographs of a cloth stained with formulations of the present invention, after 3 days, 10 days, and 21 days of constant exposure to ultraviolet light.

FIG. 13A provides a photograph of Formulations B-F (ordered from left to right) after 3 days of constant exposure to UV light. It is clearly observed that staining or darkness is inversely related to the amount of MgO. Formulation B, though having a rather dark appearance, is actually lighter than Formulation A (not shown). The stain from Formulation C is dark solely near the perimeter; the stain associated with Formulation D is dark solely near a portion of the perimeter; the stains associated with Formulations D and E, respectively, are light throughout. Thus, as the content of MgO within the formulation becomes correspondingly higher, the staining appears to be lighter and less pronounced. It is further evident from the stains and from the data in TABLE 11 that reduced staining (or formulation lightness) may be proportionally related to, or may positively depend on, at least one of the weight ratio of MgO:ZnO and MgO:AgO.

Figure 13B:
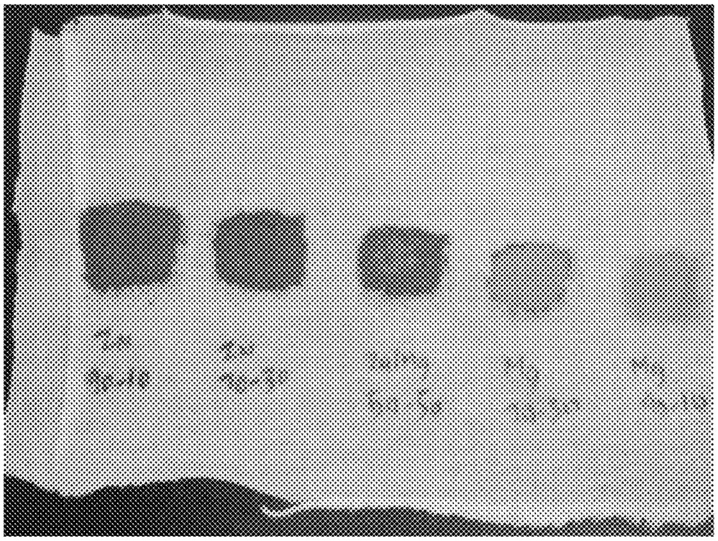
Figure 13C:
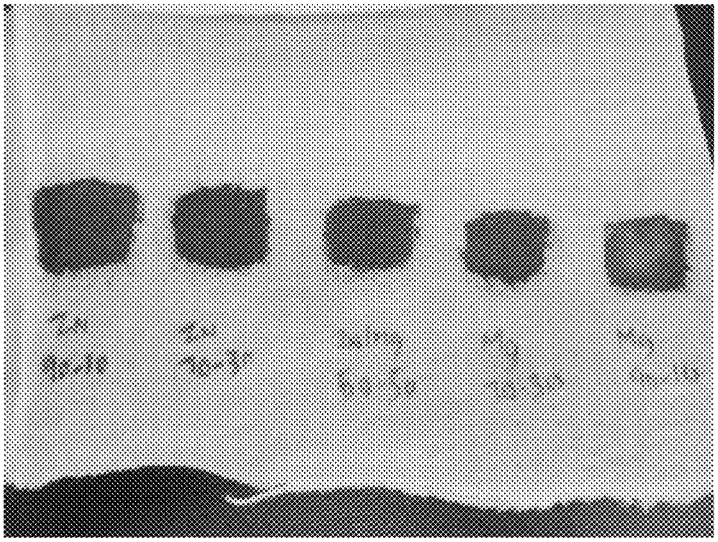

These observations may be further supported by the photographs of the stains provided in FIGS. 13A and 13B, taken 10 days and 21 days, respectively into the experiment. As before, the cloth underwent constant exposure to UV light. After 10 days, Formulation D is lighter than Formulation B after 3 days. Even after 21 days, Formulation F is lighter than Formulation B after 3 days.

Perhaps more significantly, all of the formulations containing MgO appear to be lighter than corresponding Formulation A, which contains no MgO.

Example 55

Formulation reflectance, lightness, or whiteness was evaluated as follows: approximately 1 gram of a particular sample (typically an ointment or cream) was spread on a 5 cm by 5 cm area of white cotton cloth and distributed evenly, typically using a metal spatula.

A LabScan XE spectrophotometer instrument (HunterLab, Va.) was used to evaluate the reflectance of each sample. The working principle of the instrument pertains to the property of light reflection. The cloth sample is stored in a completely dark container. To measure the reflectance, the instrument exposes the sample to a controlled, repeatable pulse of light. The lightness of the sample is generally correlated with the reflectance: higher values correspond to lighter samples.

The spectrophotometer has a wavelength range of 375 nm to 750 nm and an optical resolution of 10 nm. The spectrophotometer measures reflected color using 0°/45° geometry.

Example 56

Formulation reflectance was evaluated as a function of the exposure time to ultraviolet light, as follows: the LabScan XE spectrophotometer described in Example 9 was used. Each sample was continuously exposed to ultraviolet light produced by the illumination source. The continuous UV exposure is through a 254 nm, 6 W UV bulb distributed by Cole-Parmer®. The distance between the UV source and the specimen or formulation was 18 inches (~45.7 cm).

Sample preparation was substantially the same as that described in Example 55. After an initial measurement ("day 0"), additional measurements were made over the course of the exposure to ultraviolet light, typically on days 1, 3 and 6.

Examples 57-61

Five formulations were prepared according to the general procedure provided above. All the formulations contained 1% AgO, and were distinguished by their varying concentrations of MgO. Example 49 is provided for comparative purposes. The composition of each formulation, along with the weight ratios of magnesium oxide to silver oxide, are provided below in TABLE 12:

TABLE 12

| Formulation | COMPOSITION (Wt. %) AgO | ZnO | MgO | WEIGHT RATIO MgO:AgO |
|---|---|---|---|---|
| G (Example 49) | 1 | 7 | 0 | 0.0 |
| H (Example 57) | 1 | 0 | 0 | 0.0 |
| I (Example 58) | 1 | 0 | 3.5 | 3.5 |
| J (Example 59) | 1 | 0 | 7.0 | 7.0 |
| K (Example 60) | 1 | 0 | 14 | 14 |
| L (Example 61) | 1 | 0 | 28 | 28 |

Figure 14:
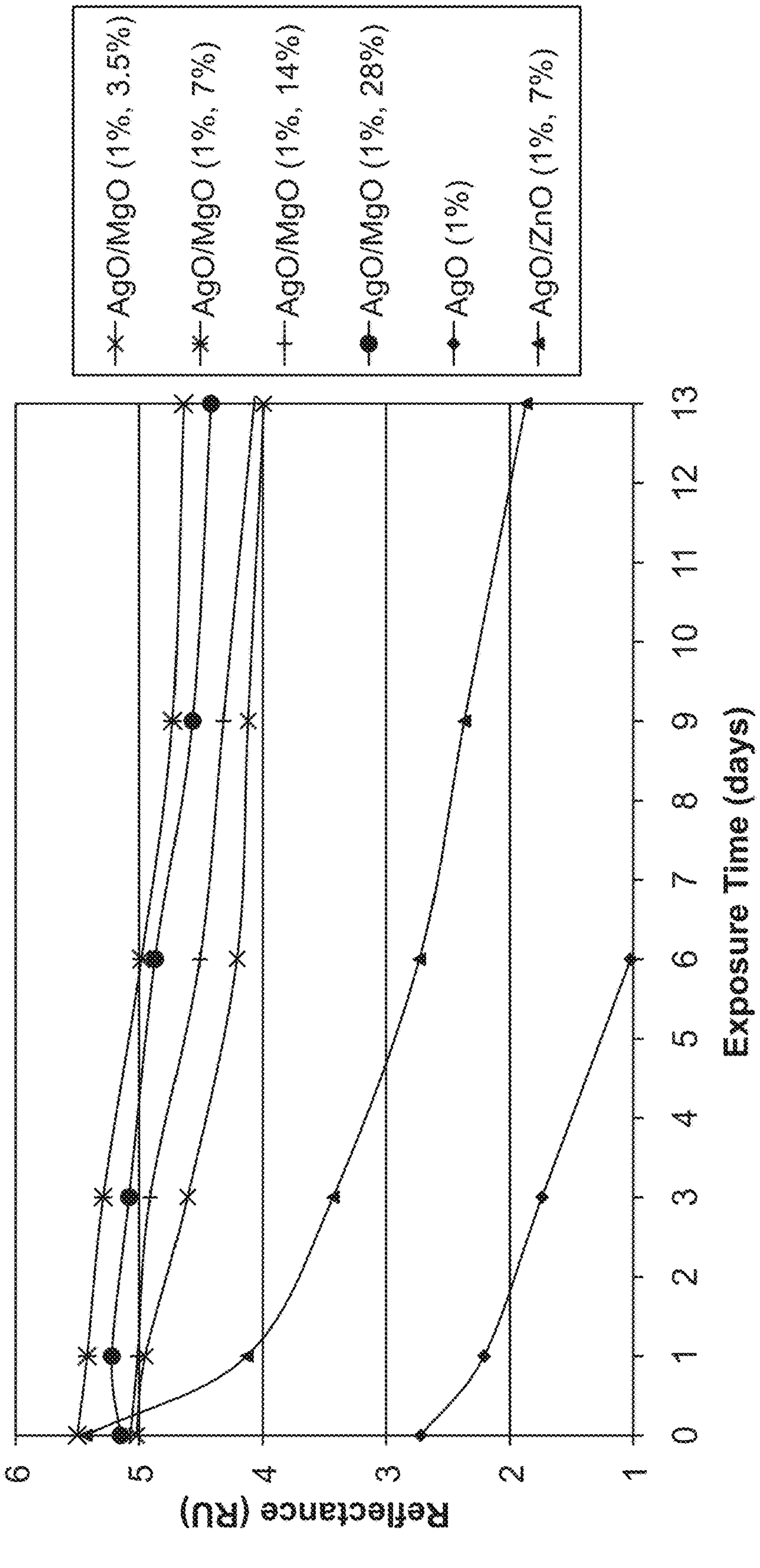
FIG. 14 is a graph plotting formulation whiteness, as a function of the exposure time to ultraviolet light, for formulations containing AgO and varying concentrations of MgO, versus similar formulations containing solely AgO, and AgO and ZnO.
Figure 14A:
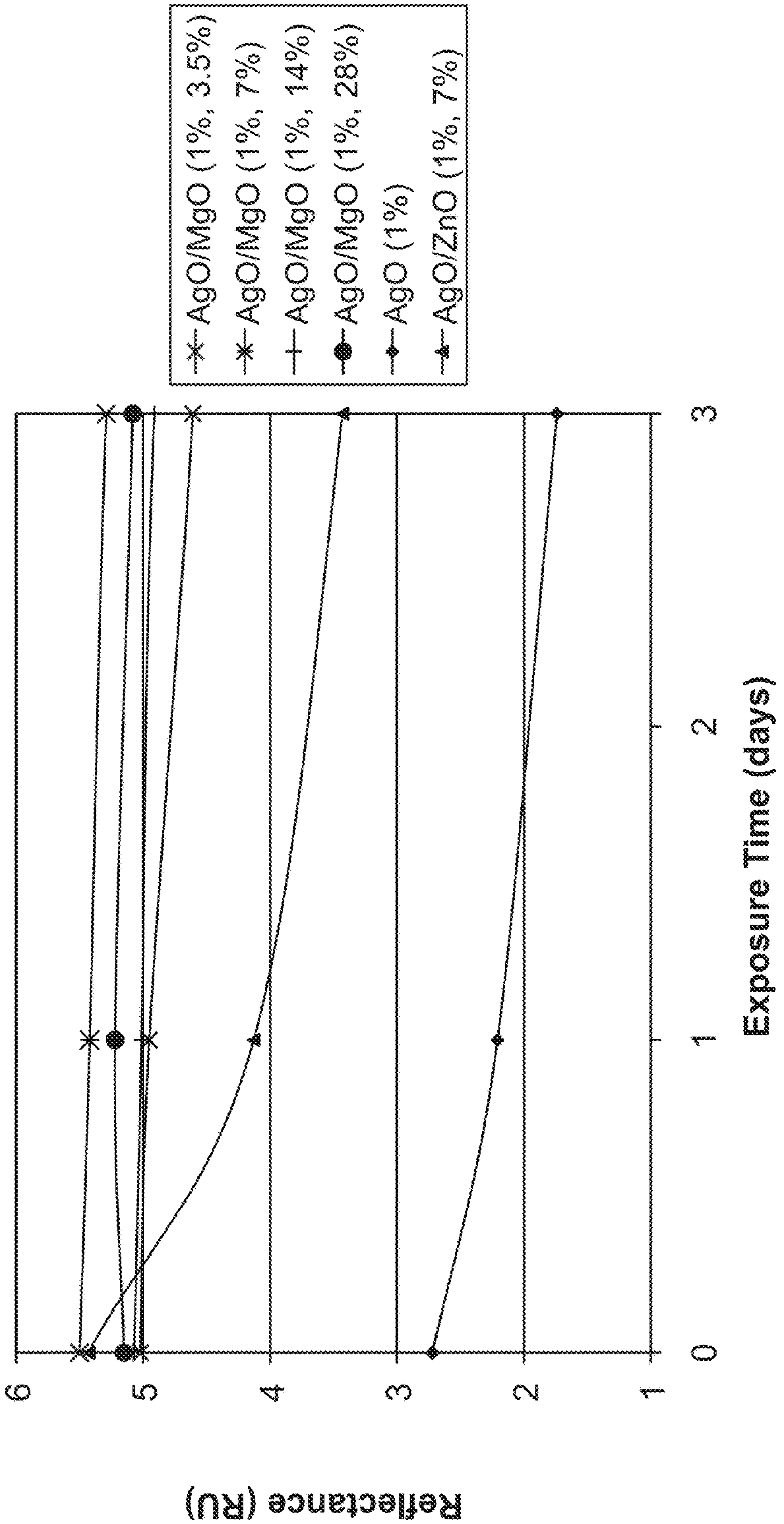
FIG. 14A presents a magnified, partial view of the graph of FIG. 14, showing exposure times of up to 3 days.
Figure 14B:
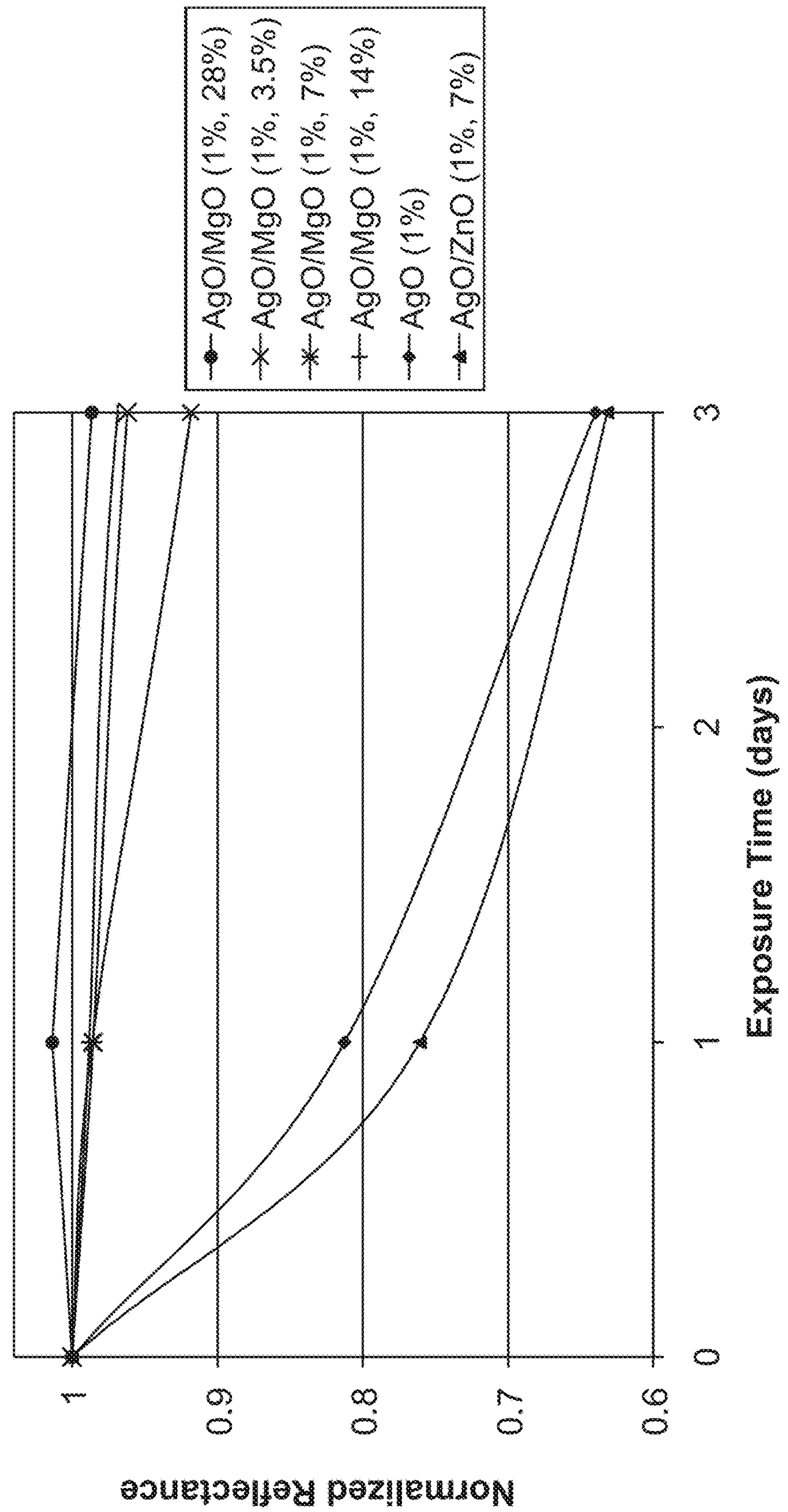
FIG. 14B provides a graph plotting normalized formulation whiteness (WN) as a function of the exposure time to ultraviolet light, for the formulations of FIG. 14A.

FIG. 14 is a graph plotting formulation whiteness, as a function of the exposure time to ultraviolet light, for formulations containing AgO and varying concentrations of MgO, versus similar formulations containing solely AgO (Example 11), and AgO and ZnO (Example 49). FIG. 14A is a magnified, partial view of the graph of FIG. 14, showing exposure times of up to 3 days. FIG. 14B provides a graph plotting normalized formulation whiteness (WN) as a function of the exposure time to ultraviolet light, for the formulations of FIG. 14A.

We observe that in all of the formulations containing MgO, the MgO behaved as a whitener and as a stabilizing agent. The initial whiteness values of the MgO-containing formulations were about 5 to 5.5 reflectance units. After one day of exposure to ultraviolet light, the whiteness values of the MgO-containing formulations dropped slightly, remaining close to or about 5 to 5.5 reflectance units. After three days of exposure to ultraviolet light, the whiteness values of the MgO-containing formulations dropped slightly, to about 4.6 to 5.3 reflectance units. After thirteen days of exposure to ultraviolet light, the whiteness values of the MgO-containing formulations dropped slightly, to about 4.0 to 4.6 reflectance units.

In FIG. 14B, we observe that after three days of exposure to ultraviolet light, the MgO-based formulations retained between 92% and 98% of their initial whiteness values. Formulation L, containing a 28:1 ratio of MgO to AgO, retained approximately 98% of its initial whiteness value; Formulation K, containing a 14:1 ratio of MgO to AgO, retained approximately 97% of its initial whiteness value; Formulation J, containing a 7:1 ratio of MgO to AgO, retained approximately 96% of its initial whiteness value; and Formulation I, containing a 3.5:1 ratio of MgO to AgO, retained approximately 92% of its initial whiteness value. Another formulation, containing a 1:1 ratio of MgO to AgO, retained almost 80% of its initial whiteness value, after three days of exposure to ultraviolet light. Moreover, even a formulation containing a 0.5:1 ratio of MgO to AgO acted as a stabilization agent over the course of at least one day of exposure to ultraviolet light.

All of these results are exceptionally good when compared with Formulation G, containing a 7:1 ratio of ZnO to AgO, which retained only about 63% of its initial whiteness value, after three days of exposure to ultraviolet light.

Example 62

Silver oxide formulations were prepared according to the general procedure provided in Example 48A. The active ingredients were:

silver(II) oxide (0.05% to 1.5%);
zinc oxide (1% to 11.3%);
at least one additional whitener or stabilization agent (1% to 9% magnesium hydroxide, calcium hydroxide, bentonite, calcium carbonate, magnesium oxide, magnesium carbonate, or magnesium sulfate).

Carrier ingredients were selected from beeswax, benzoic acid, bentonite, dimethicone, glycine, soybean oil, methylparaben, microcrystalline wax, mineral oil, panthenol, propylene glycol, propylparaben, sodium hydroxide, sorbitan sesquioleate, tocopheryl acetate, and water. A minute amount of fragrance was added to some of the formulations.

The silver(II) oxide based formulations generally exhibited an off-white or light gray appearance, suitable for topical formulations.

Example 63

Silver oxide formulations were prepared according to the general procedure provided in Example 48A. The active ingredients were:

silver(I) oxide (at least 0.1% to 3%);
zinc oxide (1% to 8%);
at least one additional whitener or stabilization agent (1% to 9% magnesium hydroxide, calcium hydroxide, bentonite, calcium carbonate, magnesium oxide, magnesium carbonate, or magnesium sulfate).

The carrier ingredients were substantially the same as those used in Example 16.

The silver(I) oxide based formulations generally exhibited an off-white, light gray, or medium gray appearance, suitable for topical formulations.

Example 64

Silver oxide formulations were prepared according to the general procedure provided in Example 47. The active ingredients were:

silver(I) oxide or silver(II) oxide (0.05%);
zinc oxide (0.0375%);
magnesium oxide (0.01%; 0.0375%);

The carrier was the standard base described in Example 47. The ratio of whitener and stabilization agent to silver oxide was 0.2:1 and 0.75:1. The ratio of whitener (and stabilization agent to zinc oxide was 0.27:1 and 1:1. The ratio of total whitener, zinc oxide and stabilization agent to silver oxide was 0.95:1 and 1.5:1. Under these conditions, both the silver(I) and the silver(II) oxide based formulations exhibited a generally off-white to slightly beige off-white appearance, suitable for topical formulations.

Example 65

Silver oxide formulations were prepared according to the general procedure provided in Example 1. The active ingredients were:

silver(I) oxide or silver(II) oxide (0.01%);
zinc oxide (0.02%);
magnesium oxide (0.02%);

The carrier was the standard base described in Example 47. The ratio of whitener, zinc oxide and stabilization agent to silver oxide was 2:1. The ratio of whitener and stabilization agent to zinc oxide was 1:1. As in Example 18, both the silver(I) and the silver(II) oxide based formulations exhibited a generally off-white to slightly beige off-white appearance, suitable for topical formulations.

Example 66

Anti-microbial activity was evaluated indirectly using a Fisher educational spectrophotometer. This technique uses turbidity as an indicator of microbial growth.

Bacterial samples were grown in a Muller-Hinton broth. Upon inoculation with the microbe, 4-5 mg samples of the exemplary formulations were loaded on to a 6 mm sterile disc, dropped into the broth, and allowed to incubate for 24 hours. After a pre-determined time, the samples were introduced to the spectrophotometer and the optical density (OD) measured. The OD reflects the turbidity of a sample, or the relative transparency of a sample to light passing therethrough, to the light detector on the distal side. Increasing OD may be generally correlated with an increased concentration of microbes.

Example 67

Anti-microbial activity was evaluated using a Bel-Art Colony Counting System, Scienceware Colony Counting System Instrument. The colony counting system may be performed instead of, or complementary to, the above-described spectrophotometric method.

Bacterial samples were inoculated in Muller-Hinton broth and the anti-microbial formulations were loaded, as in the spectrophotometric test described in Example 57. After 24 hours, a drop of the media was taken and streaked on a Muller-Hinton agar plate. After the plates were inoculated for 24 hours, the number of colonies visible in the plates was counted. The number of colonies visible may be generally correlated with decreasing anti-microbial efficacy of the sample formulations.

Example 68

Figure 15:
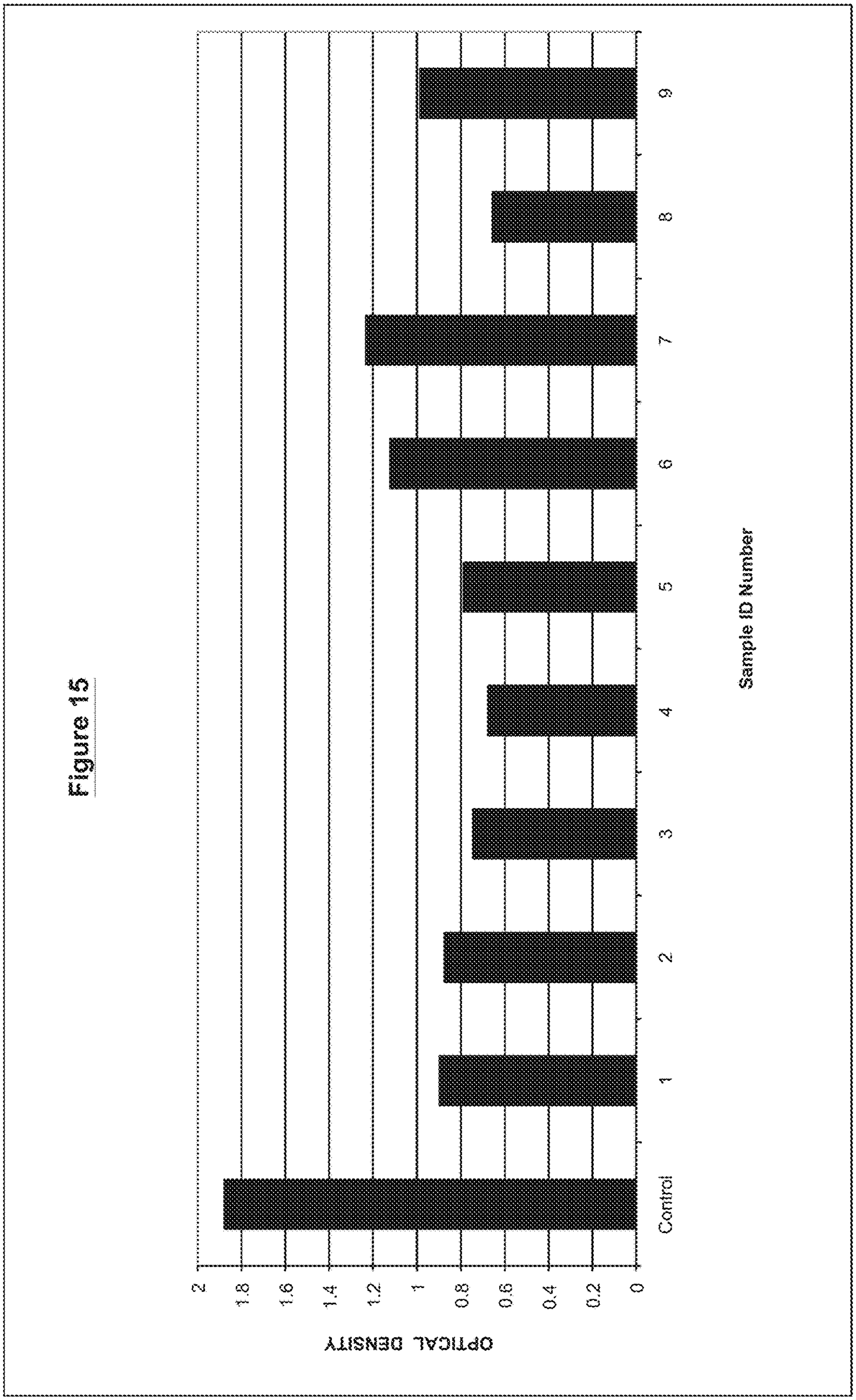
FIG. 15 is a bar graph showing the turbidity of a plurality of cultures, each culture containing a particular anti-microbial formulation.

FIG. 15 is a bar graph showing the turbidity of a plurality of cultures, each culture containing a particular anti-microbial formulation. One culture is a control culture, having no anti-microbial components. Sample 1 has no whitener, and no stabilizing agent. Samples 2-9 all contain an inorganic lightener or whitener. Some of these lighteners/whiteners may also act as a stabilizing agent that retards the discoloration process within the formulation.

All of the anti-microbial formulation containing cultures displayed pronounced anti-microbial activity. The least effective anti-microbial formulation was Sample 8, containing 1% $Ag_2O$ and 7% $TiO_2$. The most effective anti-microbial formulations were Samples 3-5 and 8, all containing 1% $Ag_2O$ and containing 7% of $Ca(OH)_2$, $Mg(OH)_2$, $MgCO_3$, or MgO, respectively.

TABLE 13

| Sample ID# | Sample Description | Optical Density |
|---|---|---|
| C | Control | 1.878 |
| 1 | AgO (1%) | 0.898 |
| 2 | AgO/$CaCO_3$ (1%, 7%) | 0.876 |
| 3 | AgO/$Ca(OH)_2$ (1%, 7%) | 0.745 |
| 4 | AgO/$Mg(OH)_2$ (1%, 7%) | 0.677 |
| 5 | AgO/$MgCO_3$ (1%, 7%) | 0.788 |
| 6 | AgO/Bentonite (1%, 7%) | 1.121 |
| 7 | AgO/$Ti_2O$ (1%, 7%) | 1.232 |
| 8 | AgO/MgO (1%, 7%) | 0.656 |
| 9 | AgO/$MgSO_4$ (1%, 7%) | 0.987 |

Example 69

Figure 16:
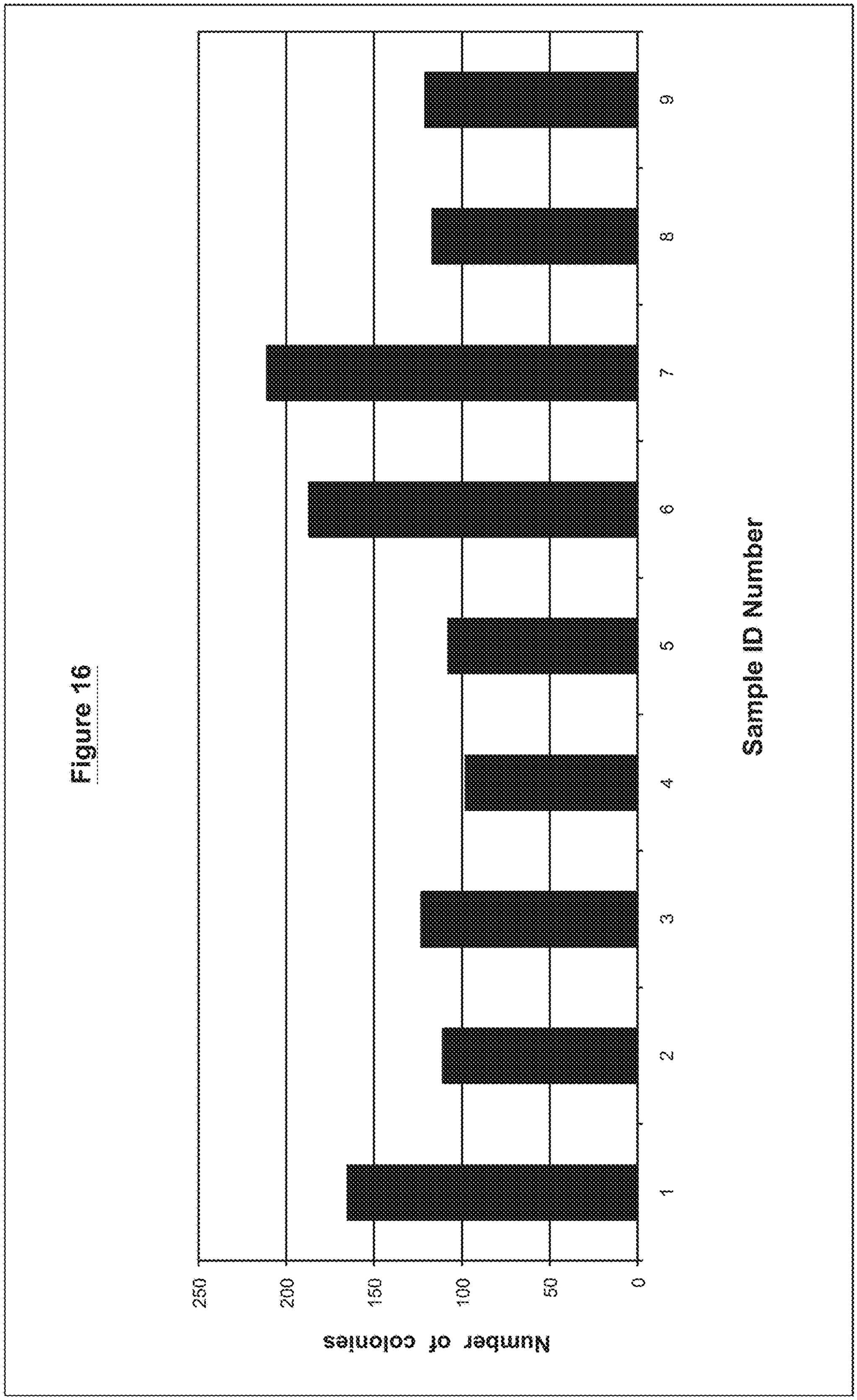
FIG. 16 is a bar graph showing the colony counts for the anti-microbial formulation containing cultures of FIG. 15.

FIG. 16 is a bar graph showing the colony counts for the anti-microbial formulation containing cultures of FIG. 15. The general trend is similar to the turbidity trend observed in Example 64. The most effective anti-microbial formulations were Samples 2-5, 8 and 9, all containing 1% $Ag_2O$ and containing 7% of $CaCO_3$, $Ca(OH)_2$, $Mg(OH)_2$, $MgCO_3$, MgO, or $MgSO_4$, respectively. As in Example 66, the least effective anti-microbial formulation was Sample 8, containing 1% $Ag_2O$ and 7% $TiO_2$.

TABLE 14

| Sample ID# | Sample Description | Number of colonies |
|---|---|---|
| 1 | AgO (1%) | 165 |
| 2 | AgO/CaCO3 (1%, 7%) | 111 |
| 3 | AgO/CaOH2 (1%, 7%) | 123 |
| 4 | AgO/MgOH2 (1%, 7%) | 98 |
| 5 | AgO/MgCO3 (1%, 7%) | 108 |
| 6 | AgO/Bentonite (1%, 7%) | 187 |
| 7 | AgO/Ti2O (1%, 7%) | 211 |
| 8 | AgO/MgO (1%, 7%) | 117 |
| 9 | AgO/MgSO4 (1%, 7%) | 121 |

Another first aspect of the present invention relates to a solid or substantially solid formulation or medical device, typically having a putty-like consistency, which may be particularly efficacious as a topical antibiotic in various applications. Such formulations or medical devices may exhibit superior oxidative stability and superior phase stability, along with efficacy in the inhibition, treatment and cure of various dermatological conditions. This formulation may be particularly efficacious in the treatment of bedsores, diabetic ulcers such as diabetic foot ulcers, puncture wounds, and the like.

The inventive putty formulation may include at least one viscosity-building agent, typically including a hydrophilic clay or smectite such as bentonite or hectorite, or an organoclay such as a bentonite or hectorite organoclay, a humectant, typically including an oil or liquid wax ester such as jojoba oil, and a base liquid, typically water or an aqueous solvent. The formulation may advantageously include an absorbefacient.

The viscosity-building agent may include, largely include, predominantly include, or consist essentially of a flour (such as wheat flour, corn flour, and/or rice flour) and/or a starch (such as corn starch or potato starch).

The formulation may advantageously include, in addition to an antibiotic agent, at least one preservative adapted to inhibit bacterial and/or fungal growth within the putty formulation. Preferably, the preservative, or combination of preservatives, should be effective against bacteria, molds and yeasts. Such preservatives may include at least one of benzoic acid, salicylic acid, and various parabens. While various preservatives are known to those of ordinary skill in the art of cosmetic and pharmaceutical formulations, it will be appreciated that the chemical compatibility with silver(II) and silver(I) oxide must be tested, for those formulations containing such silver oxides.

Preferred antibiotics may include at least one silver oxide. Preferably, the inventive solid or substantially solid formulation may include a silver(II) oxide such as tetrasilver tetroxide, or a silver(I) oxide such as $Ag_2O$ or silver sulfadiazine. To benefit from the bacteriostatic and antibiotic properties of the silver(II) oxide, the formulation may contain, by weight, at least 0.025% of the silver(II) oxide, and more typically, at least 0.05%, at least 0.10%, at least 0.25%, or 0.25% to 3.5 or 4% thereof. To benefit from the bacteriostatic and bacteriocidal properties of the silver(I) oxide, the formulation may contain, by weight, at least 0.05% of the silver(I) oxide, and more typically, at least 0.10%, at least 0.25%, or 0.25% to 3.5% thereof.

In topical applications such as the treatment of chronic wounds and acute wounds, the inventive formulation preferably exhibits particular mechanical, physical, bacteriocidal, palliative, moisturizing, and skin-protecting or skin-building properties. It is also essential that the various components of the formulation are biocompatible and are compatible with one another.

In some applications, it may be essential for the inventive formulation to be highly absorbefacient, in order to dry up fluid serving as a medium for microbial growth. However, we have found that a delicate balance may exist between inducing absorption and moisturization. Without a suitable moisturization agent or means, the absorption process may disadvantageously dry up the surrounding tissue, which may promote tissue irritation and skin cracking and induce pain, discomfort, and even additional infection. Moreover, we have found that the activity of various antibiotic agents (e.g., silver(II) oxide) may be compromised in dry environments, further constraining the balance between formulation absorption and moisturization.

To this end, we have found that the putty or plaster formulation of the present invention may advantageously include at least about 1%, at least about 1.5%, at least about 2.5%, at least about 3%, at least about 4%, and preferably, about 4% to 55%, about 4% to 50%, about 4% to 45%, about 5% to 40%, about 5% to 30%, or about 5% to 20%, by weight, of a humectant such as a liquid wax ester and/or an oil. The humectant may typically include, largely conclude, or consist mainly or predominantly of, a liquid wax ester such as jojoba oil. Additional humectants will be readily apparent to those of ordinary skill in the art.

The humectant may serve to mitigate or otherwise counter the drying effect of the absorbefacient. At higher concentrations of humectant, the humectant may leak out, ooze out, or be otherwise discharged from the formulation, making the use of the formulation less clean and convenient for medical practitioners and he patient.

Typically, the putty formulation may include at least about 2%, at least about 5%, at least about 8%, at least about 12%, or at least about 20%, by weight, and preferably, about 2% to 50%, about 3% to 45%, or about 4% to 40%, by weight, of at least one such absorbefacient. In these concentrations, the absorbefacient may serve a dual function as a viscosity-building agent. Various phyllosilicates or clays, including smectites, sepiolite and palygorskite, or organoclays such as disteardimonium bentonite may advantageously behave both as an absorbefacient and as a viscosity-building agent. The smectite may include various natural and synthetic forms of bentonite, montmorillonite and hectorite. It may be appreciated by one of skill in the art that hectorite may be somewhat more potent than bentonite and montmorillonite as an absorbefacient and as a viscosity-building agent, on a per-weight basis, such that lower concentrations of hectorite may be used to achieve the desired results. Those of ordinary skill in the art may readily identify other absorbefacient substances that may be suitable for use in the formulations according to the present invention.

It must be emphasized that the inventive formulation may be therapeutically effective in the treatment of wounds and skin infections, even without an antibiotic agent. Without wishing to be bound by theory, the inventors believe that the absorbefacient nature of the formulation is efficacious in reducing the moisture within the wound cavity, negatively impacting the growth environment of the microorganisms.

The inventive putty formulation may further include a skin-protecting or skin-building agent. Typically, the formulation may advantageously include at least 0.2%, and more typically, 1% to 15% or 2% to 10%, by weight, of the skin-protecting or skin-building agent. One presently preferred agent is zinc oxide.

The solvent typically includes water. Water may constitute at least 2%, at least 5%, at least 10%, at least 25%, at least 35%, or at least 40%, by weight, of the inventive formulation, and more typically, about 40 or 45% to 75%, or about 50% to 70% thereof.

We have discovered that with regard to various formulations of the present invention, a high weight ratio of the smectite (or more generally of the total weight of the at least one viscosity-building agent and absorbefacient) to the at least one antibiotic (e.g., $Ag_2O$, a silver(II) oxide such as tetrasilver tetroxide, or Bacitracin, Neomycin and the like) may not reduce the anti-microbial efficacy of the formulation. Weight ratios of up to 600:1 (smectite to antibiotic such as silver(II) oxide), up to 250:1, up to 100:1, up to 50:1, or up to 25:1 may display no decrease in anti-microbial efficacy (relative to substantially identical formulations having no smectite content) with respect to various skin-related microorganisms.

In many formulations of the present invention, the weight ratio of the smectite (or more generally of the total weight of the at least one viscosity-building agent and absorbefacient) to the at least one antibiotic is at least 0.2:1, at least 0.5:1, at least 1:1, at least 2:1, at least 5:1, at least 10:1, at least 20:1, or at least 50:1.

Bentonite, montmorillonite and hectorite are presently preferred smectites.

With particular regard to the putty formulations (including thick, viscous plaster formulations) of the present invention, the putty formulation may have a weight ratio of at least one viscosity-building agent and absorbefacient (e.g., a smectite) to the at least one antibiotic (e.g., silver(II) oxide) of at least 5:1, and more typically, about 5:1 to 200:1, about 5:1 to 75:1, or about 10:1 to 60:1.

In the putty formulation of the present invention, the weight ratio of the at least one viscosity-building agent and absorbefacient to at least one humectant (e.g., jojoba oil) may be at least 0.25:1, at least 0.4:1, at least 0.6:1, at least 1:1, and more typically, about 1.5:1 to 5:1, about 2:1 to 5:1, or about 2:1 to 4:1.

The inventive putty formulation may have various rheological properties that are particularly suited to various topical applications. For example, the putty may have an overall flexibility that is sufficient to enable molding of the putty to conform or largely conform to the shape of various surfaces. For example, a cavity of a wound or bedsore may be filled or partially filled with the inventive putty, whereby the putty conforms to the shape of the cavity. The putty may be inserted into the wound cavity as an integral piece, or as integral pieces. The putty may exhibit sufficient rigidity or stiffness to maintain its position over time (e.g., at least 1 hour, at least 2 hours, at least 4-12 hours, at least 24 hours, at least 48 hours, or at least 72 hours), within such a cavity, without oozing out, falling out, etc. The putty may exhibit sufficient rigidity or stiffness even as the temperature of the putty increases from room temperature to the temperature within the wound of the patient (human or animal).

The inventive putty formulation may advantageously be adapted to retain its integrity within the wound cavity, whereby the putty may be removed as an integral piece after at least 1 hour, at least 2 hours, at least 4 hours, or even after at least 24-72 hours.

The putty formulation may be rheologically adapted to apply a gentle and/or constant pressure against the surrounding tissue. While such pressure contact may promote improved contact between the antibiotic agent and the microorganisms, the contact may, in medical devices and techniques of the prior art, result in sticking of the medical device (e.g., gauze) to the wound surface. Absorbefacients pressure-contacted with a wound surface may excessively dry out the surface. Such effects may adversely affect wound healing, and may subject the patient to discomfort or acute pain. Absorbefacients pressure-contacted with the wound surface may also disintegrate or stick to the wound surface.

By sharp contrast, the inventive formulation may be adapted to remain integral within the wound cavity, to pressure-contact the wound surfaces without sticking thereto, and to be removed with facility from the wound. The formulation may be loaded with sufficient humectant, whereby excessive drying out of the wound surface is avoided, even over several days of continuous presence within the wound cavity.

Various rheological properties of the inventive putty formulation, such as viscosity and/or complex modulus (G*), may be generally maintained between room temperature (about 20-22° C.) and body temperature (about 32-35° C.). This may not be true for various materials or carriers based on petroleum, by way of example. Thus, the formulation components may be selected, and the formulation may be prepared, whereby the melting temperature of the formulation as a whole, is at least 40° C., at least 45° C., at least 50° C., or more typically, at least 75° C.

In characterizing the rheological properties of the present invention, we have found that the inventive formulation may have a large storage modulus (G') relative to the loss modulus (G"). Using a rotational rheometer such as a TA Instruments G2 rotational rheometer, we have found that the storage modulus, at any point or at substantially every point in the frequency range of 0.1 Hz to 1.0 Hz, may be at least $0.2\times10^4$ Pa, at least $0.5\times10^4$ Pa, at least $1.0\times10^4$ Pa, at least $2\times10^4$ Pa, at least $3.0\times10^4$ Pa, at least $4.0\times10^4$ Pa, at least $6.0\times10^4$ Pa, at least $9.0\times10^4$ Pa, or at least $12.0\times10^4$ Pa. At any point or at substantially every point in this frequency range, the storage modulus may be less than $1.2\times10^7$ Pa, less than $1.0\times10^7$ Pa, less than $8\times10^6$ Pa, or less than $7\times10^6$ Pa. More typically, the storage modulus may be within a range of $3.0\times10^4$ Pa to $1.0\times10^7$ Pa, within a range of $3.5\times10^4$ Pa to $9\times10^6$ Pa, within a range of $4.0\times10^4$ Pa to $7\times10^6$ Pa, or within a range of $5.0\times10^4$ Pa to $7\times10^6$ Pa.

In further characterizing these structural rheological properties, we have found that, at any point or at substantially every point in the frequency range of 0.1 Hz to 1.0 Hz, the loss modulus of the inventive putty formulation may be at least $0.1\times10^4$ Pa, at least $0.4\times10^4$ Pa, at least $0.5\times10^4$ Pa, at least $0.6\times10^4$ Pa, at least $0.8\times10^4$ Pa, or at least $1.0\times10^4$ Pa. At any point or at substantially every point in this frequency range, the loss modulus may be less than $5\times10^6$ Pa, less than $3\times10^6$ Pa, less than $2\times10^6$ Pa, or less than $1\times10^6$ Pa.

The ratio of the storage modulus to the loss modulus, at any point or at substantially every point in the frequency range of 0.1 Hz to 1.0 Hz, may be at least 1.0:1, at least 1.5:1, at least 2.0:1, at least 2.5:1, at least 3:1, at least 4:1, or at least 5:1. This ratio may be less than 12:1, less than 10:1, less than 9:1, or less than 8:1. The ratio of the storage modulus to the loss modulus may be in a range of 2.5:1 to 12:1, 3:1 to 10:1, or 4:1 to 9:1. Some formulations of the present invention have a storage modulus to loss modulus ratio of 4.5:1 to 7.5:1, or 5:1 to 7:1.

The complex modulus (G*), which is defined by the equation:

$$G^*=(G'^2+G''^2)^{1/2}$$

may be, at any point or at substantially every point in this frequency range, at least $0.3\times10^4$ Pa, at least $0.5\times10^4$ Pa, at least $0.7\times10^4$ Pa, at least $1.0\times10^4$ Pa, at least $2\times10^4$ Pa, at least $3.0\times10^4$ Pa, or at least $4.0\times10^4$ Pa, at least $6.0\times10^4$ Pa, at least $9.0\times10^4$ Pa, at least $12.0\times10^4$ Pa, or at least $12.0\times10^4$ Pa. At any point or at substantially every point in this frequency range, the complex modulus may be less than $1.2\times10^7$ Pa, less than $1.0\times10^7$ Pa, less than $8\times10^6$ Pa, or less than $7\times10^6$ Pa. More typically, the complex modulus may be within a range of $1.0\times10^4$ Pa to $1.0\times10^7$ Pa, within a range of $2.0\times10^4$ Pa to $1.0\times10^7$ Pa, within a range of $3.0\times10^4$ Pa to $1.0\times10^7$ Pa, within a range of $3.5\times10^4$ Pa to $9\times10^6$ Pa, or within a range of $4.0\times10^4$ Pa to $7\times10^6$ Pa.

At at least one point within the frequency range, the ratio of the storage modulus to the loss modulus is at least 1.5:1, at least 2.0:1, at least 2.5:1, at least 3:1, at least 4:1, or at least 5:1, and/or the ratio is less than 12:1, less than 10:1, less than 9:1, or less than 8:1.

Example 70

To a container containing water or more generally, an aqueous medium, is added at least one viscosity-building agent, typically a smectite (e.g., a bentonite or montmorillonite powder such as Gelwhite H, produced by Southern Clay Products, Inc., Gonzales, Tex.). The mixture is vigorously mixed or homogenized, typically for 0.5 to 2 hours, typically producing a single, viscous phase. The phase is typically homogeneous or substantially homogeneous. The oil and/or liquid wax ester (e.g., jojoba oil) may be introduced to the mixture during the mixing (e.g., blending or homogenizing), typically after the viscosity has been built. Mixing may be continued as the antibiotic (e.g., tetrasilver tetroxide) and various optional ingredients (e.g., skin builders) are introduced. Further mixing may ensue, typically for 5-30 minutes. Viscosity-building agents such as flours and starches may be introduced towards the end of the preparation process; a dough hook may advantageously be used for the subsequent mixing. The viscous formulation is typically homogeneous or substantially homogeneous.

Example 71

A putty formulation was prepared according to the procedure provided in Example 70. The putty contained included approximately 66% water, 24% bentonite, 9% jojoba oil, and 0.88% tetrasilver tetroxide.

Example 72

A putty formulation was prepared according to the procedure provided in Example 70 The putty contained included approximately 65% water, 23% bentonite, 9% jojoba oil, 2% zinc oxide, and 0.88% tetrasilver tetroxide.

Example 73

A putty formulation was prepared according to the procedure provided in Example 70. The putty contained approximately 53% water, 37% bentonite, 9% jojoba oil, and 0.88% tetrasilver tetroxide.

Example 74

A putty formulation was prepared according to the procedure provided in Example 70. The putty contained 53% water, 35% bentonite, 9% jojoba oil, 2% zinc oxide, and 0.88% tetrasilver tetroxide.

Example 75

A putty formulation was prepared according to the procedure provided in Example 70. The putty contained approximately 41% water, 3.4% bentonite, 14.2% jojoba oil, 41% flour, and 0.5% tetrasilver tetroxide. The putty was highly pliable and exhibited excellent phase stability.

Example 76

A putty formulation was prepared according to the procedure provided in Example 70. The putty contained approximately 47% water, 10% bentonite, 43% jojoba oil, and under 0.1% tetrasilver tetroxide. The putty formulation was designated as Sample 11010-1.

Example 77

A putty formulation was prepared according to the procedure provided in Example 70. The putty contained approximately 46% water, 34% bentonite, 13% jojoba oil, 5% zinc oxide, and 1% tetrasilver tetroxide. The putty formulation was designated as Sample 11010-2.

Examples 78-79

The putty formulations of Example 76 and Example 77 were subjected to rheological evaluation using a TA Instruments G2 rotational rheometer.

Small amplitude oscillatory rheometry was conducted on the provided samples, using a two-centimeter, stainless steel parallel plate geometry. To overcome sample-loading issues, the two samples were placed on the Peltier plate of the rheometer, and partially flatted with a flat Teflon® plate. Two one-millimeter shims were placed on either side of the sample, and a doctor blade was used to trim the sample to approximately 1000 micrometers. The two-centimeter parallel plate was then lowered onto the sample, achieving a gap distance between 1000 and 1050 micrometers.

The samples were initially subjected to a stress sweep at 1 Hz to identify the suitable oscillating torque for the frequency sweep based on waveform shape and the onset of non-linear viscoelastic behavior. Based on this work, a torque of 1000 μN-m was used for 11010-1, and 8000 μN-m for 11010-2.

Frequency sweeps were then conducted on both samples from 0.01 to 100 Hz at 25° C. and the indicated oscillating torques. Ten points were collected per decade of oscillating frequency. The run for sample 11010-1 showed inertial effects at frequencies above 16 Hz; as such, the data curve was truncated.

Both samples exhibit strongly elastic behavior in the regime tested, indicated by a large storage modulus G' relative to the loss modulus G". Sample 11010-1 is substantially less stiff than 11010-2 by approximately a factor of 60-70. At 1 Hz, sample 11010-1 had a storage modulus of $6.26\times10^4$ Pa, while sample 11010-2 had a storage modulus of $4.32\times10^6$ Pa. Both samples show a modest onset of a terminal zone at a frequency of approximately 0.03 Hz, followed by a quasi-plateau modulus. No strain hardening was observed in the achievable upper range of frequencies tested.

The complex modulus, G*, is the resultant vector of the storage and loss modulus. A higher complex or overall modulus indicates a stiffer material, requiring more force to deform the material a set amount. A material with a higher storage modulus relative to the loss modulus is more elastic and will therefore recover more than a material with a closer ratio; the ratio of the loss (G') to storage (G') modulus is reported as tan δ. A purely elastic material would have a tan δ=0, while a purely viscous material would have tan δ=∞. The comparison of these parameters at two frequencies is shown in Table 15.

Consistent with the discussion above, there is a large difference in modulus between samples 11010-1 and 11010-2, but only a modest frequency dependence in either sample. Also, the tan δ values are quite close between the two samples, indicating a similar relative level of elasticity, albeit requiring different levels of force to achieve the same degree of deformation. Both samples show a modest decrease in tan δ, indicating both materials become slightly more elastic with increasing frequency. It should be noted that this test subjects the sample to small amplitudes of deformation; larger degrees of deformation could require different levels of force, hence resulting in a different modulus, but the test implicitly assumes that the experiment is performed in the linear viscoelastic regime of the material.

Figure 17:
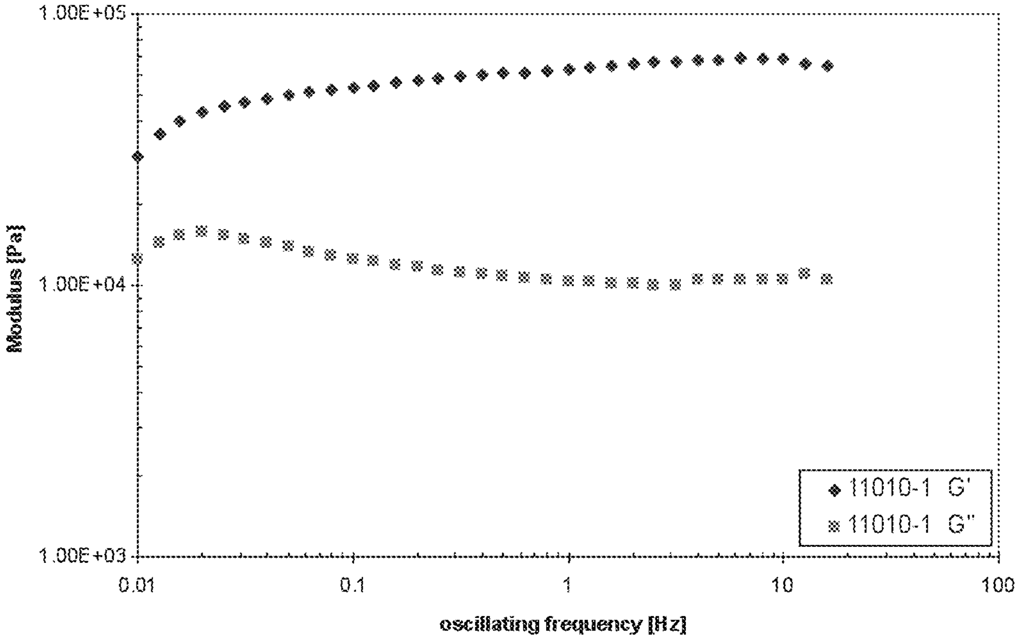
FIG. 17 provides a plot of the storage modulus G' and the loss modulus G", as a function of frequency, for a first formulation of the present invention.
Figure 18:
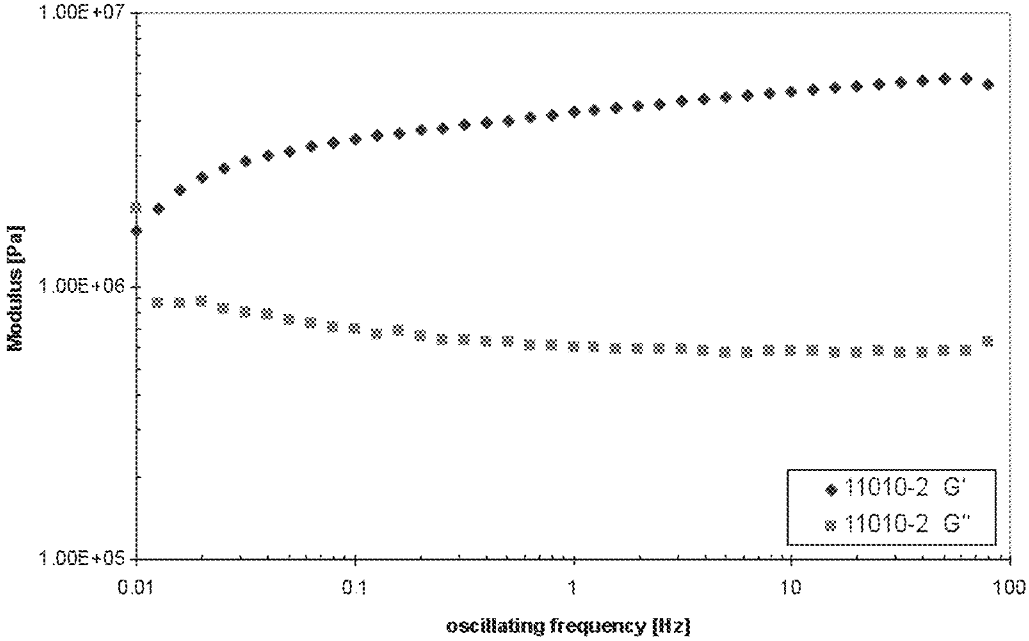
FIG. 18 provides a plot of the storage modulus G' and the loss modulus G", as a function of frequency, for a second formulation of the present invention.

With regard to samples 11010-1 and 11010-2, the storage modulus G' and the loss modulus G" are plotted in FIG. 17 and FIG. 18, respectively, as a function of frequency ("Frequency Sweep"). The values of G', G" and G* at 0.1 Hz and at 1.0 Hz are provided in Table 15 hereinbelow.

TABLE 15

| Sample | Frequency [Hz] | G' [Pa] | G" [Pa] | G* [Pa] | tan delta (δ) |
|---|---|---|---|---|---|
| 11010-1 | 0.1 | 5.37E+04 | 1.25E+04 | 5.51E+04 | 0.23 |
| | 1.0 | 6.26E+04 | 1.03E+04 | 6.34E+04 | 0.17 |

TABLE 15-continued

| Sample | Frequency [Hz] | G' [Pa] | G" [Pa] | G* [Pa] | tan delta (δ) |
|---|---|---|---|---|---|
| 11010-2 | 0.1 | 3.45E+06 | 6.92E+05 | 3.52E+06 | 0.20 |
| | 1.0 | 4.32E+06 | 5.99E+05 | 4.36E+06 | 0.14 |

Example 80

A putty formulation was prepared according to the procedure provided in Example 70. The putty contained 42.5% water, 3.3% bentonite, 13.8% jojoba oil, 39.9% flour, and 0.5% tetrasilver tetroxide. The putty was soft and slightly sticky, relative to the formulation of Example 75, but exhibited both high pliability and excellent phase stability.

Example 81

The putty formulation of Example 80 was subjected to rheological evaluation using a TA Instruments ARG2 rheometer.

Small amplitude oscillatory rheometry was conducted on the provided samples using a TA Instruments ARG2 rheometer. A two-centimeter, stainless steel parallel plate geometry was used to prevent the bridging effects that can occur in cone geometries when particle sizes might be significant. A gap of 1000 microns was used.

The samples were initially subjected to a torque sweep at 1 Hz to identify the suitable oscillating torque for the frequency sweep based on waveform shape and the onset of non-linear viscoelastic behavior. Based on this work, a torque of 1000 μN-m was determined.

A frequency sweep was then conducted on the sample, from 0.01 to 100 Hz at 25° C., using the oscillating torque amplitudes described above. Ten points were collected per decade of frequency.

Figure 19:
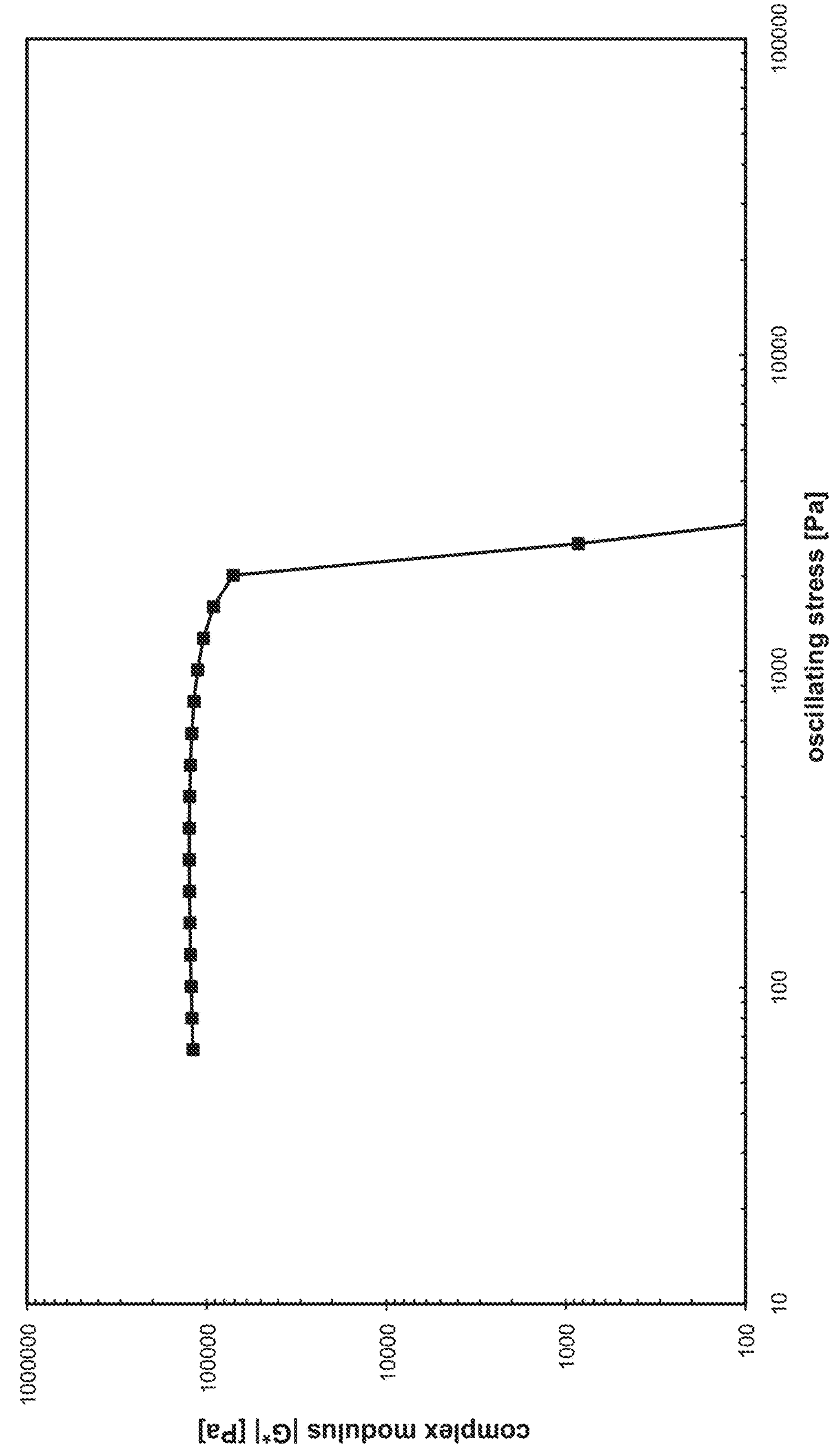
FIG. 19 shows a torque sweep as a function of the oscillating stress, for a third formulation of the present invention.

The results from the torque sweep are shown in FIG. 19. The sample showed non-linear behavior at approximately 2,000 Pa.

Figure 20:
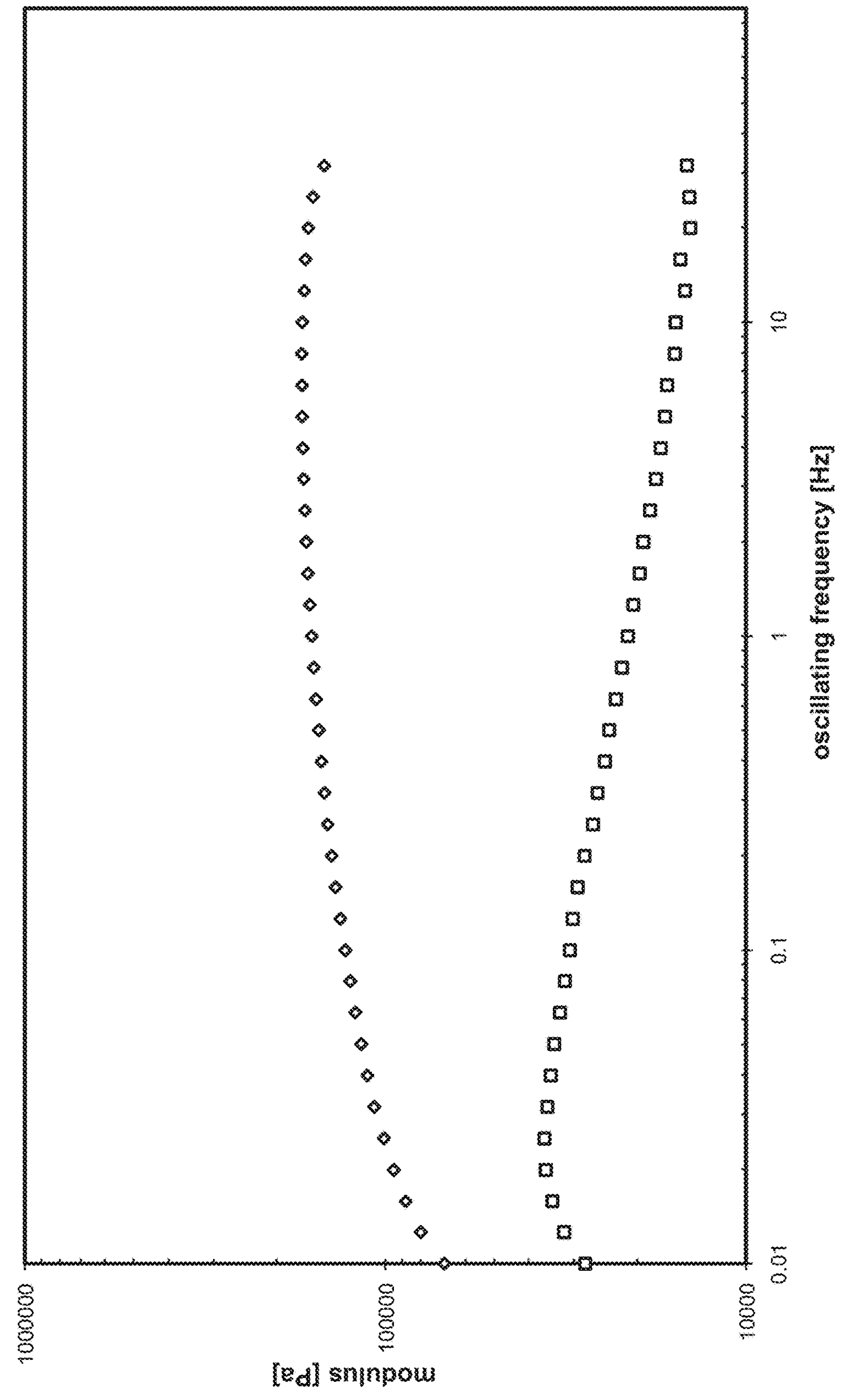
FIG. 20 provides a plot of the storage modulus G' and the loss modulus G", as a function of frequency, for the formulation of FIG. 19.

The frequency sweep data are plotted in FIG. 20. The sample exhibited a fairly flat modulus behavior, indicating little dependency on frequency.

This data is summarized at 3 frequencies (0.1 Hz, 1.0 Hz, and 10 Hz) in Table 16. The behavior of the sample was predominantly elastic, with the complex modulus ranging from about $1\times10^5$ to $2\times10^5$ Pa.

TABLE 16

| Sample | Frequency [Hz] | G' [Pa] | G" [Pa] | G* [Pa] | tan delta (δ) |
|---|---|---|---|---|---|
| 11264-2 | 0.1 | 1.29E+05 | 3.08E+04 | 1.33E+05 | 0.24 |
| | 1.0 | 1.60E+05 | 2.12E+04 | 1.61E+05 | 0.13 |
| | 10 | 1.70E+05 | 1.57E+04 | 1.71E+05 | 0.09 |

Example 82

A formulation was prepared according to the procedure provided in Example 70, containing 69.8% water, 9.3% bentonite, 8.1% jojoba oil, 9.3% flour, 3% zinc oxide, and 0.5% tetrasilver tetroxide. The formulation was soft, having a soft putty or plaster-like consistency, and exhibited both high pliability and excellent phase stability.

Example 83

A formulation was prepared according to the procedure provided in Example 70, containing 68.5% water, 18.3% bentonite, 7.9% jojoba oil, 4.8% zinc oxide, and 0.5% tetrasilver tetroxide. The formulation was soft, having a plaster-like consistency and exhibited both high pliability and excellent phase stability.

Example 84

The formulation of Example 82 was prepared according to the general procedure provided in Example 70, however, the mixing of the bentonite into the water was conducted for about 10 minutes. Despite having a composition substantially identical to that of Example 82, the formulation failed to develop the requisite viscosity or body. The formulation had a paste-like consistency, even after additional mixing time was provided after the silver oxide and zinc oxide were introduced.

Example 85

A formulation was prepared according to the procedure provided in Example 70, containing 65.4% water, 11.3% bentonite, 17.8% jojoba oil, 5% zinc oxide, and 0.5% tetrasilver tetroxide. The formulation was soft, exhibiting a plaster-like consistency and exhibited both high pliability and excellent phase stability.

Example 86

A putty formulation was prepared according to the procedure provided in Example 70, containing 40.6% water, 3.4% bentonite, 14.2% jojoba oil, 40.5% wheat flour, 0.5% tetrasilver tetroxide, 0.5% Allantoin, 0.1% Benzathonium Cl, and 0.5% Lidocaine.

Example 87

A putty formulation was prepared according to the procedure provided in Example 70, containing 39.0% water, 3.1% bentonite, 13.5% jojoba oil, 40.0% wheat flour, 0.5% tetrasilver tetroxide, 1.0% Clotrimazole, 5% salicyclic acid, and 0.1% colloidal oatmeal.

Example 88

The anti-microbial efficacy of various formulations was tested and compared using a Kirby-Bauer type test, as follows:

Ready-made Muller-Hilton agar was streaked with the bacterial inoculum using a sterile applicator. The sample was allowed to sit for 5 minutes to ensure that the bacteria adhere to the surface of the agar. Subsequently, an antibiotic sterile blank disc was pressed against a known quantity of the formulation being tested. Multiple duplicate discs were used to verify the data. The disc was pressed against the surface of the agar, making sure not to damage the disc or the agar. Each agar plate was then inverted and allowed to sit in the incubator at 37° C. for 24 hours. The plates were subsequently removed from the incubator, and the zone of inhibition was measured using a ruler.

The anti-microbial efficacy of eight formulations was tested and compared using the procedure detailed above, using Enterococcus faecalis.

Formulation Nos. 1-7 correspond to the formulations produced in Example Nos. 75, 80, 82, 83, 85, 86, and 87. Formulation No. 8 was a control formulation, produced according to the procedure outlined in Example 70. The control formulation was a putty containing: 40% water, 3.4% bentonite, 14.2% jojoba oil, and 40% wheat flour. No antibiotic was included in the control formulation.

Figure 21:
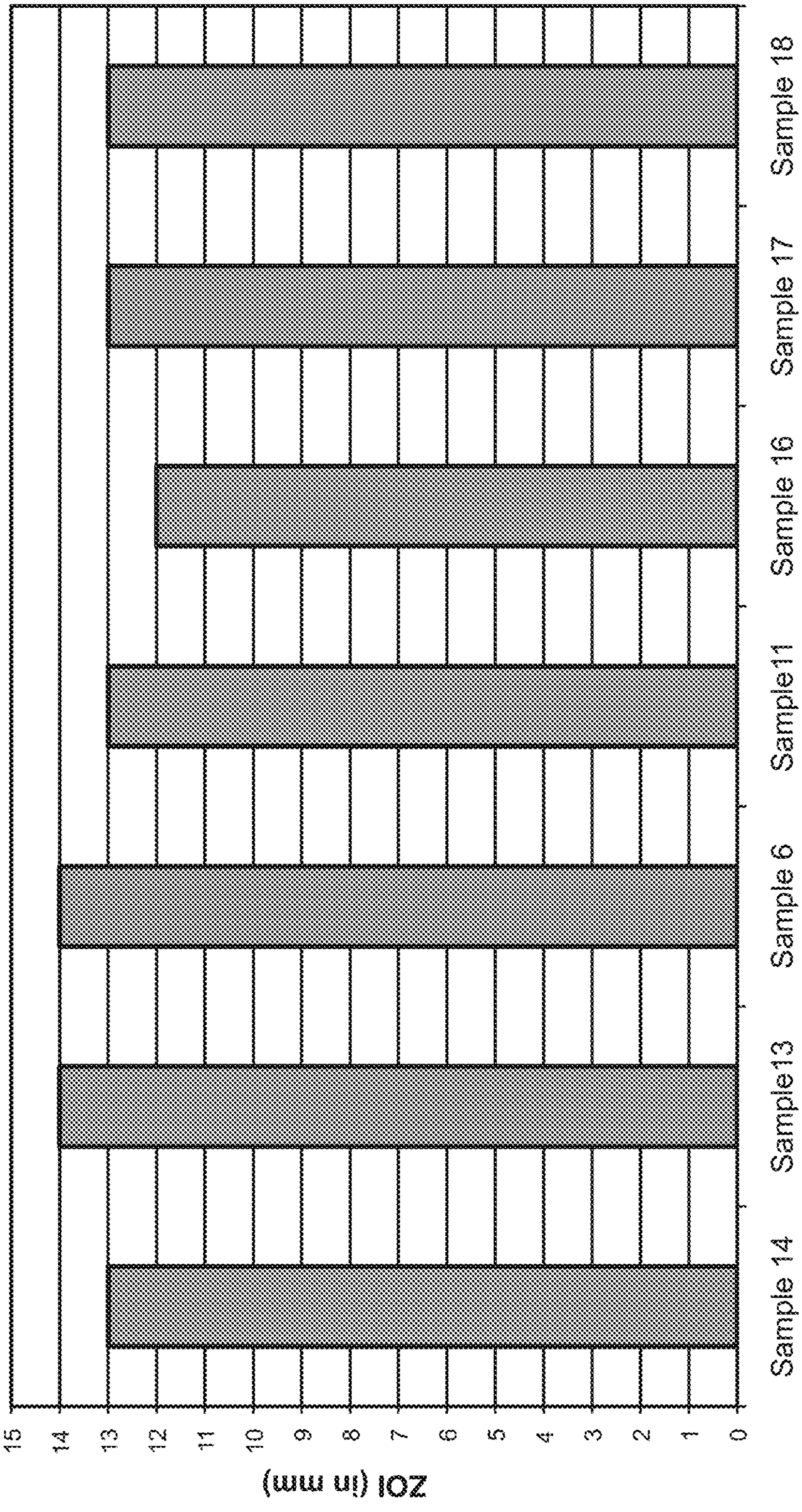
FIG. 21 provides bar graphs of the zones of inhibition of various formulation of the present invention.

The zone of inhibition for the control formulation was substantially 0 mm By sharp contrast, the zone of inhibitions for Formulation Nos. 1-7 all fell within a narrow range of about 12-14 mm (see FIG. 21). Such a large zone of inhibition may be considered a clear manifestation of the appreciable antibiotic activity of the inventive formulations, and was obtained using a low concentration of the silver oxide. Moreover, the large zone of inhibition may be especially noteworthy in view of the extremely high viscosities exhibited by the inventive putty formulations.

Examples 89-95

Formulations having compositions generally along the lines of Example 80, were prepared according to the procedure provided in Example 70. In Example 89, the putty contained 42.5% water, 3.3% bentonite, 13.8% jojoba oil, 39.9% flour, and 0.5% tetrasilver tetroxide, as in Example 11. The flour was a whole wheat flour. The putty was soft and slightly sticky, relative to the formulation of Example 75 but exhibited both high pliability and moldability, and excellent phase stability.

In Example 90, rice bran flour replaced the wheat flour, and the silver(II) oxide concentration was increased to 4%. To obtain a similar consistency as that obtained in Example 89, the ratio of filler (rice flour) to water was increased from 0.94 to 1.48, representing a 58% increase in filler, relative to the wheat flour of Example 89. The putty had a dark gray color, which may largely be due to the relatively high concentration of the silver(II) oxide. The putty was soft and slightly sticky, relative to the formulation of Example 75 and exhibited excellent phase stability. The formulation had a somewhat grainy appearance and was moldable, though less so than the putty of Example 89.

In Example 91, corn starch replaced the wheat flour of Example 89, while the silver(II) oxide concentration was maintained at 0.5%. To obtain a similar consistency as that obtained in Example 89, the ratio of filler (corn starch) to water was increased from 0.94 to 1.09, representing a 17% increase in filler, relative to the wheat flour of Example 89. The putty had a substantially white appearance. The putty was soft and slightly sticky, relative to the formulation of Example 75, and exhibited excellent phase stability. The formulation was moldable, though less so than the putty of Example 89.

In Example 92, potato starch replaced the wheat flour of Example 89, while the silver(II) oxide concentration was increased at 1.5%. To obtain a similar consistency as that obtained in Example 89, the ratio of filler (potato starch) to water was increased from 0.94 to 1.25, representing a 33% increase in filler, relative to the wheat flour of Example 89. The putty had a yellow tinge. The putty was soft and slightly sticky, relative to the formulation of Example 6, and exhibited excellent phase stability. The formulation was more grainy than the putty of Example 91 and was moldable, though less so than the putty of Example 89.

In Example 93, the whole wheat flour of Example 89 was used, but the silver(II) oxide was replaced by silver(I) oxide (0.5%). The appearance of the putty, consistency, and phase stability appeared to be identical, or substantially identical to those of the putty of Example 89.

In Examples 94 and 95 the putty formulation of Example 89 was prepared, again, according to the general procedure of Example 70. In each formulation, a different topical antibiotic material was used instead of the silver(II) oxide. The concentration of each antibiotic material was selected according to the concentration of the antibiotic material in commercially available ointments. Thus, in Example 94, the antibiotic material was clotrimazole, 1% by weight; in Example 95, the antibiotic material was erythromycin, 2% by weight. The appearance, consistency, and phase stability of the putties of Example 94 appeared to be identical, or substantially identical to those of the putty of Example 89.

Example 96

Fifty four patients were treated at Irvine3 Circulation/Vascular Labs (Chieti-Pescara University, Pescara, Italy). Patients were matched with other patients of similar age and similar general health condition, and having complex ulcers of similar type, size and severity. Effectively, 18 groups of three patients were formed for the purpose of comparative testing.

Within each group of three, a first patient was treated with conventional cleaning and compression management methods. A second patient within each group was treated with an ointment, containing approximately 0.9% silver(II) oxide and 6.8% ZnO in a beeswax and jojoba oil base. The ointment was applied around and at the edge of the ulcerated areas and on the ulceration, following the identical conventional cleaning methods used on the first patient.

The third patient within each group was treated with an antibiotic-containing putty of the present invention. The antibiotic, consisting essentially of tetrasilver tetroxide (silver(II) oxide), was dispersed within the putty, which had the composition of the putty described in Example 75, and was prepared according to the procedure provided in Example 70.

Figure 22:
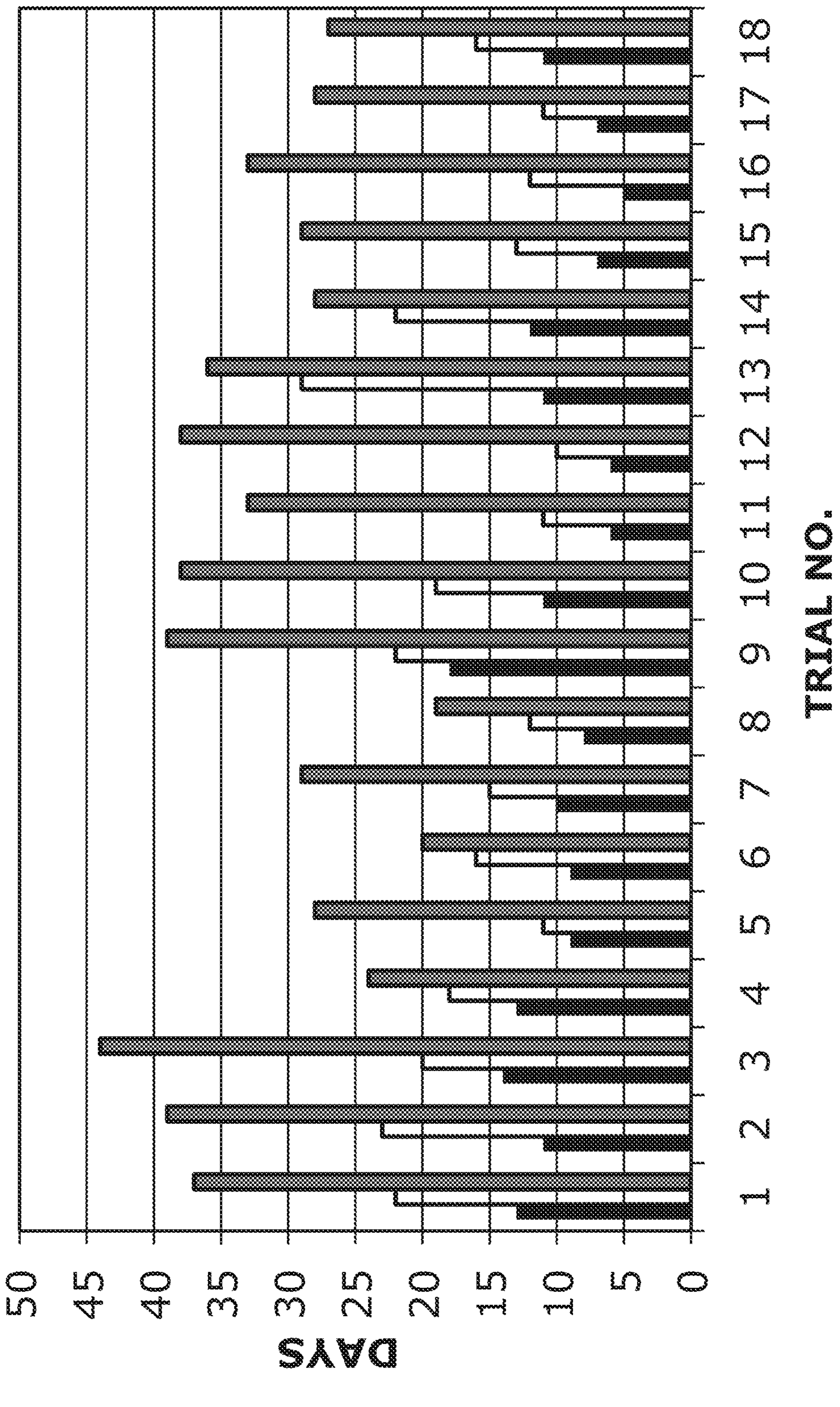
FIG. 22 provides bar graphs showing clinical wound closure data from comparative clinical trials in which the use of an exemplary putty of the present invention is tested against the use of a silver oxide ointment and against a conventional treatment protocol.

FIG. 22 provides bar graphs showing the wound closure data from each of the 18 comparative clinical trials. In FIG. 22, associated with each trial number are three juxtaposed bar graphs, the right-most of which represents the patient subjected to the conventional treatment, the middle bar graph represents the patient treated with the ointment containing the silver(II) oxide, and the left-most of which represents the patient treated using the formulation of the present invention.

On average, the complex ulcers treated by conventional means required over 31 days to close, on average. The complex ulcers treated with the silver(II) oxide based ointment required almost 17 days to close, on average, an appreciable improvement over the results for the control group. The complex ulcers treated with the antibiotic-containing putty of the present invention closed after just over 10.1 days, on average, about ⅓ of the time required for the wounds of the control group, and about 40% less time with respect to the excellent result achieved using the ointment. The performance of the inventive antibiotic putty is more surprising in view of the relatively low concentration of antibiotic (0.5% silver(II) oxide) in the putty, with respect to the concentration of the same antibiotic (~0.9% silver(II) oxide) in the antibiotic ointment formulation. The improved performance is even more surprising in view of past experience showing that for a given concentration of antibiotic material, more viscous formulations may considerably less efficacious from a bacteriocidal standpoint.

As used herein in the specification and in the claims section that follows, the term "antibiotic" refers to a substance that selectively attacks and destroys at least one species or type of microorganism, while exhibiting relative inertness with respect to human and/or mammalian cells. More typically the antibiotic substance selectively attacks and destroys at least one species or type of microorganism that commonly populates the skin, surface wounds, bedsores and the like, while exhibiting relative inertness, with respect to skin cells of humans and/or mammals. The term "antibiotic" is specifically meant to exclude anti-microbial preservatives, both anti-fungal preservatives and anti-bacterial preservatives. Such anti-fungal preservatives include, but are not limited to, compounds such as benzoic and ascorbic acids and salts thereof, and phenolic compounds such as methyl, ethyl, propyl and butyl p-hydroxybenzoate (parabens). Antibacterial preservatives include, but are not limited to, compounds such as quaternary ammonium salts, alcohols, phenols, mercurials and biguanidines. The term "antibiotic" is specifically meant to exclude anti-microbial preservatives such as table salt and the like, vinegar, sodium nitrate, sodium nitrite, and sulfites. The term "antibiotic" is specifically meant to include, without being limited to, silver oxides such as silver(I) oxide and silver(II) oxide, silver sulfadiazine, and any other topical antibiotics that are efficacious in the treatment of serious skin wounds such as bedsores, skin ulcers, and puncture wounds, or that are efficacious in the treatment of mundane skin wounds. The term "antibiotic" is specifically meant to include "classic" topical antibiotics such as Bacitracin, Neomycin, Erythromycin and Chloramphenicol. Additional topical antibiotic substances may be readily apparent to those of ordinary skill in the art.

As used herein in the specification and in the claims section that follows, the term "therapeutically effective amount", with respect to an antibiotic substance or formulation, refers to a quantity that produces a positive result in the treatment of at least one topical infection.

As used herein in the specification and in the claims section that follows, the term "therapeutically effective concentration", with respect to an antibiotic substance within a formulation or medical device, refers to a concentration of the antibiotic, within the formulation or medical device, which produces a positive result in the treatment of at least one topical infection.

As used herein in the specification and in the claims section that follows, the term "putty", with respect to a substance or formulation, is meant to refer solely to the physical consistency of the substance or formulation.

As used herein in the specification and in the claims section that follows, the term "plaster", with respect to a substance or formulation, is meant to refer solely to the physical consistency of the substance or formulation.

As used herein in the specification and in the claims section that follows, the term "silver (II) oxide" refers to a silver oxide whose unit structure contains silver and oxygen in a substantially 1:1 molar ratio. The term "silver (II) oxide" is specifically meant to include $Ag_4O_4$ (often represented as $Ag_2O_3.Ag_2O$) and AgO.

As used herein in the specification and in the claims section that follows, the term "whiteness value" may be represented by a luminance parameter L*, as specified by the International Commission on Illumination (Commission Internationale d'Eclairage, or CIE), and expressed as a percentage, wherein L*=0 represents black, and L*=100 represents diffuse white.

As used herein in the specification and in the claims section that follows, the term "whiteness value" or "reflectance value", with respect to a substance or formulation, may be represented by a reflectance value, in reflectance units, as determined by a LabScan XE spectrophotometer instrument (HunterLab, Va.), or the like. The spectrophotometer must be calibrated whereby the measured reflectance value of the following sample substances, is within 0.40 reflectance units, and preferably within 0.30 reflectance units or 0.20 reflectance units, of the respective measured reflectance values provided below:

| Sample ID | Cyan (C) | Magenta (M) | Yellow (Y) | Key (K) | Observed Color | Measured Reflectance Units (RU) |
|---|---|---|---|---|---|---|
| Sample A1 | 7 | 3 | 2 | 11 | Light gray | 5.21 |
| Sample A2 | 2 | 3 | 4 | 5 | Light gray | 5.67 |
| Sample A3 | 17 | 12 | 20 | 24 | Medium gray | 4.12 |
| Sample A4 | 22 | 14 | 9 | 31 | Medium gray | 4.55 |
| Sample A5 | 16 | 23 | 23 | 69 | Dark gray | 3.49 |

Typically, a light gray formulation exhibits a reflectance of at least about 4.8 RU; a medium gray formulation exhibits a reflectance in a range of about 3.8 to about 4.8 RU; a dark gray formulation exhibits a reflectance of less than about 3.8 RU, and typically between about 1.0 and 3.8 RU or between 2.0 and 3.8 RU.

As used herein in the specification and in the claims section that follows, the term "laundered white cloth" and the like refers to a white cloth swatch that has been stained and laundered substantially according to the staining and laundering procedure described hereinabove.

As used herein in the specification and in the claims section that follows, the term "initial whiteness value" with respect to a substance or formulation, refers to the whiteness value of the substance or formulation, prior to significant exposure to ultraviolet radiation. Typically, the initial whiteness value is measured within several minutes, or within an hour, from the time the substance or formulation is dispensed from its tube, vial, or the like.

As used herein in the specification and in the claims section that follows, the term "gray hue" and the like, with respect to a substance or formulation, is meant to include light gray, medium gray, dark gray, and off-white hues.

As used herein in the specification and in the claims section that follows, the term "stabilization agent" and the like, refers to a substance that retards or otherwise reduces the darkening of silver oxide formulations over time or over exposure to ultraviolet light. The term "stabilization agent" is meant to specifically exclude titania and zinc oxide.

As used herein in the specification and in the claims section that follows, the term "constant exposure to ultraviolet light" and the like relates to conditions identical or substantially identical to those delineated in Example 10, or to conditions determined and demonstrated by an expert in the art to yield identical or highly similar results with respect to the conditions delineated in Example 10.

The inventors have further discovered that a mixture of silver(II) oxide and silver(I) oxide may be appreciably more efficacious than is indicated by the Horsfal series provided hereinabove.

We have further discovered that under certain physical processing conditions, silver(II) oxide may be surprisingly converted to silver(I) oxide. In the conversion process, oxygen may be liberated, and/or a silver(III) oxide may be formed.

We have also discovered that under certain physical processing conditions, described hereinbelow, crystalline silver(II) oxide may be surprisingly converted to a semi-crystalline, irregular, and/or possibly amorphous silver oxide.

Thus, one aspect of the present invention relates to a silver-oxide based formulation or medical device that may be particularly efficacious in various bacteriostatic or bacteriocidal applications. Such formulations or medical devices may be efficacious in the inhibition, treatment and cure of various medical conditions, and in particular, dermatological conditions. The formulation or medical device may include a mixture of silver(II) oxide and silver(I) oxide, and/or a mixture of a crystalline silver(II) oxide and a silver oxide having a low degree of crystallinity.

An exemplary general procedure for producing oil-based silver(II) oxide formulations according to the present invention is as follows: an oil such as jojoba oil is heated, preferably to around 80° C. A wax such as beeswax may be melted into the oil. The material may be mixed thoroughly as it is cooled, typically below about 60° C. Optionally, an essential oil such as palmarosa oil may be added. Mixing may be continued as the fine silver oxide material is introduced, and further mixing may ensue, typically for 0.5 to 2 hours, during cooling of the mixture to below about 40° C. The formulation may then be poured into storage containers.

Typically, the formulations contain a total silver(II) oxide content of at least 0.01% or 0.02%, by weight, more typically, 0.05% to 3%, by weight, and yet more typically, 0.1% to 3% silver oxide. The silver oxide may predominantly consist of tetrasilver tetroxide ($Ag_4O_4$), or AgO.

Alternatively, water-based formulations or emulsion-based formulations may be produced. These formulations may typically contain 50-99% water, 0.5% to 30% of a thickening agent and/or an emulsifier, up to 60% jojoba oil, typically clear jojoba oil (usually 1-60%), and between 0.01% and 3% silver(II) oxide. Various clays, including members of the smectite family such as bentonite, may be used as the thickening agent.

The inventive materials may be incorporated in a medical device that may be particularly efficacious in various bacteriostatic or bacteriocidal applications. These applications may include the inhibition, treatment and cure of various medical conditions, such as dermatological conditions.

Example 97

The performance of the unmilled, silver(II) oxide raw material having an average particle size above 5 micrometers, and typically, between 10 and 15 micrometers, was evaluated, in a series of in-vitro tests, against the performance of the milled material having an average particle size between 1 and 5 micrometers. The tests were conducted using cultures containing one of five different microorganisms: *Staphylococcus aureus, Bacillus subtilis, Pseudomonas aeruginosa, Candida albicans*, and *Aspergilus niger*, at least some of which may play an important role in various dermatological conditions, including infections.

In the case of *Aspergilus niger*, no substantial difference in performance was observed. Using *Staphylococcus aureus, Bacillus subtilis, Pseudomonas aeruginosa*, and *Candida albicans*, however, the milled silver(II) oxide of the present invention exhibited a higher efficacy.

Example 98

The exemplary raw materials were crystalline, partially agglomerated silver(II) oxide having a chemical purity of between about 95.5 and 97% and an average particle size (D50) of at least 5 micrometers, and typically, approximately 10 to 20 micrometers, as determined by laser diffraction particle size analysis (Mastersizer™ 2000 of Malvern Instruments, England; Microtrac 53500, USA).

The raw materials were milled in a vortex mill (Superfine Inc., Israel) in a nitrogen-rich environment, to produce a fine silver oxide powder in which much of the agglomerated material has been comminuted. The specific energy applied during the milling process was typically between 6 and 30 kilojoules per kilogram (or kilowatt·second per kilogram), and more typically, between 8 and 25 kilojoules per kilogram. Typically, the milled product had an average particle size that was smaller by at least one micrometer with respect to the average particle size of the unmilled material from which it was produced. More typically, the milled product was smaller by at least 1.2 micrometers, by at least 1.5 micrometers, by at least 2 micrometers, by at least 3 micrometers, or by at least 5 micrometers or by at least 7 micrometers. In most cases, the average particle size was reduced by at least 30%, at least 40%, at least 50%, at least 60%, or at least 80%.

The average particle size of the milled material was above about 0.8 micrometers above about 0.9 micrometers, and more typically, above about 1 micrometer, above about 1.3 micrometers, or above about 1.7 micrometers.

Example 99

The raw materials and the inventive processed powders of Example 98 were subjected to X-ray diffraction. Under the processing conditions of Example 98, we discovered that a portion of the raw material was converted to a crystalline silver(I) oxide ($Ag_2O$), possibly by a mechano-chemical reaction. Using quantitative X-ray diffraction methods, the fraction of crystalline silver(I) oxide in the product material was determined to be higher than the fraction pre-existing in the raw materials. The quantitative X-ray diffraction methods used were found to be insensitive for measuring absolute silver(I) oxide contents below about 3% to 5%. A more accurate quantitative analysis for measuring silver(I) oxide content in a mixed silver oxide environment is provided hereinbelow.

From a quantitative standpoint, the fraction of crystalline silver(I) oxide in the product material was determined to be higher than the fraction pre-existing in the raw materials by at least 1.5%, at least 2%, at least 3%, or at least 4%. In some cases, the fraction of crystalline silver(I) oxide in the product material was determined to be higher than the fraction pre-existing in the raw materials by at least 6%, at least 10%, or at least 15%, by weight.

In absolute terms, the fraction of crystalline silver(I) oxide in the vortex-milled product material was at least 5%, at least 6%, at least 7%, at least 8%, or at least 10%. As is evident from Tables 17 and 18, the fraction of crystalline silver (I) oxide in the product material was, in some cases, at least 20%, at least 23%, or at least 25%, by weight.

TABLE 17

| | $D_{50}$ (micrometers) | $Ag_2O$ content (% w/w) | Description |
|---|---|---|---|
| Sample 1 | 5 | 5> | Unmilled |
| Sample 2 | 2.25 | 14 | Milled according to Example 2 |
| Sample 3 | 1.17 | 23 | Milled according to Example 2 |

TABLE 18

| | $D_{50}$ (micrometers) | $Ag_2O$ content (% w/w) | Description |
|---|---|---|---|
| Sample 4 | 15 | 5> | Unmilled |
| Sample 5 | 2.7 | 27 | Milled according to Example 2 |
| Sample 6 | 2.8 | 31 | Milled according to Example 2 |
| Sample 7 | 3.5 | 19 | Milled according to Example 2 |

We have further discovered that under particular processing conditions, including those described in Example 97, a semi-crystalline or at least partially amorphous silver oxide material may be produced from crystalline silver(II) oxide. At present, we believe that this material may be a semi-crystalline silver(II) oxide. It may be possible that some semi-crystalline silver(III) oxide such as $Ag_2O_3$ is also produced. The production of a semi-crystalline silver(III) oxide may be indicated by the formation of silver(I) oxide described hereinabove, according to the following exemplary reaction:

4 silver(II)oxide(nominally AgO)$\leftrightarrows$1 silver(I)oxide+1 silver(III)oxide (Reaction I)

Alternatively or additionally, oxygen may be liberated, according to the following exemplary reaction:

4 silver(II)oxide(nominally AgO)$\leftrightarrows$2 silver(I)oxide+$O_{2(g)}$ (Reaction II)

However, evidence for the formation of silver(III) oxide remains to be positively demonstrated.

The ratio of silver(I) oxide to silver(II) oxide (or the ratio of substantially crystalline silver(I) oxide to substantially crystalline silver(II) oxide) may exceed about 1:20, 1:18, 1:16, or 1:10, by weight. Typically, the ratio of the silver(I) oxide to the silver(II) oxide (or the ratio of substantially crystalline silver(I) oxide to substantially crystalline silver (II) oxide) may be less than 5:1, less than 2:1, less than 1:1, less than 0.8:1, or less than 0.5:1, by weight. Without wishing to be bound by theory, we believe that this ratio (specifying the relative quantity of silver oxide that is not fully crystalline) may be somewhat dependent on the specific energy applied during the milling process.

It is possible that some of the semi-crystalline material produced is a silver(II) oxide characterized by a low level of crystallinity. This may be supported by the broadening of various X-ray diffraction peaks associated with crystalline silver(II) oxide. For example, Table 3 provides the characteristic of a given diffraction line (2θ=37.23° in the {111} diffraction or symmetry plane) appearing in both the raw material and in milled samples. The comparison refers to the peak heights and full width half maximums (FWHMs). A standard sample containing well-crystallized Si crystals, displayed a FWHM of 0.08°, which may represent the natural line broadening of the diffractometer. Sample 1, consisting of unmilled silver oxide, yielded a FWHM of 0.207°. Samples 2 and 3, which were milled from Sample 1, exhibited broadened peaks having significantly increased FWHMs, 0.355° and 0.446°, respectively. The net broadening, after subtracting the instrumental broadening, is 0.127 for Sample 1, and 0.275 and 0.366, respectively, for vortex-milled Samples 2 and 3, respectively.

Thus, under the specific experimental conditions, the processed powders appear to have undergone a mechano-chemical reaction in two stages. In the first stage, strains are introduced into the structure of the crystals, increasing the irregularity of the lattice structure, i.e., the disarray in the location of the atoms within the lattice structure. In the second stage, a chemical reaction takes place, leading to a partial chemical decomposition of the crystals and the formation of new phases such as silver(I) oxide ($Ag_2O$). Thus, the two-stage mechano-chemical reaction yields a silver(II) oxide lattice structure having a low level of crystallinity, along with at least one additional phase of silver oxide such as silver(I) oxide.

Since the milling process effects changes in the macro-structure of the crystals (i.e., on the order of 1 micrometer), the crystallite size may be substantially unchanged. Hence, the broadening of a diffraction peak associated with crystalline silver(II) oxide may characterize the strain introduced to the crystals during the milling. Alternatively, from the broadening of a peak associated with crystalline silver(II) oxide, the strain introduced to the crystals during the milling process may be calculated.

TABLE 19

| | $D_{50}$ (micrometers) | Peak Height (cps) | Peak full width half maximum (° of 2θ) | Description |
|---|---|---|---|---|
| Sample 1 | 5 | 899 | 0.207 | Unmilled |
| Sample 2 | 2.25 | 438 | 0.355 | Milled according to Example 2 |
| Sample 3 | 1.17 | 255 | 0.446 | Milled according to Example 2 |
| Standard | ~1.0 | 9377 | 0.08 | Si standard - fully crystalline |

Example 100

The specific surface area of various silver oxide samples was determined using a BET procedure, under nitrogen. The results are provided in Table 20.

TABLE 20

| | $D_{50}$ (micrometers) | Specific Surface Area ($m^2/g$) |
|---|---|---|
| Sample 4 | 15 | 0.96 |
| Sample 7 | 3.5 | 1.05 |
| Sample 5 | 2.65 | 1.23 |

The processed mixtures of silver oxides and formulations containing such mixtures, may be appreciably more efficacious than the unprocessed silver(II) oxide raw material. As is evident from Table 20, however, the specific surface area of the inventive materials is only about 10-25% higher than that of the raw material. Consequently, it would appear that the improved efficacy may not be attributable to, or at most, may be only partially attributable to, the very moderate increased specific surface area of the inventive mixed silver oxide materials.

Example 101

To a stirred vessel were introduced 600 grams of water and 240 grams of clear jojoba oil. Subsequently, 50 grams of bentonite and 0.9 grams of silver(II) oxide were introduced, and stirring was continued until a viscous emulsion was produced.

Example 102

To a stirred vessel were introduced 600 grams of water and 10 grams of clear jojoba oil. Subsequently, 50 grams of bentonite and 9.0 grams of silver(II) oxide were introduced, and stirring was continued until a single-phase, water-based cream was produced.

Example 103

Crystalline, partially agglomerated tetrasilver tetroxide (Sample 8), a form of silver(II) oxide, was milled in a vortex mill substantially as described in Example 2. The average particle size ($D_{50}$) of the unmilled raw material was 9.7 micrometers (μ), as determined by laser diffraction particle size analysis (also as above).

After vortex milling, a first portion of the milled material (Sample 9) was characterized, and a second portion was remilled (Sample 10) and then characterized.

Figure 23:
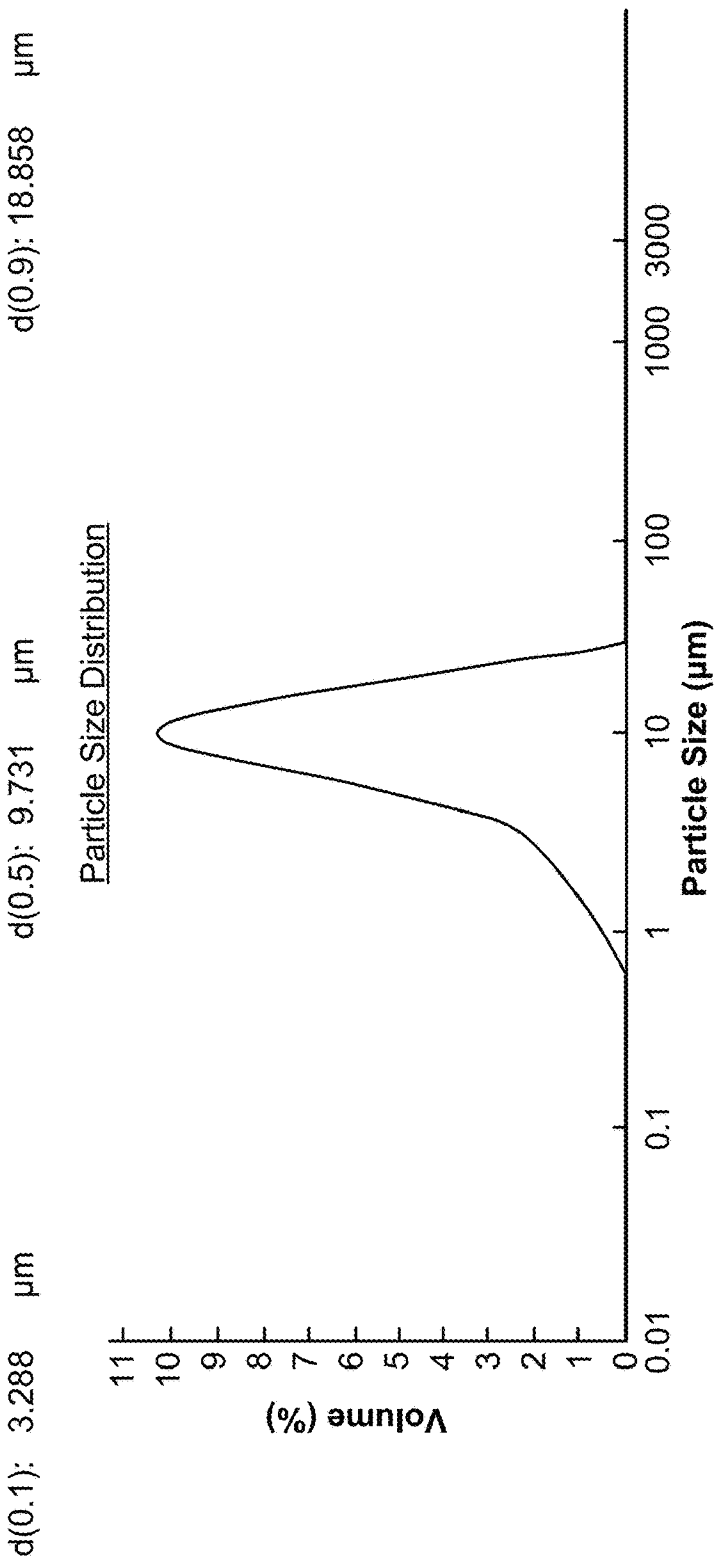
FIG. 23 is a graphical representation of a differential Particle Size Distribution (PSD) of an unmilled silver oxide sample.
Figure 24:
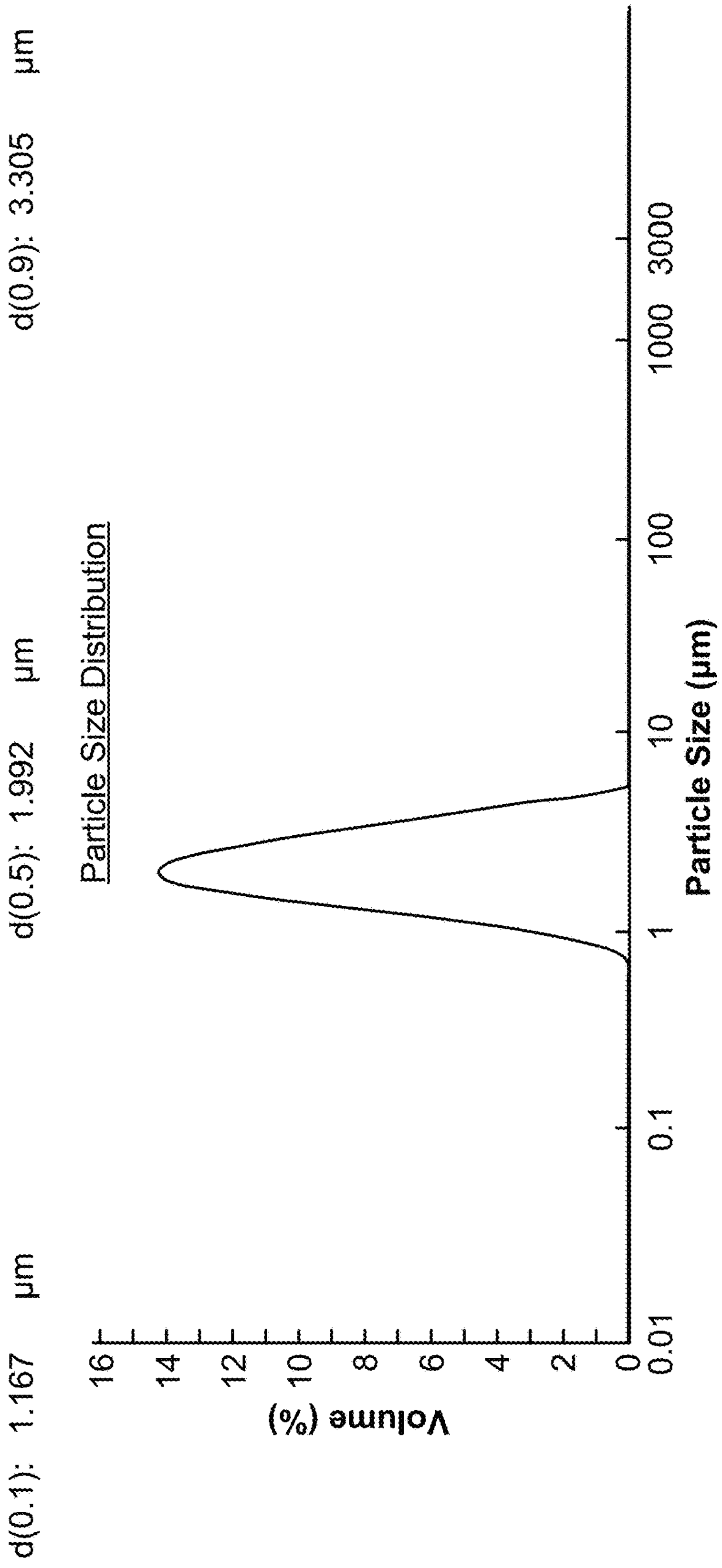
FIG. 24 is a graphical representation of a differential PSD of an inventive silver oxide material produced by a first milling operation in a vortex mill.
Figure 25:
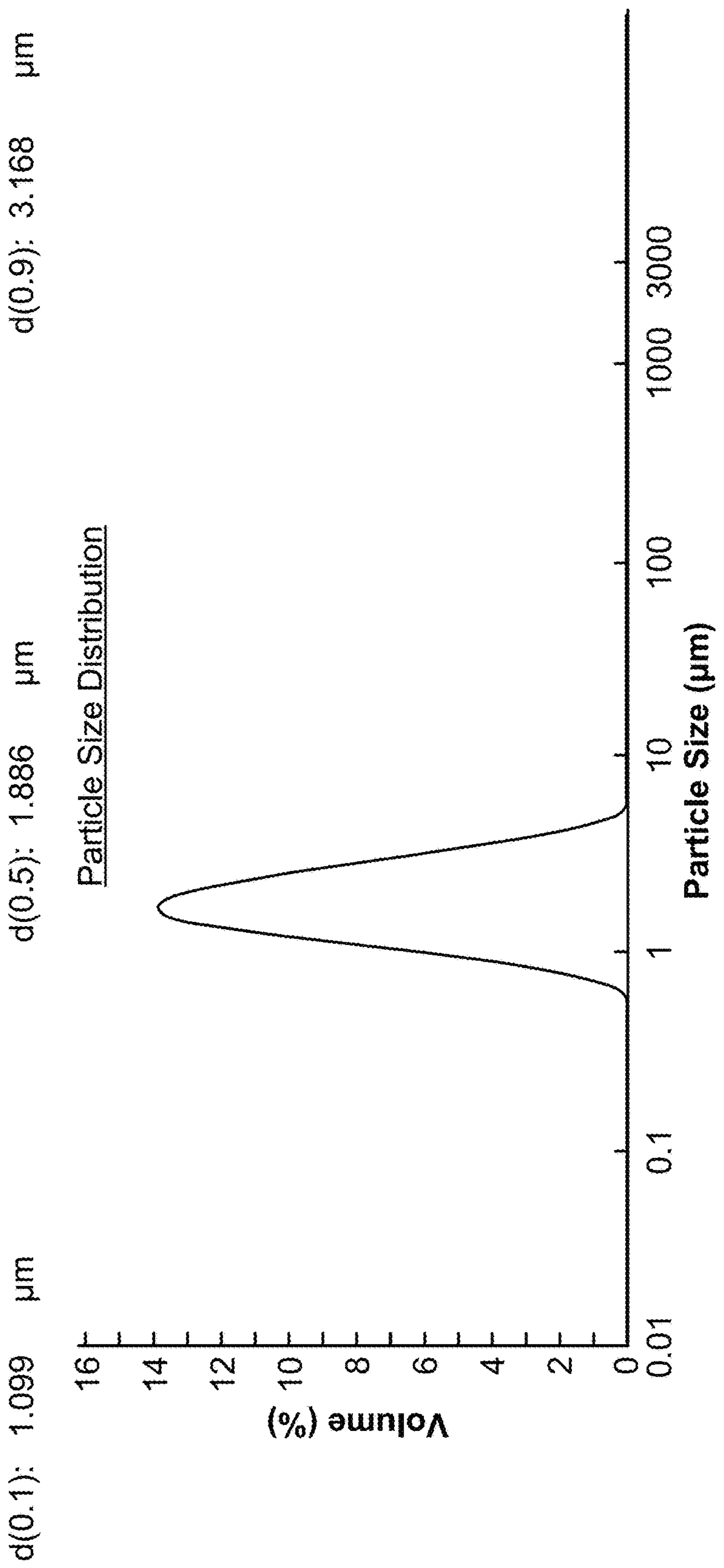
FIG. 25 is a graphical representation of a differential PSD of an inventive silver oxide material produced by vortex-milling the inventive silver oxide sample associated with FIG. 24.

Particle size distributions (PSDs) of the unmilled raw material and of the two milled samples are provided in Table 21. A substantially differential PSD, in which volume percent is plotted as a function of particle size, is provided for each of the three samples in FIGS. 23-25, respectively.

TABLE 21

| | $D_{10}$ (μ) | $D_{50}$ (μ) | $D_{90}$ (μ) | $D_{100}$ (μ) | Description |
|---|---|---|---|---|---|
| Sample 8 | 3.3 | 9.7 | 18.9 | ~30 | Unmilled |
| Sample 9 | 1.1 | 2.0 | 3.3 | ~5.8 | Milled according to Example 2 |
| Sample 10 | 1.1 | 1.9 | 3.2 | ~5.8 | Milled according to Example 2 |

It is evident from Table 21 that the PSD of Sample 10, produced by the additional milling procedure, is extremely similar to the PSD of Sample 9, which had been previously milled.

Example 104

Material from Samples 8-10 were subjected to X-ray diffraction (XRD), using a Rigaku Dmax 2000 XRD analyzer (Rigaku Corporation, Japan).

Figure 26:
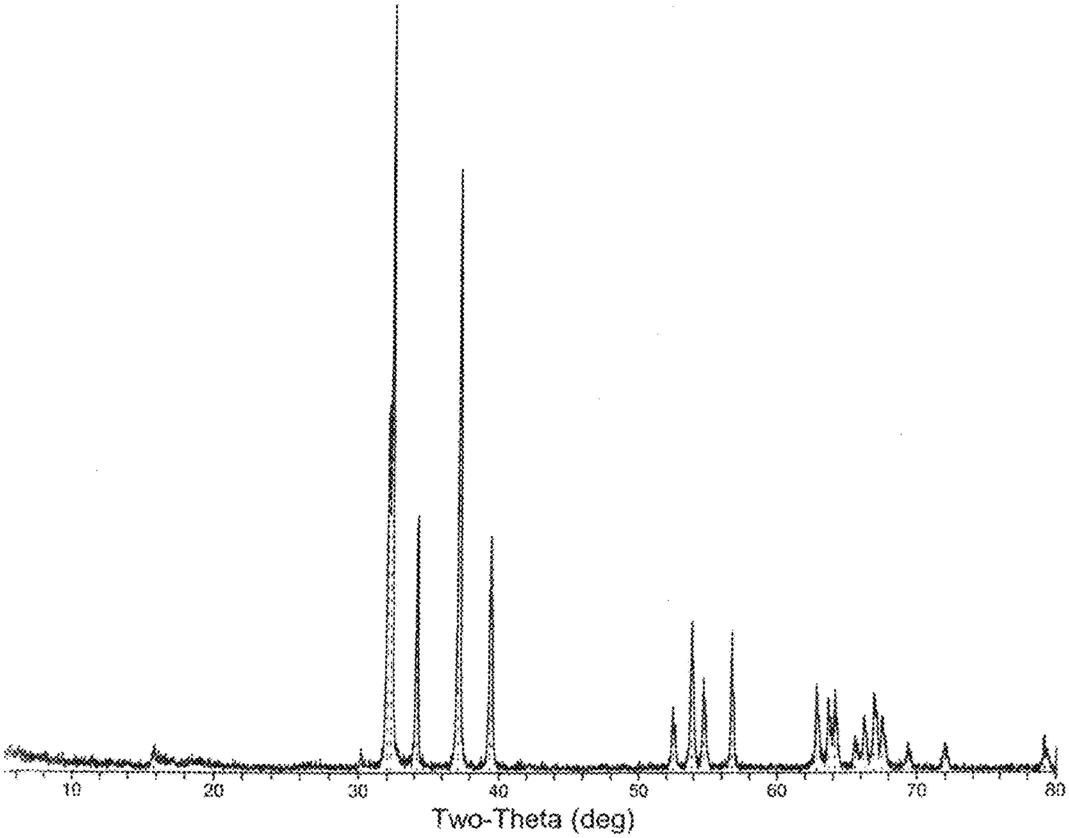
FIG. 26 is an X-ray diffraction plot of the unmilled silver oxide sample associated with FIG. 23.
Figure 27:
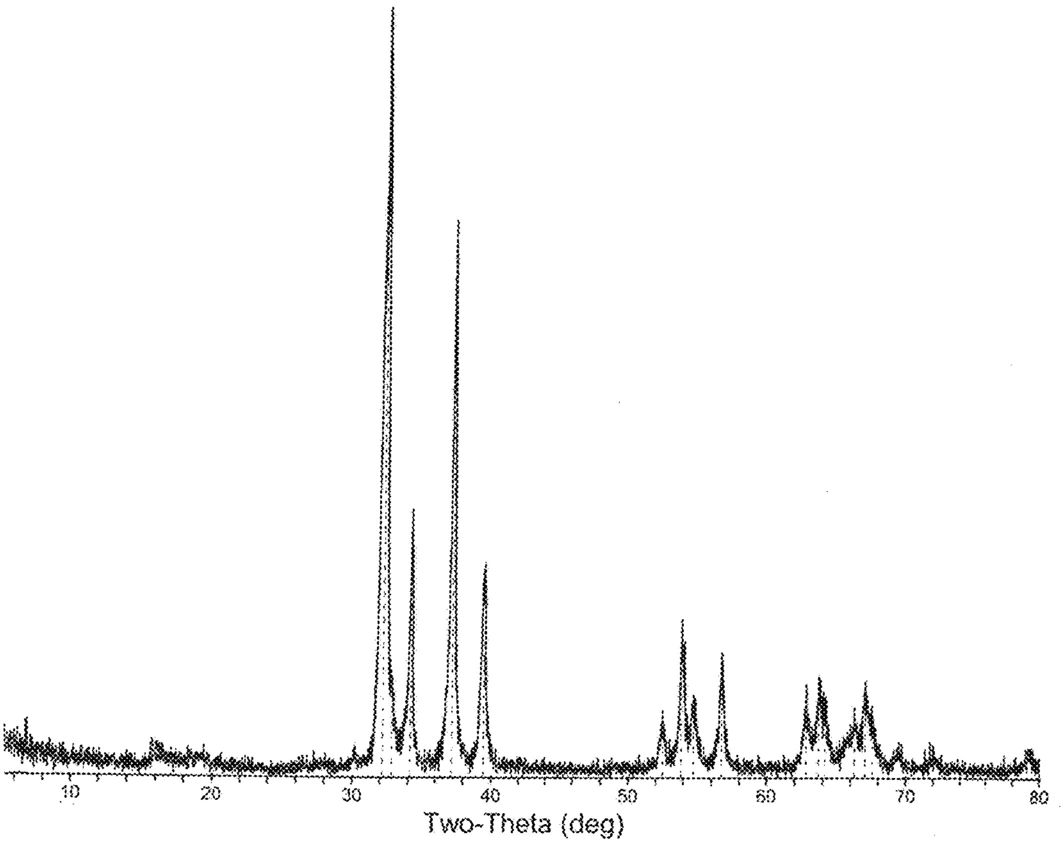
FIG. 27 is an X-ray diffraction plot of the milled silver oxide sample associated with FIG. 24.
Figure 28:
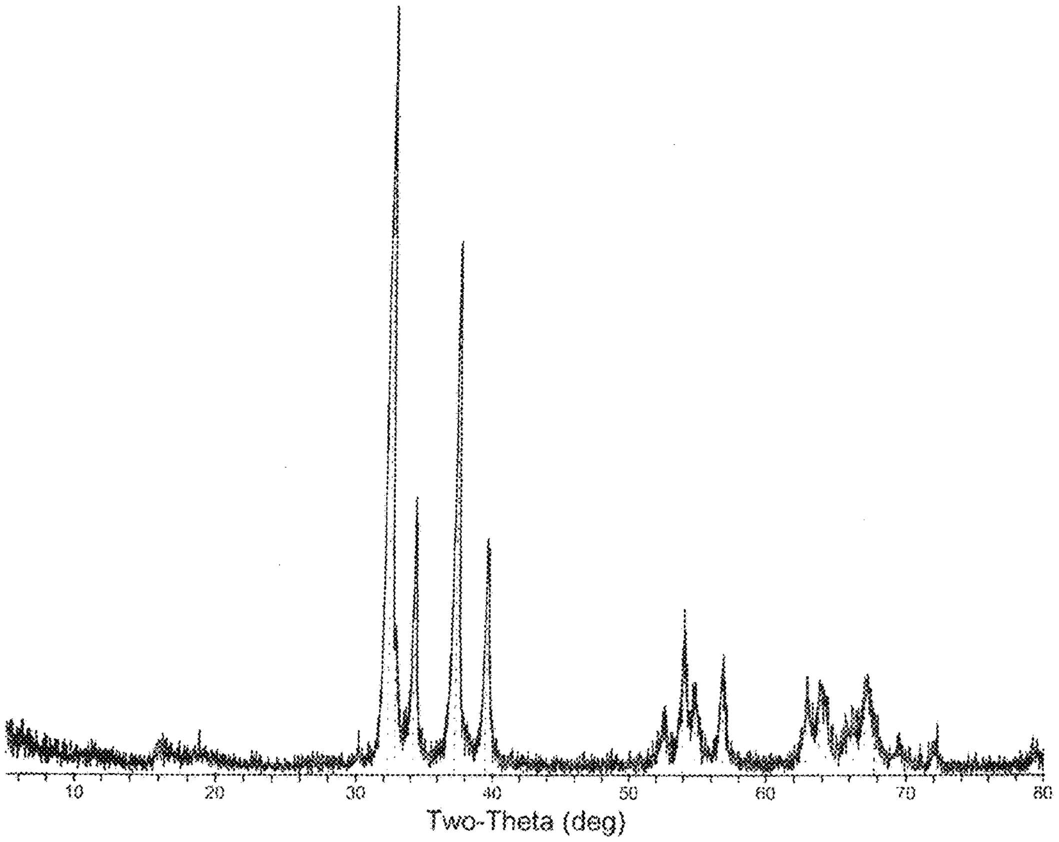
FIG. 28 is an X-ray diffraction plot of the remilled silver oxide sample associated with FIG. 25.
Figure 29:
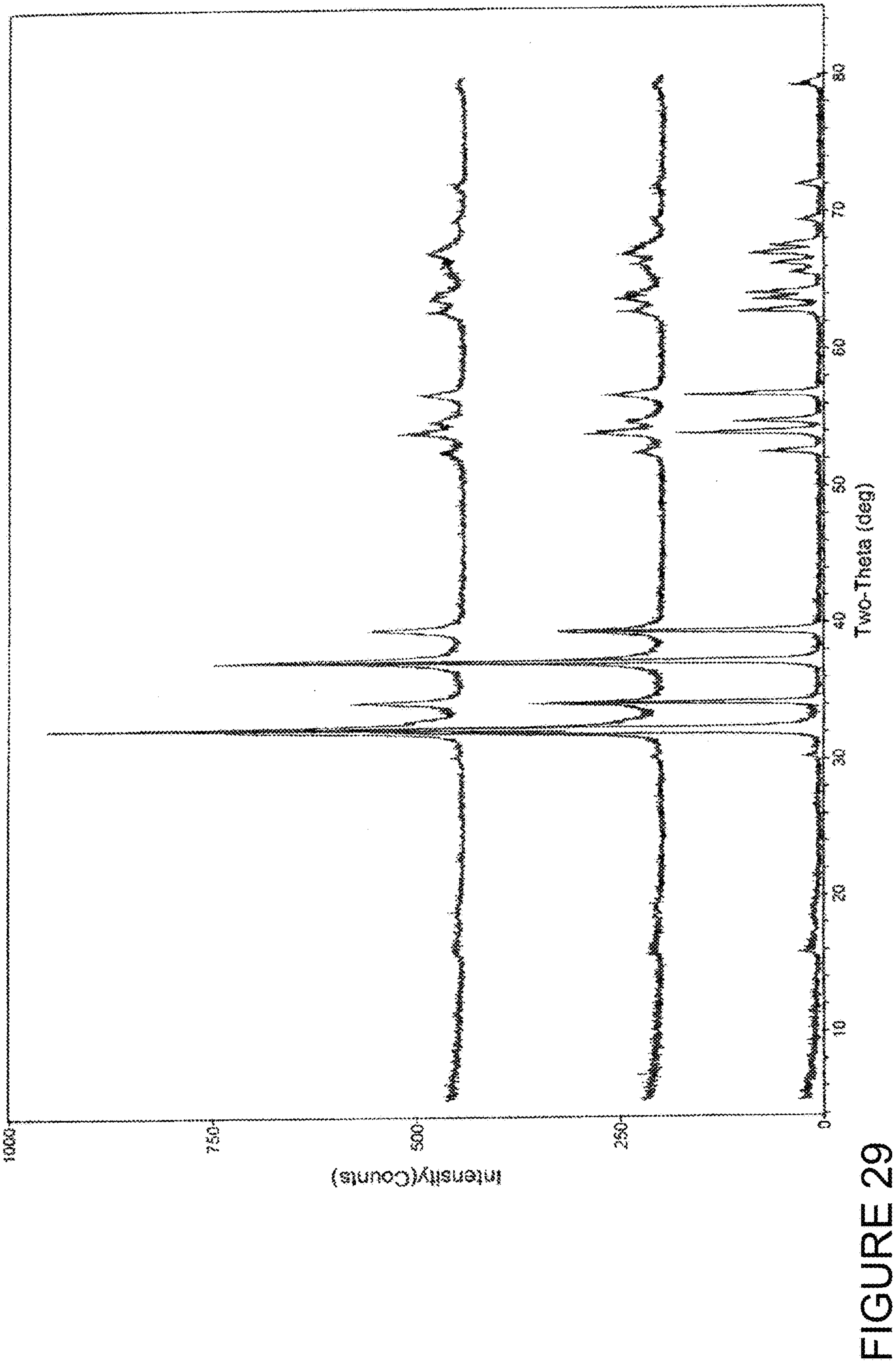
FIG. 29 is a multiple X-ray diffraction plot in which the diffraction patterns of FIGS. 26-28 are superpositioned.

The respective diffraction patterns are plotted in FIGS. 26-28 for Samples 8-10. A superposition of these diffraction patterns is provided in FIG. 29, with the diffraction pattern of Sample 8 plotted near the baseline, the diffraction pattern of Sample 9 plotted thereabove, and the diffraction pattern of Sample 10 plotted yet thereabove. Each of FIGS. 26-28 further includes a table containing detailed data obtained from the three XRD patterns.

The formation of $Ag_2O$ during milling may be observed, for example, the peak emerging at a 2θ of approximately 32.8°. One may further observe a broadening of peaks, a decrease in the intensity of the diffraction lines, and slight shifts in the location of several diffraction peaks.

Without wishing to be bound by theory, we believe that some of the semi-crystalline material produced is a silver(II)

oxide characterized by a low level of crystallinity. This may be supported by the broadening of various X-ray diffraction peaks associated with crystalline silver(II) oxide. For example, Tables 22-24 provide the characteristic of a given diffraction line (2θ lies between 37.1° and 37.3° in the {111} symmetry plane) appearing in both the raw material (Sample 8) and in the vortex-milled materials (Samples 9 and 10). The comparison refers to the peak heights and full width half maximums (FWHMs), as described hereinabove. Sample 8, consisting of unmilled silver oxide, yielded a FWHM of 0.190°. Vortex-milled Sample 9 which was milled from Sample 8, exhibited a broadened peak having an FWHM of 0.312°. Vortex-milled Sample 10 which was produced by remilling Sample 9, exhibited a further broadening of peak, characterized by an FWHM of 0.356°.

The net broadening, after subtracting the instrumental broadening, is 0.110 for Sample 8, and 0.232 and 0.276, respectively, for vortex-milled Samples 9 and 10, respectively.

Example 105

Material from Samples 8-10 was subjected to chemical analysis. The silver content was determined using an inductively coupled plasma (ICP) spectrometer (Varian AES Vista AX), and oxygen content was determined by means of a thermogravimetric analysis (TGA) instrument (TA Instruments, USA), under a nitrogen environment. The chemical analyses of the samples are provided in Table 22.

TABLE 22

| | | Stage 1 | | Stage 2 | | | Total | [$Ag_2O$] |
|---|---|---|---|---|---|---|---|---|
| | [Ag] (%) | [O] (%) | Temp. (° C.) | [O] (%) | Temp. (° C.) | [O] Total (%) | [Ag] + [O] (%) | calculated (%) |
| Sample 8 | 88.75 | 5.95; | 204.6 | 6.94; | 420.8 | 12.89 | 101.64 | 3.9 |
| Sample 9 | 89.35 | 5.78; | 197.5 | 6.93; | 421.1 | 12.71 | 102.06 | 7.7 |
| Sample 10 | 89.55 | 5.86; | 194.1 | 6.84; | 422.2 | 12.70 | 102.25 | 8.3 |

Figure 30:
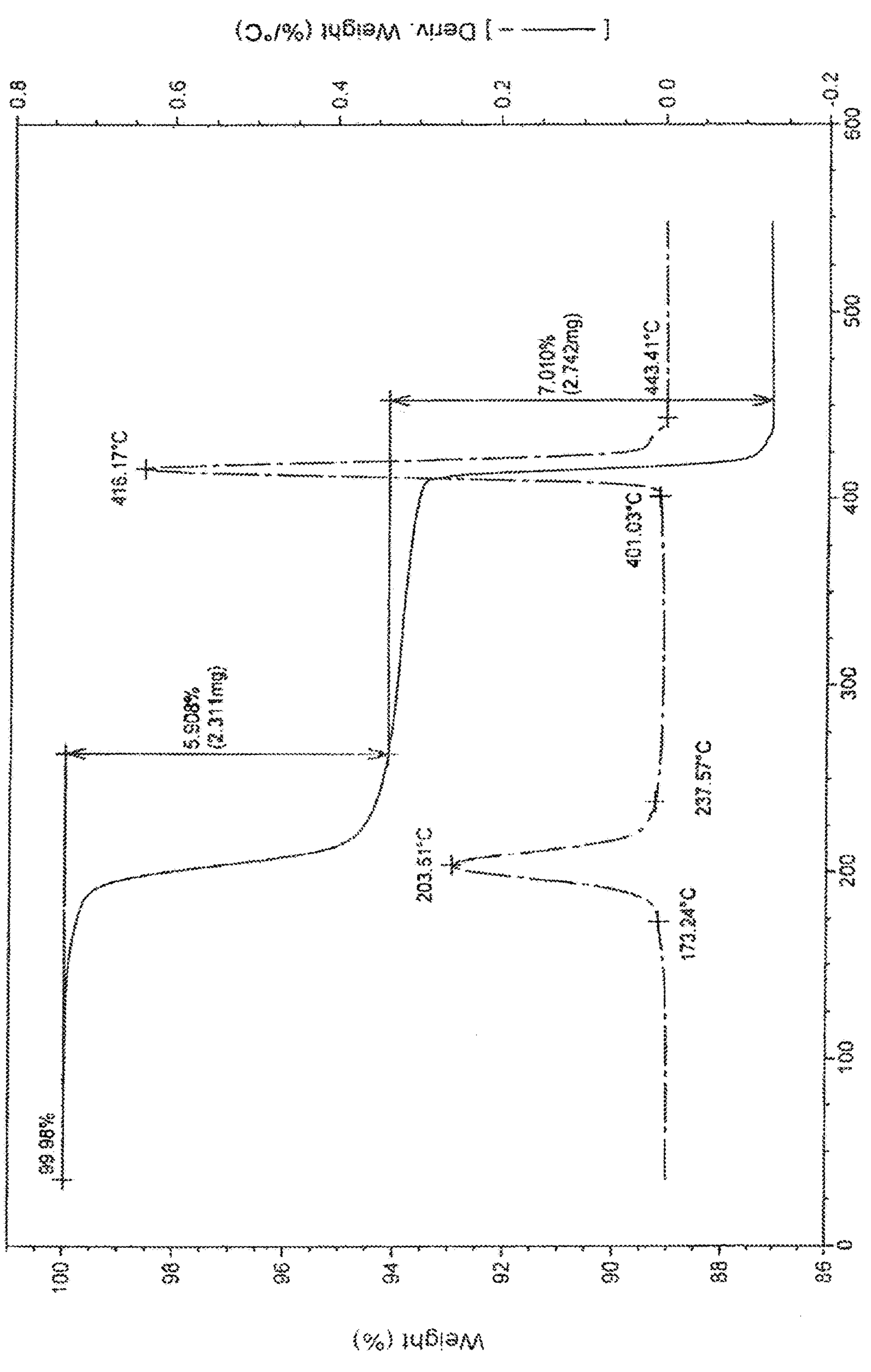
FIG. 30 is a plot of the thermogravimetric analysis (TGA) performed on the unmilled silver oxide sample associated with FIG. 23.
Figure 31:
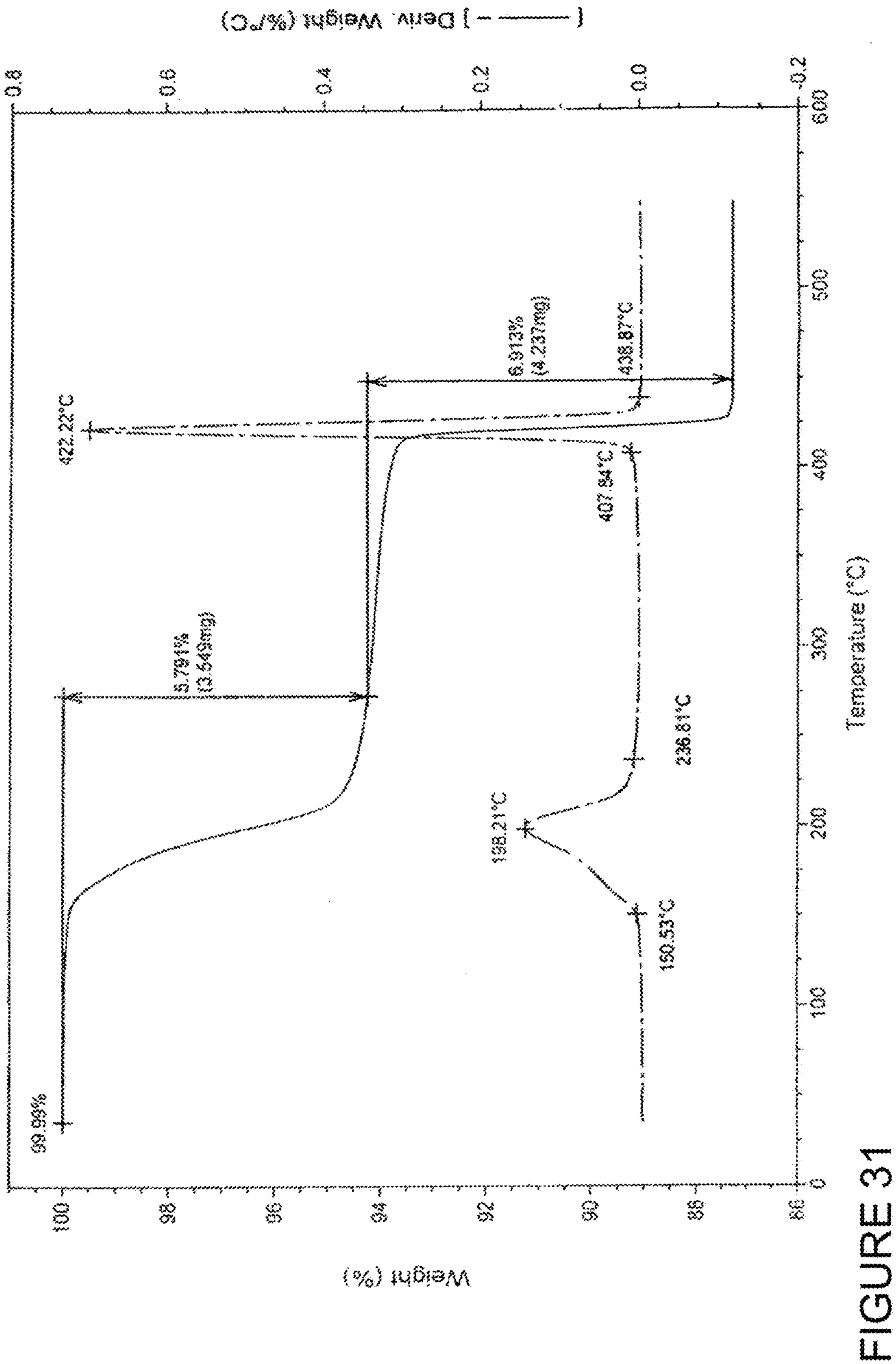
FIG. 31 is a plot of the thermogravimetric analysis (TGA) performed on the vortex-milled silver oxide sample associated with FIG. 24.
Figure 32:
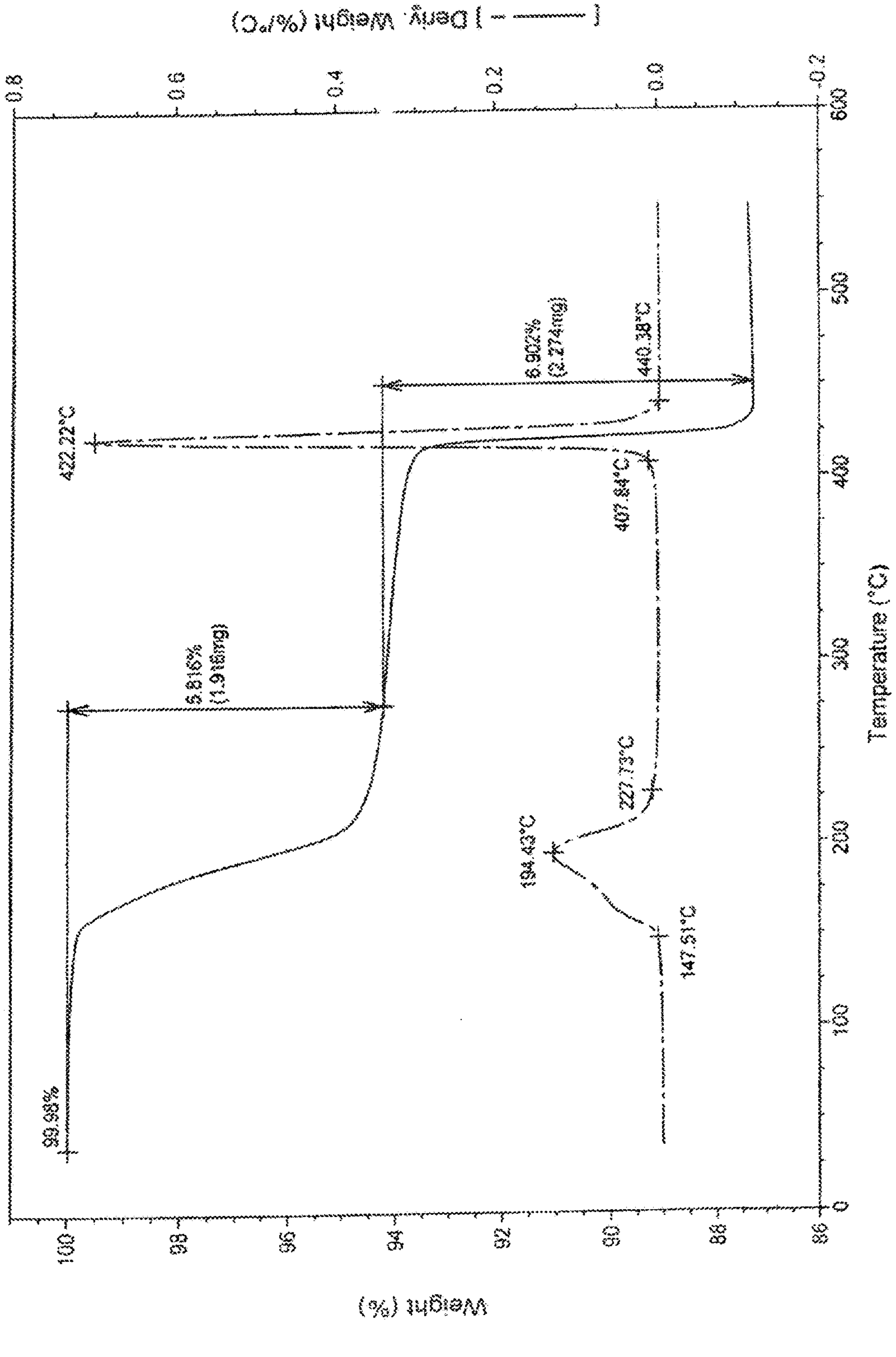
FIG. 32 is a plot of the thermogravimetric analysis (TGA) performed on the remilled silver oxide sample associated with FIG. 25.

In FIGS. 30-32, the percentage of the original sample weight is plotted as a function of temperature on the first Y-axis; the derivative of this curve ("derivative curve") is plotted on the second Y-axis. The temperature in the TGA sample chamber was ramped up from room temperature (25° C.) to about 550° C., at a rate of 10° C./minute.

The oxygen in the solid samples appears to be liberated in two distinct stages: in a first stage, around 200° C., in which the more labile oxygen is driven off, and in a second stage, around 420° C., in which the remainder is driven off.

Referring now to the first stage, and with specific reference to the derivative curve, the weight loss per unit change in temperature (dW/dT) associated with the evolution of oxygen from Sample 8 is substantially constant until 173° C. At 173° C., dW/dT begins to accelerate ("first shoulder of the derivative") at about 173° C., peaks at 204° C. (i.e., reaches a constant, maximum rate of weight loss per unit increase in temperature), and decelerates and largely concludes at 238° C. By sharp contrast, the derivative curve peak for milled Sample 9 is at 198° C., and the accelerated evolution of oxygen from Sample 9 begins at about 151° C., over 20° C. lower than the corresponding value for Sample 8. With regard to twice-milled Sample 10, the derivative curve peak is at 194° C., and the accelerated weight loss associated with the evolution of oxygen from Sample 9 begins at about 148° C., over 25° C. lower than the corresponding value for Sample 8. The differences in the respective derivative curve peak profiles (of the first stage) are particularly apparent in the graphical representations provided in FIGS. 8-10. The peak profile broadens, and loses its sharpness, with increased milling time in the vortex mill.

Without wishing to be limited by theory, we believe that the weight loss/evolution of oxygen at significantly lower temperatures may be at least partially attributed to the increased strain within the silver oxide particles, which correspondingly increases the lability of the oxygen. In any event, it is surprising that the oxygen is more easily liberated than in the raw material or in pure silver(II) oxide. The induced strain is a structural characteristic that may be at least partially responsible for the increased reactivity of the inventive material, and for the enhanced anti-microbial properties of the topical formulations according to the present invention.

We further observe that the percent weight loss of the oxygen decreases for silver oxide milled in the vortex mill, with respect to the percent weight loss of the unmilled raw material. The percent weight loss associated with Sample 10 is substantially identical to that of Sample 9, which may indicate that little additional oxygen was liberated in the second milling operation.

As used herein in the specification and in the claims section that follows, the term "2θ", with respect to X-ray diffraction, is meant to be used as understood in the art of X-ray diffraction.

With respect to θ-θ XRD analyzers in which the specimen is fixed (such as the Rigaku Dmax 2000 XRD analyzer), 2θ is meant to represent the angle of the detector with respect to the specimen.

As used herein in the specification and in the claims section that follows, the term "full width half maximum", or "FWHM" of a diffraction peak is meant to be used as understood in the art of X-ray diffraction.

Since the magnitude of the measured FWHM includes instrumental broadening, the values of FWHM as claimed include such broadening, which is estimated to be 0.08-0.10 degrees of 2θ for the Rigaku Dmax 2000 XRD analyzer used, using a silicon diffraction pattern as the baseline. Thus, as used herein in the claims section that follows, the magnitude of the FWHM includes an instrumental broadening of 0.08-0.10 degrees of 2θ.

As used herein in the specification and in the claims section that follows, the term "net full width half maximum", or "net FWHM" of a diffraction peak is meant to refer to the magnitude of the measured FWHM, less the instrumental broadening, as determined using a silicon diffraction pattern as the baseline.

As used herein in the specification and in the claims section that follows, the term "macrocrystal" and the like refers to a crystal composed of a large plurality of crystallites, and/or having a particle size of at least 0.5 micrometers, at least 0.6 micrometers, or at least 1.0 micrometers.

A material is said to have a macrocrystal structure if over 90% of the material, by weight, consists of macrocrystals.

As used herein in the specification and in the claims section that follows, the term "semi-crystalline" refers to a substantially macrocrystalline material having a low level or degree of crystallinity.

In the specific case of a material containing silver (II) oxide, the term "semi-crystalline" refers to a substantially macrocrystalline material having a low level or degree of crystallinity defined by a diffraction peak in a {111} symmetry plane and having a full width half maximum (FWHM) of at least 0.24 degrees of 2θ.

As used herein in the specification and in the claims section that follows, the term "silver (II) oxide" refers to a silver oxide whose unit structure contains silver and oxygen in a substantially 1:1 molar ratio. The term "silver (II) oxide" is specifically meant to include AgO, and $Ag_4O_4$ (tetrasilver tetroxide), whose structure may be represented by $Ag_2O_3.Ag_2O$.

As used herein in the specification and in the claims section that follows, the term "average particle size", or "$D_{50}$", refers to an average particle size, by weight, as determined by a laser diffraction particle size analyzer (e.g., Mastersizer™ 2000 of Malvern Instruments, England, or the like), using standard practice.

As used herein in the specification and in the claims section that follows, the term "percent", or "%", refers to percent by weight, unless specifically indicated otherwise.

Similarly, the term "ratio", as used herein in the specification and in the claims section that follows, refers to a weight ratio, unless specifically indicated otherwise.

As used herein in the specification and in the claims section that follows, the term "largely includes", with respect to a component within a formulation, refers to a weight content of at least 30%.

As used herein in the specification and in the claims section that follows, the term "mainly includes", with respect to a component within a formulation, refers to a weight content of at least 50%.

As used herein in the specification and in the claims section that follows, the term "predominantly includes", with respect to a component within a formulation, refers to a weight content of at least at least 65%.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method comprising:

(a) providing a silver oxide raw material, said silver oxide raw material predominately including silver (II) oxide;

(b) milling said silver oxide raw material in a vortex mill, to produce a silver oxide powder in which the average particle size is smaller than an average particle size of said silver oxide raw material by at least one micrometer, and wherein said silver oxide powder has an average particle size ($D_{50}$) within a range of from above 0.8 micrometers to below 8 micrometers;

wherein said silver oxide powder contains a silver (I) oxide and said silver (II) oxide, and wherein a concentration of said silver (I) oxide in said silver oxide powder exceeds a concentration of said silver (I) oxide in said silver oxide raw material.

2. The method of claim 1, wherein said silver(II) oxide in said silver oxide powder has an irregular macrocrystal structure, said irregular macrocrystal structure characterized by a diffraction peak in a {111} diffraction plane, said diffraction peak having at least one of the following structural properties:

(i) a measured full width half maximum (FWHM) of at least 0.30 degrees of 2θ and not more than 0.466 degrees of 2θ; and (ii) a net full width half maximum (net FWHM) of at least 0.20 degrees of 2θ and not more than 0.366 degrees of 2θ.

3. The method of claim 1, wherein said silver(II) oxide in said silver oxide powder has an irregular macrocrystal structure, wherein said irregular macrocrystal structure is structurally characterized by a lability pattern of a thermogravimetric analysis (TGA) performed on said solid phase in a chamber, under a pure nitrogen environment and a temperature ramp rate of 10° C./minute, said lability pattern characteristic of structural properties within said irregular macrocrystal structure, said lability pattern having both of the following properties:

(i) a derivative of weight loss of said solid phase with respect to a temperature change in said chamber peaks at a temperature below 202° C. and at least 194° C.; and (ii) a first shoulder of said derivative appears below 160° C. and at least 148° C.

4. The method of claim 2, further comprising formulating said silver oxide powder in a topical formulation suitable for application to skin tissue, said topical formulation having a form selected from the group consisting of an ointment, oil-based cream, water-base cream, or emulsion.

5. The method of claim 3, further comprising formulating said silver oxide powder in a topical formulation suitable for application to skin tissue, said topical formulation having a form selected from the group consisting of an ointment, oil-based cream, water-base cream, or emulsion.

6. The method of claim 1, further comprising formulating said silver oxide powder in a topical formulation suitable for application to skin tissue.

7. The method of claim 2, further comprising formulating said silver oxide powder in a topical formulation suitable for application to skin tissue.

8. The formulation of claim 6, wherein, within said topical formulation, said silver oxide powder is dispersed in a base material, and wherein said base material includes a liquid wax ester.

9. The formulation of claim 8, wherein said liquid wax ester includes jojoba oil.

10. The formulation of claim 5, said average particle size ($D_{50}$) being within a range of from above 0.8 micrometers to 4.5 micrometers.

11. The formulation of claim 5, containing at least 0.05%, by weight, of said silver(II) oxide.

12. A method comprising:

(a) providing a silver oxide raw material, said silver oxide raw material predominantly including a silver(II) oxide;

(b) milling said silver oxide raw material in a vortex mill, to produce a silver oxide powder in which an average particle size is smaller than an average particle size of said silver oxide raw material by at least one micrometer;

wherein said silver oxide powder contains a silver(I) oxide and said silver(II) oxide, and wherein a concentration of said silver(I) oxide in said silver oxide powder exceeds a concentration of said silver(I) oxide in said silver oxide raw material;

wherein said silver oxide powder has an average particle size ($D_{50}$) within a range of from above 0.8 micrometers to below 8 micrometers;

wherein said silver(II) oxide in said silver oxide powder has an irregular macrocrystal structure;

and wherein said irregular macrocrystal structure is characterized by a diffraction peak in a {111} diffraction plane, said diffraction peak having both of the following structural properties:

(i) a measured full width half maximum (FWHM) of at least 0.30 degrees of 2θ and not more than 0.466 degrees of 2θ; and (ii) a net full width half maximum (net FWHM) of at least 0.20 degrees of 2θ and not more than 0.366 degrees of 2θ;

(c) formulating said silver oxide powder in a topical formulation suitable for application to skin tissues;

wherein said topical formulation has a form selected from the group consisting of an ointment, oil-based cream, water-base cream, or emulsion.

13. The method of claim 12, said silver oxide powder present in sufficient concentration to be efficacious as a topical anti-microbial.

14. The method of claim 12, wherein said form is said ointment or oil-based cream.

15. The method of claim 12, wherein said form is said water-based cream.

16. The method of claim 13, wherein said form is said emulsion.

17. The method of claim 13, wherein said topical formulation is incorporated into a wound dressing.

18. The method of claim 2, wherein a ratio of said silver(I) oxide to said silver(II) oxide is at least 0.05:1, by weight.

19. The method of claim 1, wherein said average particle size ($D_{50}$) is below 4.5 micrometers.

* * * * *